(12) United States Patent
Norden et al.

(10) Patent No.: US 6,228,982 B1
(45) Date of Patent: May 8, 2001

(54) DOUBLE-STRANDED PEPTIDE NUCLEIC ACIDS

(76) Inventors: Benget Norden, Dorjeskaragatan 15, S-421 60 Vastra Frolunda; Pernilla Wittung, Djurgardsgatan 27, S-414 62 Gothenburg, both of (SE); Ole Buchardt, Sondergardsvej 73, DK 3500 Vaerlose (DK); Michael Egholm, Johnstrup Alle, 3, DK 1923 Fredriksberg (DK); Peter E. Nielsen, Hjortevanget 509, DK 2980 Kokkedal (DK); Rolf Berg, Strandvaenget 6, DK 2960 Rungsted Kyst (DK)

( * ) Notice: Subject to any disclaimer, the term of this patent is extended or adjusted under 35 U.S.C. 154(b) by 0 days.

(21) Appl. No.: 08/088,661

(22) Filed: Jul. 2, 1993

Related U.S. Application Data

(63) Continuation-in-part of application No. 08/054,363, filed on Apr. 26, 1993, now Pat. No. 5,539,082, which is a continuation-in-part of application No. PCT/EP92/01219, filed on May 22, 1992.

(51) Int. Cl.$^7$ ................. C07K 5/00; C12Q 1/68
(52) U.S. Cl. ................. 530/300; 435/6; 514/2; 514/44; 530/333; 530/402
(58) Field of Search ............... 530/300, 333, 530/402, 345; 514/2, 44; 435/6

(56) References Cited

U.S. PATENT DOCUMENTS 5,142,047 * 8/1992 Summerton et al. ............ 544/118

FOREIGN PATENT DOCUMENTS

8605518 * 9/1986 (WO).
9312129 * 6/1993 (WO).

OTHER PUBLICATIONS

Egholm et al, "Peptide Nucleic Acids (PNA) . . . ", pp 325–328 in *Innovation and Perspectives in Solid Phase Synthesis Collected Papers*, (1992).*
Hanvey et al, "Antisense and Antigene Properties of Peptide Nucleic Acids", *Science* 258: 1481–1485 (Nov. 1992).*
Takemoto et al, "Synthetic Nucleic Acid Analogs Preparation and Interaction" *Adv. Poly. Sci. 41*: 1–51 (1981).*
Gewirtz, "Therapeutic Application of Antisense DNA . . . ", pp 178–187 in *Antisense Strategies*, published 1992 by NYAS.*
Hyrup et al, "Modification of the Binding Afinity of Peptide Nucleic Acids (PNA) . . . " *J. Chem. Soc., Chem. Commun.*, pp 518–519 (Mar. 1993).*
Nielsen et al "Sequence–Selective Recognition of DNA by Strand Displacement with a Thymine–Substituted Polyamide", *Science* 254:1497–1500 (Dec. 1991).*
Egholm et al, "Peptide Nucleic Acids (PNA) . . . " *J. Am. Chem. Soc. 114*: 1895–1897. (Feb. 1992).*

(List continued on next page.)

Primary Examiner—Ardin H. Marschel
(74) Attorney, Agent, or Firm—Woodcock Washburn Kurtz Mackiewicz & Norris LLP

(57) ABSTRACT

A novel class of compounds, known as peptide nucleic acids, form double-stranded structures with one another and with ssDNA. The peptide nucleic acids generally comprise ligands such as naturally occurring DNA bases attached to a peptide backbone through a suitable linker.

14 Claims, 3 Drawing Sheets

OTHER PUBLICATIONS

Buttrey et al, "Synthetic Analogues of Polynucleotides . . . " *Tetrahedron 31*: 73–75 (Jan. 1975).*

Doel et al, "The Synthesis of Peptides Containing Purine and Pyrimidine Derivatives of DL–Alanine", *Tetrahedron 30*: 2755–2759 (1974).*

Lu et al, "Synthesis of Polyesters Containing Nucleic Acid Base Derivatives as Pending Side Chains", *J. Poly.Sci: Part A: Poly.Chem. 24*:525–536 (1986).*

Meier et al, "Peptide Nucleic Acids (PNAs) . . . " Angew. Chem. Int. Ed. Eng. 31(8): 1008–1010 (Jul. 1992).*

Blackwell et al., "Sequence–Specific DNA Binding by the c–Myc Protein," *Science*, 250:1149–1151, 1990.

Cullen et al., "The HIV–1 Tat Protein: An RNA Sequence–Specific Processivity Factor," *Cell*, 63:655–657, 1990.

Franza, Jr. et al., "Characterization of cellular proteins recognizing the HIV enhancer using a microscale DNA–affinity precipitation assay," *Nature*, 330:391–395, 1987.

Gilmore et al., "Different Localization of the Product of the v–rel Oncogene in chicken Fibroplasts and Spleen Cells Correlates with Transformation by REV–T," *Cell*, 44:791–800, 1986.

Konig et al., "Autoregulation of fos: the dyad symmetry element as the major target of repression," *EMBO Journal*, 8:2559–2566, 1989.

Nisen et al., "Enhanced Expression of the N–myc Gene in Wilms' Tumors," *Cancer Research*, 46:6217–6222, 1986.

Vasseur et al., "Oligonucleotides: Synthesis of a Novel Methylhydroxylamine–Linked Nucleoside Dimer and Its Incorporation into Antisense Sequences," *J. Am. Chem. Soc.*, vol. 114, pp 4006–4007 (1992).

* cited by examiner

DOUBLE-STRANDED PEPTIDE NUCLEIC ACIDS

RELATED APPLICATION

This patent application is related to the patent application entitled Higher Order Structure And Binding Of Peptide Nucleic Acids, U.S. Ser. No. 08/088,658, filed Jul. 2, 1993. This patent application also is a continuation-in-part of patent application Ser. No. 08/054,363, filed Apr. 26, 1993 now U.S. Pat. No. 5,539,082, which is a continuation-in-part of application PCT EP92/01219, filed May 22, 1992 and published Nov. 26, 1992 as WO 92/20702. The entire contents of each of the foregoing patent applications are incorporated herein by reference.

FIELD OF THE INVENTION

This invention is directed to generally linear compounds or "strands" wherein naturally-occurring nucleobases or other nucleobase-binding moieties preferably are covalently bound to a polyamide backbone. In particular, the invention concerns compounds wherein two such strands coordinate through hydrogen bonds to form a DNA-like double strand.

BACKGROUND OF THE INVENTION

The transcription and processing of genomic duplex DNA is controlled by generally proteinaceous transcription factors that recognize and bind to specific DNA sequences. One strategy for the control of gene expression is to add to a cell double-stranded DNA or double-stranded DNA-like structures that will bind to the desired factor in preference to or in competition with genomic DNA, thereby inhibiting processing of the DNA into a protein. This modulates the protein's action within the cell and can lead to beneficial effects on cellular function. Naturally occurring or unmodified oligonucleotides are unpractical for such use because they have short in vivo half-lives and they are poor cell membrane penetrators.

These problems have resulted in an extensive search for improvements and alternatives. In order to improve half-life as well as membrane penetration, a large number of variations in polynucleotide backbones has been undertaken. These variations include the use of methylphosphonates, phosphorothioates, phosphordithioates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives. The great majority of these backbone modifications lead to decreased stability for hybrids formed between the modified oligonucleotide and its complementary native oligonucleotide, as assayed by measuring $T_m$ values.

Consequently, there remains a need in the art for stable compounds that can form double-stranded, helical structures mimicking double-stranded DNA.

OBJECTS OF THE INVENTION

It is one object of the present invention to provide compounds that mimic the double-helical structure of DNA.

It is a further object of the invention to provide compounds wherein linear, polymeric strands coordinate through hydrogen bonds to form double helices.

It is another object to provide compounds wherein naturally-occurring nucleobases or other nucleobase-binding moieties are covalently bound to a non-sugar-phosphate backbone.

It is yet another object to provide therapeutic, diagnostic, and prophylactic methods that employ such compounds.

SUMMARY OF THE INVENTION

The present invention provides a novel class of compounds, known as peptide nucleic acids (PNAs), that can coordinate with one another or with single-stranded DNA to form double-stranded (i.e., duplex) structures. The compounds include homopolymeric PNA strands and heteropolymeric PNA strands (e.g., DNA/PNA strands), which coordinate through hydrogen bonding to form helical structures. Duplex structures can be formed, for example, between two complementary PNA or PNA/DNA strands or between two complementary regions within a single such strand.

In certain embodiments, each strand of the double-stranded compounds of the invention includes a sequence of ligands covalently bound by linking moieties and at least one of said linking moieties comprising an amide, thioamide, sulfinamide or sulfonamide linkage. The ligands on one strand hydrogen bond with ligands on the other strand and, together, assume a double helical structure. The compounds of the invention preferably comprise ligands linked to a polyamide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, 5-propynylthymine, etc.) attached to a peptide backbone through a suitable linker. These ligands are linked to the polyamide backbone through aza nitrogen atoms or through amido and/or ureido tethers.

In certain preferred embodiments, the peptide nucleic acids of the invention have the general formula (I):

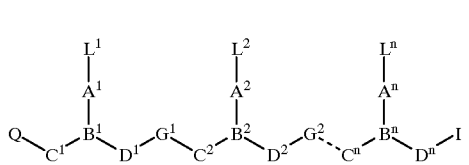

(I)

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$–$L^n$ being a naturally occurring nucleobase, a non-naturally occurring nucleobase, a DNA intercalator, or a nucleobase-binding group;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $(CR^6R^7)_z$ where $R^6$ and $R^7$ are as defined above;

each of y and z is zero or an integer from 1 to 10, the sum y+z being greater than 2 but not more than 10;

each of $G^1$–$G^{n-1}$ is —$NR^3CO$—, —$NR^3CS$—, —$NR^3SO$— or —$NR^3SO_2$—, in either orientation, where $R^3$ is as defined above;

each pair of $A^1$–$A^n$ and $B^1$–$B^n$ are selected such that:
(a) A is a group of formula (IIa), (IIb) or (IIc) and B is N or $R^3N^+$; or
(b) A is a group of formula (IId) and B is CH;

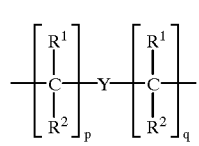
(IIa)

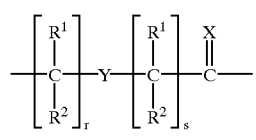
(IIb)

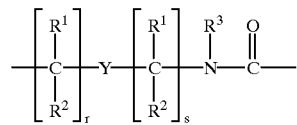
(IIc)

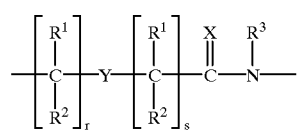
(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1$–$C_4)$alkyl which may be hydroxy- or alkoxy- or alkylthio-substituted, hydroxy, alkoxy, alkylthio, amino and halogen;

each of $G^1$–$G^{n-1}$ is —$NR^3CO$—, —$NR^3CS$—, —$NR^3SO$— or —$NR^3SO_2$—, in either orientation, where $R^3$ is as defined above;

Q is —$CO_2H$, —CONR'R", —$SO_3H$ or —$SO_2NR'R"$ or an activated derivative of —$CO_2H$ or —$SO_3H$; and I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

In certain embodiments, at least one A is a group of formula (IIc) and B is N or $R^3N^+$. In other embodiments, A is a group of formula (IIa) or (IIb), B is N or $R^3N^+$, and at least one of y or z is not 1 or 2.

Preferred peptide nucleic acids have general formula (IIIa)–(IIIc):

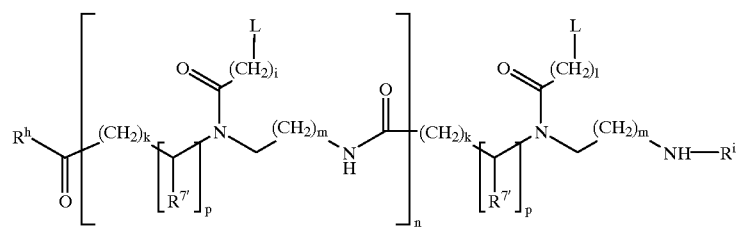
(IIIa)

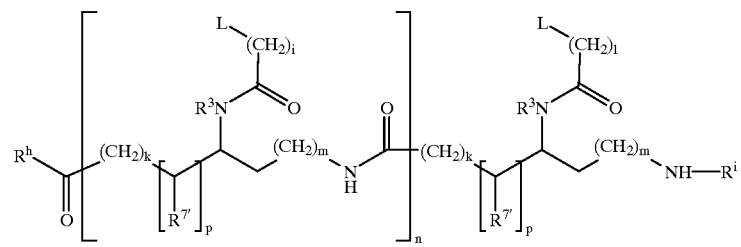
(IIIb)

-continued (IIIc)

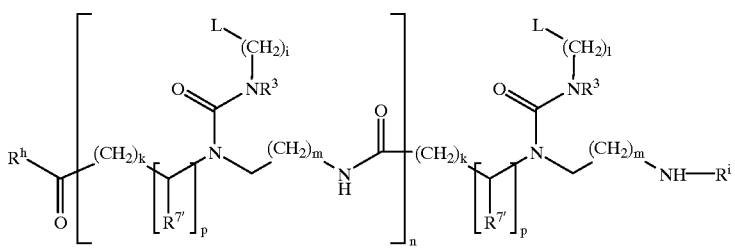

wherein:
each L is independently selected from the group consisting of hydrogen, phenyl, heterocyclic moieties, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;
each of k, l, and m is independently zero or an integer from 1 to 5;
p is zero or 1;
$R^h$ is OH, $NH_2$ or —$NHLysNH_2$; and
$R^i$ is H or $COCH_3$.

Particularly preferred are compounds having formula (IIIa)–(IIIc) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20.

The peptide nucleic acids of the invention are synthesized by adaptation of standard peptide synthesis procedures, either in solution or on a solid phase. The synthons used are monomer amino acids or their activated derivatives, protected by standard protecting groups. The PNAs also can be synthesized by using the corresponding diacids and diamines.

Thus, the novel monomer synthons according to the invention are selected from the group consisting of amino acids, diacids and diamines having general formulae:

(IV)

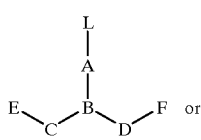

or (V)

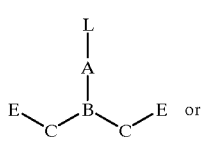

or (VI)

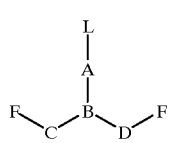

wherein L, A, B, C and D are as defined above, except that any amino groups therein may be protected by amino protecting groups; E is COOH, CSOH, SOOH, $SO_2OH$ or an activated derivative thereof; and F is $NHR^3$ or $NPgR^3$, where $R^3$ is as defined above and Pg is an amino protecting group.

Preferred monomer synthons according to the invention have formula (VIIIa)–(VIIIc):

(VIIIa)

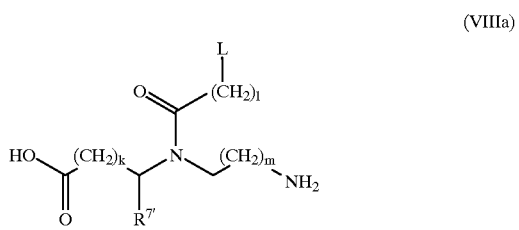

(VIIIb)

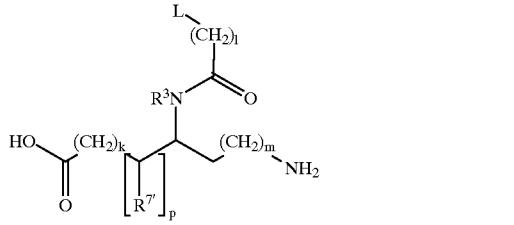

(VIIIc)

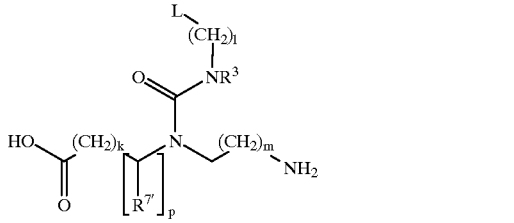

or amino-protected and/or acid terminal activated derivatives thereof, wherein L is selected from the group consisting of hydrogen, phenyl, heterocyclic moieties, naturally occurring nucleobases, and non-naturally occurring nucleobases; and $R^{7'}$ is selected from the group consisting of hydrogen and the side chains of naturally occurring alpha amino acids.

These compounds are able to recognize one another to produce double helices. Such recognition can span sequences 5–60 base pairs long. Sequences between 10 and 20 bases are of interest since this is the range within which unique DNA sequences of prokaryotes and eukaryotes are found. Sequences between 17–18 bases are of particular interest since this is the length of unique sequences in the human genome.

Thus, in one aspect, the present invention provides methods for modulating the activity of a transcription factor in a cell, comprising the steps of forming a PNA-containing double strand that binds the transcription factor and introducing the double strand into the cell.

Further, the invention provides methods for modulating the activity of a protein in a cell, comprising the steps of forming a PNA-containing double strand that binds to or suppresses expression of the protein and introducing the double strand into the cell.

The PNA duplex structures of the invention mimic dsDNA and can be used in diagnostics, therapeutics and as research reagents and kits. They can be used in pharmaceutical compositions by including a suitable pharmaceutically acceptable diluent or carrier.

BRIEF DESCRIPTION OF THE FIGURES

The numerous objects and advantages of the present invention may be better understood by those skilled in the art by reference to the accompanying figures, in which.

DETAILED DESCRIPTION OF THE INVENTION

As will be recognized, a variety of double-stranded (i.e., duplex) PNA-containing structures can be prepared according to the present invention. Representative duplexes can be formed within a single homopolymeric PNA strand or a single heteropolymeric strand (e.g., a chimera PNA-DNA or PNA-RNA strand), or between two homopolymeric PNA strands, two heteropolymeric PNA strands, or a homopolymeric PNA strand and a heteropolymeric PNA strand.

Figure 2:
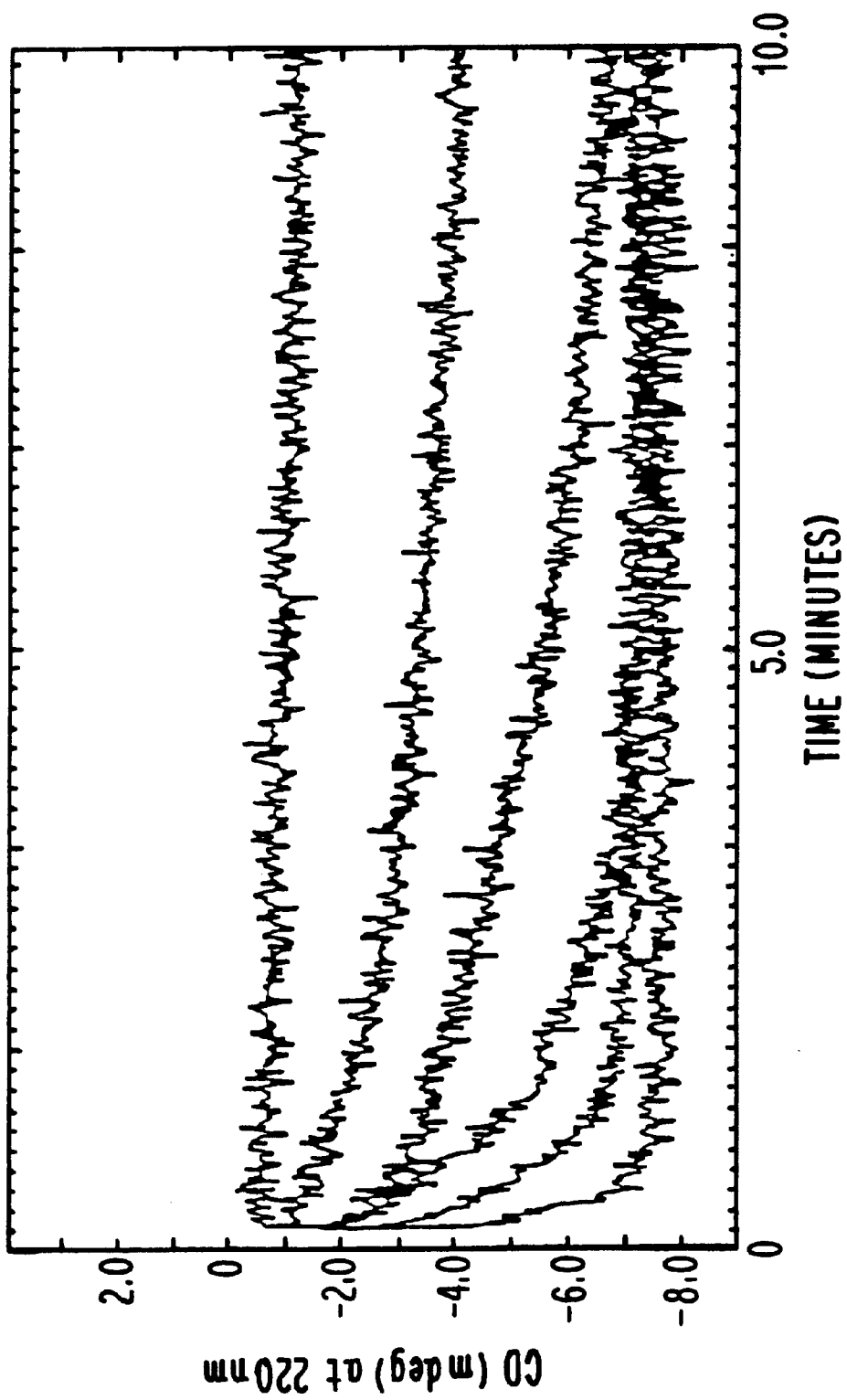
FIG. 2 is the development in time of the circular dichroism signal of certain compounds of the invention.

Each PNA strand or PNA portion of a chimera strand preferably comprises a plurality of ligands, L, linked to a backbone via attachment at the position found in nature, i.e., position 9 for adenine or guanine, and position 1 for thymine or cytosine. Alternatively, L can be a non-naturally occurring nucleobase (nucleobase analog), another base-binding moiety, an aromatic moiety, $(C_1-C_4)$alkanoyl, hydroxy or even hydrogen. It will be understood that the term nucleobase includes nucleobases bearing removable protecting groups. Some typical nucleobase ligands and illustrative synthetic ligands are shown in FIG. 2 of WO 92/20702. Furthermore, L can be a DNA intercalator, a reporter ligand such as, for example, a fluorophor, radio label, spin label, hapten, or a protein-recognizing ligand such as biotin. In monomer synthons, L can be blocked with protecting groups, as illustrated in FIG. 4 of WO 92/20702.

Linker A can be a wide variety of groups such as —$CR^1R^2CO$—, —$CR^1R^2CS$—, —$CR^1R^2CSe$—, —$CR^1R^2CNHR^2$—, —$CR^1R^2C=CH_2$— and —$CR^1R^2C=C(CH_3)_2$—, where $R^1$, $R^2$ and $R^3$ are as defined above. Preferably, A is methylenecarbonyl (—$CH_2CO$—), amido (—$CONR^3$—), or ureido (—$NR^3CONR^3$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a $(C_2-C_6)$alkylene chain, a $(C_2-C_6)$alkylene chain substituted with $R^1R^2$ or can be heterogenous, containing Y. In certain cases, A can just be a single bond.

In one preferred form of the invention, B is a nitrogen atom, thereby presenting the possibility of an achiral backbone. B can also be $R^3N^+$, where $R^3$ is as defined above, or CH.

In the preferred form of the invention, C is —$CR^6R^7$—, but can also be a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In a preferred form of the invention, E in the monomer synthon is COOH or an activated derivative thereof, and G in the oligomer is —$CONR^3$—. As defined above, E also can be CSOH, SOOH, $SO_2OH$ or an activated derivative thereof, whereby G in the oligomer becomes —$CSNR^3$—, —$SONR^2$— and —$SO_2NR^3$—, respectively. The activation can, for example, be achieved using an acid anhydride or an active ester derivative, wherein hydrogen in the groups represented by E is replaced by a leaving group suited for generating the growing backbone.

The amino acids which form the backbone can be identical or different. We have found that those based on 2-aminoethylglycine are especially well suited to the purpose of the invention.

In some cases it may be of interest to attach ligands at either terminus (Q, I) to modulate other properties of the PNAs. Representative ligands include DNA intercalators or basic groups, such as lysine or polylysine. Further groups such as carboxy and sulfo groups could also be used. The design of the synthons further allows such other moieties to be located on non-terminal positions.

Duplexes according to the present invention can be assayed for their specific binding activity to a transcription factor. As used herein, the term "binding affinity" refers to the ability of a duplex to bind to a transcription factor via hydrogen bonds, van der Waals interactions, hydrophobic interactions, or otherwise. For example a duplex can bind to a "leucine zipper" transcription factor or a helix-loop-helix transcription factor via positively charged amino acids in one region of the transcription factor.

Transcription factors, as the term is used herein, are DNA- or RNA-binding proteins that regulate the expression of genes. HIV tat and c-rel are examples of transcription factors which regulate the expression of genes. Also encompassed by the term are DNA and RNA binding proteins which are not strictly considered transcription factors, but which are known to be involved in cell proliferation. These transcription factors include c-myc, fos, and jun. Methods of the present invention are particularly suitable for use with transcription factor as target molecules since transcription factors generally occur in very small cellular quantities.

The compounds of the present invention also may be useful to bind to other target molecules. Target molecules of the present invention can include any of a variety of biologically significant molecules. Such other target molecules can be nucleic acid strands such as significant regions of DNA or RNA. Target molecules also can be carbohydrates, glycoproteins or other proteins. In some preferred embodiments of the present invention, the target molecule is a protein such as an immunoglobulin, receptor, receptor binding ligand, antigen or enzyme and more specifically can be a phospholipase, tumor necrosis factor, endotoxin, interleukin, plasminogen activator, protein kinase, cell adhesion molecule, lipoxygenase, hydrolase or transacylase. In other embodiments of the invention the target molecules can be important regions of the human immunodeficiency virus, Candida, herpes viruses, papillomaviruses, cytomegalovirus, rhinoviruses, hepatitises, or influenza viruses. In yet other embodiments of the present invention the target molecules can be regions of an oncogene. In still further embodiments, the target molecule is ras 47-mer stem loop RNA, the TAR element of human immunodeficiency virus or the gag-pol stem loop of human immunodeficiency virus (HIV). Still other targets can induce cellular activity. For example, a target can induce interferon.

In binding to transcription factors or other target molecules, the transcription factor or other target molecule need not be purified. It can be present, for example, in a whole cell, in a humoral fluid, in a crude cell lysate, in serum or in other humoral or cellular extract. Of course, purified transcription factor or a purified form of an other target molecule is also useful in some aspects of the invention.

In still other embodiments of the present invention, synthetically prepared transcription factor or other target molecule can be useful. A transcription factor or other target molecule also can be modified, such as by biotinylation or radiolabeling. For example, synthetically prepared transcription factor can incorporate one or more biotin molecules during synthesis or can be modified post-synthesis.

An illustrative series of PNA oligomers according to the invention can be prepared as described in Example 1 below and have been designed as follows:

(1) Formulas 1 (SEQ ID NO:1) and 2 (SEQ ID NO:2), two complementary antiparallel PNA decamers that are not self-complementary:

(aminoterminal) H-Gly-GTAGATCACT-LysNH$_2$  1

NH$_2$Lys-CATCTAGTGA-GlyH (aminoterminal)  2

(2) Formula 3 (SEQ ID NO:3), a single PNA oligomer possessing a self-complementary motif ten base pairs long with an intervening loop region containing five base units:

H-Gly-GTAGATCACT-TT
                  T
NH$_2$Lys-CATCTAGTGA-TT

3

(3) Formula 4 (SEQ ID NO:4), a single PNA oligomer possessing a self complementary motif of ten base pairs long linked by an oligomethylene (n=1–10) spacer:

H-GlyGTAGATCACT-(CH$_2$)$_n$
                         |
NH$_2$Lys-CATCTAGTGA-CH$_2$

4

(4) Formula 5 (SEQ ID NO:5), a single PNA oligomer possessing a self-complementary motif ten base pairs long on one side interrupted by a three base bulge and an intervening loop region containing five base units:

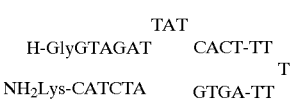

```
              TAT
H-GlyGTAGAT        CACT-TT
                          T
NH$_2$Lys-CATCTA   GTGA-TT
```

5

In each of the foregoing, NH$_2$Lys is intended to indicate that a lysine-amide is attached to the carboxyl end of the PNA. Use of such lysine-amide is not necessary; however, its use is preferred since it is believed to suppress aggregation of the oligomers. The aminoterminal end of the PNA is substituted with a glycine residue to avoid migration of the N-terminal nucleobase. The PNA amino-terminal and carboxy-terminal ends are intended to correspond, respectively, to the 5'-ends and 3'-ends of DNA. As a consequence of the designed sequences, these PNAs form duplexes having DNA-like antiparallel orientations. These PNAs additionally are capable of adopting a tertiary structure.

Figure 1:
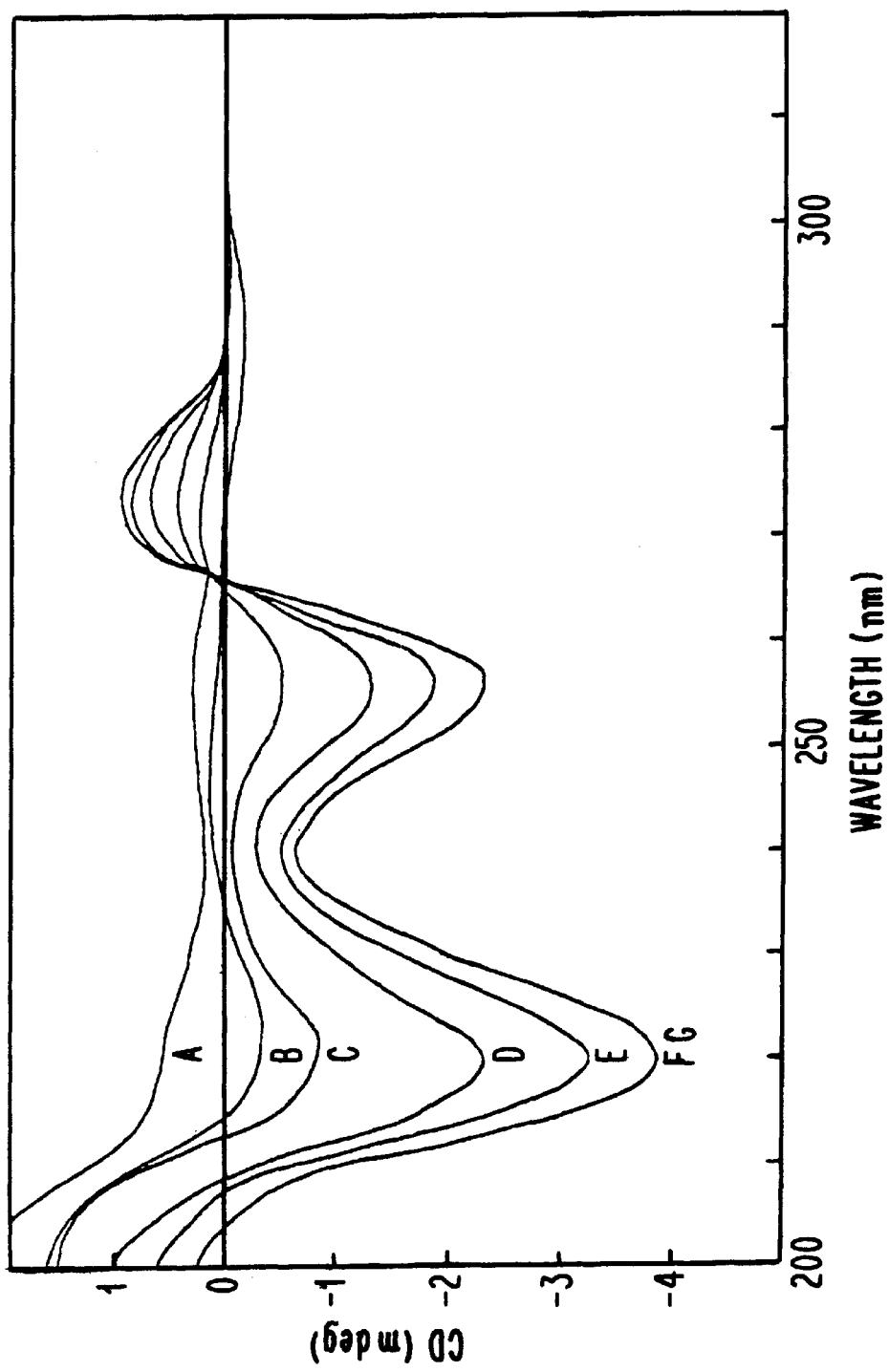
FIG. 1 is a plot showing titration to saturation of a 10 mer PNA to a complementary 10 mer PNA.

As can be seen in FIG. 1, the circular dichroism (CD) of PNA 10-mers of Example 1 are almost vanishingly small, indicating that there is no preferred helical stacking of bases. However, a strong CD spectrum arises upon titration of one 10-mer with the complementary 10-mer, a saturation obtained at about 1:1 stoichiometry, as shown in FIG. 2. The CD spectrum resembles that of B-DNA, indicating a right-handed helix. It is believed that a PNA-PNA complex having no preferred helicity initially is formed. The kinetics by which this double-stranded structure reorganizes into a uniform, right-handed double helix has been monitored and the activation parameters for the process determined.

Figure 3:
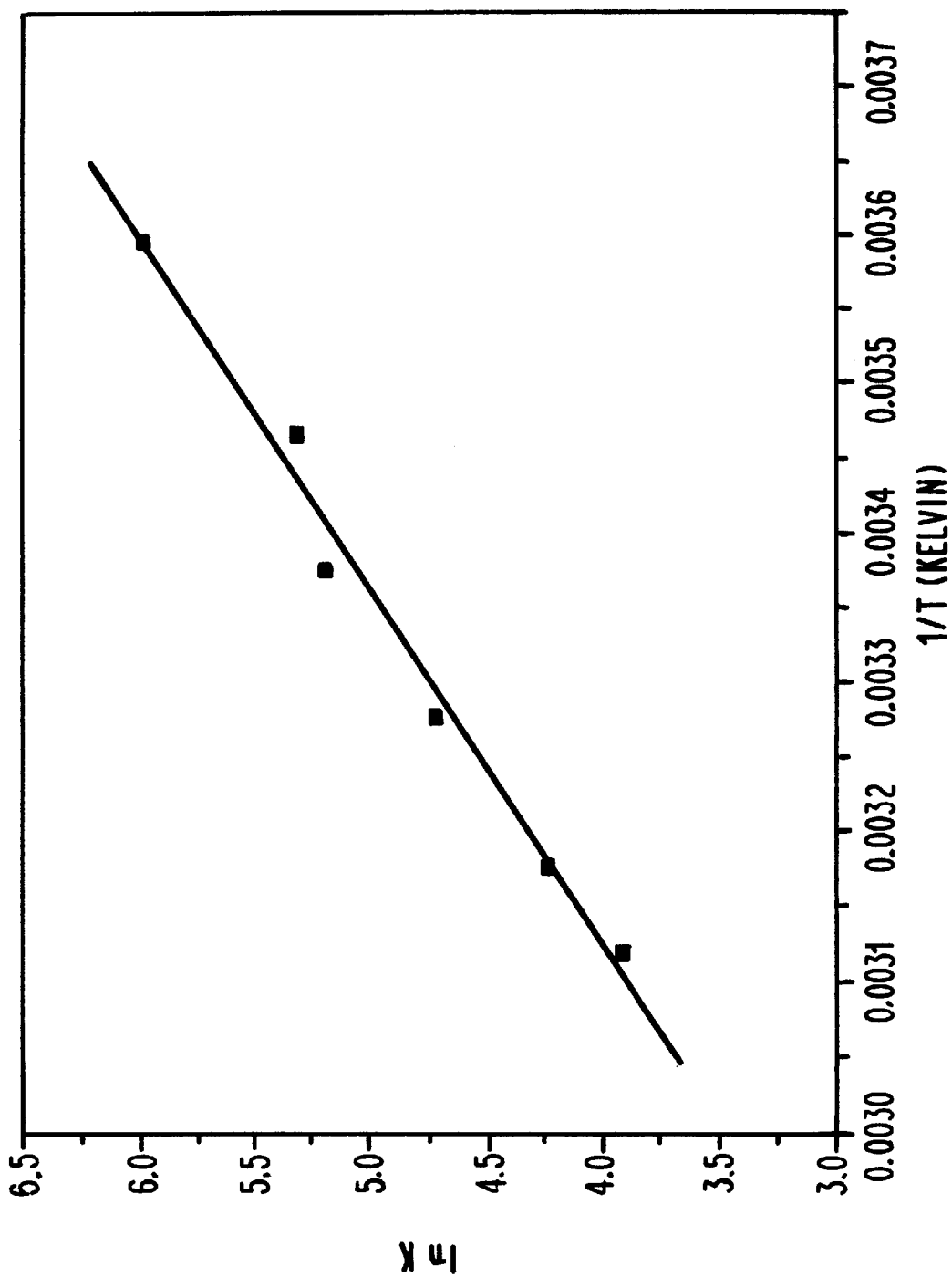
FIG. 3 is an Arrhenius plot of reaction rates at various temperatures during helical duplexation.

For DNA, circular dichroism in the nucleobase absorption region arises both from helical stacking of the bases, by excitation interactions between the neighboring bases, and from interactions with transitions of the chiral riboses moieties. In contrast, in PNA the electronic interaction between most of the bases and the chiral terminal lysine is negligible and the main source of circular dichroism is attributable almost solely to the chiral orientation of the base-pairs relative to each other. The right-handed helicity observed for PNA is determined by the chiral bias of a terminal lysine residue. The formation of a helical duplex between the two complementary PNA oligomers was slow enough to be followed by the increase in circular dichroism with time. This is in contrast with DNA-DNA duplex formation, which occurs within seconds. The development of circular dichroism follows first order reaction kinetics. Activation parameters have been determined by following the association at various temperatures, as shown in FIG. 3. Control experiments with different PNA concentrations gave identical results, confirming that the PNA-PNA association is fast and includes a reorganization process in an already base-paired complex. This observation is further supported by the absence of time dependent hypochromicity in normal absorption spectra. Such a reorganization in the corresponding cases of DNA-DNA and DNA-PNA decamers duplexes is too fast to be observed, indicating that the local chirality of the ribose in those cases immediately determines the handedness of base stacking. The conclusion is that the association of the two PNA-oligomers is fast in the base-pairing first step, but is followed by a slow seeding of the duplex chirality, from the terminal lysine residue, towards its right-handed helical structure. The activation energy obtained is 33.9 kJ/mole, which is low because the transition state is associated with a large negative entropy change ($\Delta S=-173$ kJ/mole; see, e.g., FIG. 3), implying a highly ordered transition state. This is a strong indication that the rate-limiting inversion step is a cooperative seeding of chirality from the terminal base-pairs involving the entire stack of bases.

We believe this is the first time a pure cooperative inversion transition in a nucleic acid-like structure has been isolated. Also, in contrast to DNA wherein ribose residues act as local chiral centers, optical activity of PNA-PNA duplexes is entirely a result of the helical arrangement of the nucleobases relative to each other. The CD spectrum can be compared with the theoretical and experimental spectra that have been generated for helix stacks of DNA bases to demonstrate the mimicry of DNA duplex structure. These PNA-PNA duplexes therefore are useful mimics of DNA for the purpose of modulating the expression or transcription of DNA and thus modulating a disease state to the benefit of a living organism.

The utility of these PNA-containing duplex structures can be illustrated by constructing PNA sequences which correspond to various sequences of the HIV TAR element that have the potential to form duplex structures either as stem-loop structures or two PNAs forming a duplex structure. In a competition assay, PNA structures that bind the tat transcription factor prevent binding of the competitor TAR sequence present in the incubation mixture. As the TAR RNA sequence is biotinylated only tat proteins available to bind to TAR will remain on the microtiter plate after washing away unbound molecules and tat protein complexed to a PNA sequence. The concentration dependence of the competition between the TAR PNA structures and biotinylated TAR structure will serve to define those sequences capable of effectively competing for tat and thus useful as HIV modulatory agents.

Additional objects, advantages, and novel features of this invention will become apparent to those skilled in the art upon examination of the following examples thereof, which are not intended to be limiting.

EXAMPLE 1

Synthesis of PNA Structures

PNA having formulas 1 through 5 above are prepared generally according to the synthetic protocols described generally in Examples A, B and C and more particularly in Examples 11–127. Migration of the last nucleobase methylcarbonyl moiety to the terminal nitrogen is prevented by capping the N-terminus of the PNA chain with a glycine residue. The compounds are purified by HPLC (reverse phase, 0.1% trifluoroacetic acid in acetonitrile/water) and the composition verified by mass spectrometry.

EXAMPLE 2

Binding and Helix Formation of Complementary Antiparallel PNA Strands (FIG. 1)

The circular dichroism spectra of PNA-PNA mixtures were obtained by titrating PNA having sequence H-GTAGATCACT-LysNH2 (PNA formula 1 SEQ ID NO: 1) with PNA having sequence H-AGTGATCTAC-LysNH2 (PNA formula 2 SEQ ID NO: 2). The concentration of PNA formula 1 was held constant (50 μmole/L) and the concentration of PNA formula 2 was increased to provide the following formula 2:formula 1 stoichiometries: 0.25 (Curve C), 0.50 (Curve D), 0.75 (Curve E), 1.00 (Curve F), and 1.25 (Curve G). The hybridizations were performed in a 5 mmol/L sodium phosphate buffer, pH 7.0, at 20° C., after 20 minutes of incubation. The path length was 1 cm. Saturation was obtained at equimolar amounts of the two decamers.

FIG. 2 shows development of negative circular dichroism (at 220 nm) as a function of time after mixing equimolar amounts of PNA formula 1 with PNA formula 2. From top to bottom, the curves correspond to the following temperatures: 5° C., 15° C., 23° C., 32° C., 41° C., and 47° C.

FIG. 3 shows an Arrhenius plot of rates from the CD kinetics. The plot provides the activation energy as $\Delta H=33.9$ kJ/mole (with the approximation that $(k_B T/h)\exp(\Delta S^{\ddagger}/R)$ is constant). The full rate equation is $k=(k_B T/h)\exp(-\Delta H^{\ddagger})\exp(-\Delta S^{\ddagger}/R)$ then gives $\Delta S^{\ddagger}=-173$ J/mole.

EXAMPLE 3

PNA Having Binding Affinity for The HIV-tat Protein as Measured in a Competitive Inhibition Assay Samples of PNAs corresponding to various TAR sequences prepared by the method of Example 1 are incubated with recombinant tat transcription factor (100 μM) for 15 minutes at room temperature at 1, 3, 10, 30, and 100 μM (see, e.g., Cullen, et al., *Cell* 1990, 63, 655.). A competitor, a truncated version of the TAR sequence corresponding to residues 16–45 as a 2'-O-methyl oligonucleotide, is employed as a TAR sequence and is biotinylated at the 3'-O end by procedures generally in accordance with the protocols of application Ser. No. 08/032,852, Combinatorial Oligomer Immunoabsorbant Screening Assay For Transcription Factors And Other Biomolecule Binding, filed Mar. 16, 1993, the entire contents of which are incorporated herein by reference. This TAR sequence is added at 100 nM concentration. The reaction is incubated for 20 minutes and then added to streptavidin-coated microtiter plate wells. After unbound molecules are washed away with phosphate-buffered saline (PBS), 100 μL of 1:500 tat antisera is added to each well and incubated for 2 hours. Protein A/G antisera phosphatase is bound to the tat antibodies and PNPP (p-nitrophenylphosphate) substrate (200 μl) then is added. Color development is measured 2 hours later by reading absorbance at 405 nM on a Titertek Multiscan ELISA plate reader.

EXAMPLE 4

PNA Having Binding Affinity for the C-myc Protein

Myc-c is a nuclear protein involved in cell proliferation, differentiation, and neoplastic disease and binds DNA in a sequence specific manner. See, e.g., Nissen, *Cancer Research* 1986, 46, 6217 and Blackwell, *Science* 1990, 250, 1149. Crude nuclear extracts of myc-c are prepared generally in accordance with Franza, et al., *Nature* 1987, 330, 391, from HL 60 cells stimulated to induce the expression of myc-c.

Phosphorothioate oligonucleotides having the sequences GAT CCC CCC ACC ACG TGG TGC CTG A-B (SEQ ID NO:6) and GAT CTC AGG CAC CAC GTG GTG GGG G-B (SEQ ID NO:7), where B=biotin, are synthesized on an automated DNA synthesizer (Applied Biosystems model 380B) using modified standard phosphoramidite chemistry with oxidation by a 0.2M solution of 3H-1,2-benzodithiole-3-one 1,1-dioxide in acetonitrile for stepwise thiation of phosphite linkages. The thiation cycle wait step is 68 seconds and is followed by the capping step. β-Cyanoethyldiisopropyl phosphoramidites can be purchased from Applied Biosystems (Foster City, Calif.). Bases are deprotected by incubation in methanolic ammonia overnight. Following base deprotection, the oligonucleotides are dried in vacuo. Removal of 2'-hydroxyl t-butyldimethylsilyl protecting groups is effected by incubating the oligonucleotide in 1M tetrabutylammonium fluoride in tetrahydrofuran overnight. The RNA oligonucleotides are further purified on $C_{18}$ Sep-Pak cartridges (Waters, Division of Millipore Corp., Milford, Mass.) and ethanol precipitated. The phosphorothioate oligonucleotides are hybridized to create the double stranded NF-kB binding site.

A series of PNA-PNA duplexes is synthesized and hybridized to give a new series of PNA duplexes corresponding to different length portions of the myc-c binding sequence. Each duplex is incubated in triplicate at concentrations of 1, 3, 10, 30, and 100 μM with the HL-60 extract described above. The myc P=S binding site then is added and the mixtures are incubated and washed with PBS. An antibody directed to the leucine zipper region of the myc protein (Santa Cruz Biotechnology) is added at a 1:1000 dilution. Non-bound molecules are washed away with PBS. Binding of myc to biotinylated c-myc transcription factor is quantitated by adding 100 µl of 1:500 tat antisera to each well for 2 hours. Protein A/G-alkaline phosphatase (Pierce; 1:5000; 100 µl) then is added and any excess is removed by washing with PBS. PNPP substrate (200 µl) then is added. Color development is measured 2 hours later by reading absorbance at 405 nM on a Titertek Multiscan ELISA plate reader.

EXAMPLE 5

PNA Having Binding Affinity for the C-rel Transcription Factor

C-rel has been shown to represent a constituent of the NF-kB site binding transcription factor, which plays a crucial role in the expression of a number of genes including the immunoglobulin k light chain gene, IL-2ra, and MHC. (see, e.g., Gilmore, et al., *Cell* 1986, 62, 791.)

Crude nuclear extracts are prepared as detailed by Franza, et al., *Nature* 1987, 330, 391, from Jurkat cells stimulated 4 hours with 1 µM PHA and 100 nM PMA to induce the expression of rel. The extract is then preabsorbed with 100 µl streptavidin agarose per ml for 10 minutes. This is followed with the addition of poly dI.dC as a nonspecific competitor at a concentration of 100 µg/ml of extract. Nuclear extracts containing the biotinylated NF-kB binding site competitor are prepared as in Example 4, above.

A series of PNA duplexes is synthesized to correspond to various length fragments of the consensus binding sequence of c-rel. NF-kB binding site competitor is added to each duplex and the resulting samples are washed. Antibody directed to rel is added. The amount of rel bound is quantitated by adding 100 µl of 1:500 rel antisera to each well for 2 hours. Protein A/G-alkaline phosphatase (Pierce; 1:5000; 100 µl) the is added and any excess is removed by washing with PBS. PNPP substrate (200 µl) then is added. Color development is measured 2 hours later by reading absorbance at 405 nM on a Titertek Multiscan ELISA plate reader.

EXAMPLE 6

PNA Having Binding Affinity for the AP-1 Transcription Factor

Genes belonging to the fos and jun oncogene families encode nuclear proteins associated with a number of transcriptional complexes, see, e.g., Konig, et al., *EMBO Journal* 1989, 8, 2559. C-jun is a major component of the AP-1 binding site, which was originally shown to regulate tissue plasminogen activator (TPA) induced expression of responsive genes through the TPA response element (TRE). The jun protein forms homo- or heterodimers which bind the TRE. The fos protein is only active as a heterodimer with any of the jun family of proteins. Fos/jun heterodimers have a much higher affinity for the TRE than jun homodimers.

Both the fos and the jun cDNA have been cloned downstream of the Sp6 promoter. RNA is produced from each plasmid in vitro, then used to produce functional jun and fos proteins in rabbit reticulocyte lystates. The fos and jun proteins are then allowed to bind to the biotinylated AP-1 binding site in competition with PNA duplex sequences constructed as mimics of the proper consensus sequence for binding fos and jun, CGC TTG GTG ACT CAG CCG GAA (SEQ ID NO: 8). Binding is quantitated with an antibody directed to fos or jun. When the fos alone is incubated with the AP-1 site there will be no detectable binding with either antibody. When the jun alone is incubated with the binding site, a signal will be detected with only the jun antibody. This is consistent with the formation of a jun homodimer, which has previously been demonstrated to bind AP-1. When the fos and jun proteins are mixed a signal will be detected with both fos and jun antibodies. This is consistent with the formation of a fos/jun homodimer which is known to bind the AP-1 site and should be detectable with either antibody.

PNA sequences of the present invention can be tested for the ability to block the formation of the fos/jun heterodimer. Molecules which block formation will decrease the signal detected with the fos antibody, but not the jun antibody.

EXAMPLE 7

Chimera Macromolecule Having Peptide Nucleic Acids Section Attaching to 3' Terminus of a 2'-Deoxy Phosphorothioate Oligonucleotide Section A first section of peptide nucleic acids is prepared as per PCT patent application WO 92/20702. The peptide nucleic acids are prepared from the C terminus towards the N terminus using monomers having protected amino groups. Following completion of the peptide region, the terminal amine blocking group is removed and the resulting amine reacted with a 3'-C-(formyl)-2', 3'-dideoxy-5'-trityl nucleotide as prepared per the procedure of Vasseur, et. al., *J. Am. Chem. Soc.* 1992, 114, 4006. The condensation of the amine with the aldehyde moiety of the C-formyl nucleoside is effected as per the conditions of the Vasseur, ibid., to yield an intermediate imine linkage. The imine linkage is reduced under reductive the alkylation conditions of Vasseur, ibid., with HCHO/NaBH$_3$CN/AcOH to yield the nucleoside connected to the peptide nucleic acid via an methyl alkylated amine linkage. An internal 2'-deoxy phosphorothioate nucleotide region is then continued from this nucleoside as per standard automatated DNA synthetic protocols (see Oligonucleotide synthesis, a practic approach, M. J. Gait ed, IRL Press, 1984).

EXAMPLE 8

Chimera Macromolecule Having Peptide Nucleic Acids Section Attaching to 5' Terminus of a Phosphorothioate Oligonucleotide Section A phosphorothioate oligonucleotide is prepared in the standard manner on a solid support as per standard protocols (see Oligonucleotides and Analogues, A Practical Approach, F. Eckstein Ed., IRL Press, 1991. The dimethoxytrityl blocking group on that nucleotide is removed in the standard manner. Peptide synthesis for the peptide region is commenced by reaction of the carboxyl end of the first peptide nucleic acid of this region with the 5' hydroxy of the last nucleotide of the DNA region. Coupling is effected via EDC (Pierce) in pyridine to form an ester linkage between the peptide and the nucleoside. Peptide synthesis is then continued in the manner of patent application WO 92/20702 to complete the peptide nucleic acid region.

EXAMPLE 9

Double Stranded Structures that Include Chimera Strand

Duplex structures will be formed with the chimera strands of Examples 7 and 8. Duplex structures can include duplexes between a PNA-RNA or PNA-DNA strand and a RNA strand, a PNA-RNA or PNA-DNA strand and a DNA strand, a PNA-RNA or PNA-DNA strand and a PNA strand or a PNA-RNA or PNA-DNA strand and a further chimeric PNA-DNA or PNA-RNA strand.

EXAMPLE 10

Binding Between PNA Containing Double Stranded Structure and Transcription Factor or Other Protein A double stranded PNA structure, a structure containing PNA chimeric strand and a nucleic acid strand or two PNA chimera strands will be used to bind to or otherwise modulate single stranded DNA, double stranded DNA, RNA, a transcription factor or other protein. In the use of a PNA containing chimera, part of the binding between the chimera and the transcription factor or other protein can include binding between the sugar-phosphate backbone of the DNA or RNA portion of the chimera and hydrogen bonding between the ligands, e.g. nucleobases, of the PNA portion of the chimera. Binding to the sugar-phosphate backbone includes binding to phosphodiester linkages, phosphorothioate linkages or other linkgages that may be used as the backbone of the DNA or RNA. In other instances, bonding can include hydrophobic contacts between hydrophobic groups on the ligands, including nucleobases, of the PNA or the nucleobases of the nucleic acid portion of the chimera with like hydrophobic groups on proteins that are being bound. Such hydrophobic groups on the chimeric strand include the methyl groups on thymine nucleobases.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

EXAMPLE A

Synthesis of PNA Oligomers and Polymers

The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85, 2149 and *Science*, 1986, 232, 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention (FIG. 4).

Concerning the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Ill., 1984). Reactions for the introduction of chloromethyl functionality (Merrifield resin; via a chloromethyl methyl ether/SnCl$_4$ reaction), aminomethyl functionality (via an N-hydroxymethylphthalimide reaction; see, Mitchell, et al., *Tetrahedron Lett.*, 1976, 3795), and benzhydrylamino functionality (Pietta, et al., *J. Chem. Soc.*, 1970, 650) are the most widely applied. Regardless of its nature, the purpose of the functionality is normally to form an anchoring linkage between the copolymer solid support and the C-terminus of the first amino acid to be coupled to the solid support. As will be recognized, anchoring linkages also can be formed between the solid support and the amino acid N-terminus. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention. Preferred methods for PNA synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30, 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid, N-Boc-p-acylbenzhydrylamines such as N-Boc-p-glutaroylbenzhydrylamine, N-Boc-4'-lower alkyl-p-acylbenzhydrylamines such as N-Boc-4'-methyl-p-glutaroylbenzhydrylamine, N-Boc-4'-lower alkoxy-p-acylbenzhydrylamines such as N-Boc-4'-methoxy-p-glutaroyl-benzhydrylamine, and 4-hydroxymethylphenoxyacetic acid. One type of spacer group particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized PNA chain from the solid support such that the C-terminal of the PNA chain is in amide form, require no introduction of a spacer group. Any such functionality may advantageously be employed in the context of the present invention.

An alternative strategy concerning the introduction of spacer or handle groups is the so-called "preformed handle" strategy (see, Tam, et al., *Synthesis*, 1979, 955–957), which offers complete control over coupling of the first amino acid, and excludes the possibility of complications arising from the presence of undesired functional groups not related to the peptide or PNA synthesis. In this strategy, spacer or handle groups, of the same type as described above, are reacted with the first amino acid desired to be bound to the solid support, the amino acid being N-protected and optionally protected at the other side-chains which are not relevant with respect to the growth of the desired PNA chain. Thus, in those cases in which a spacer or handle group is desirable, the first amino acid to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (Tam, et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Suitable choices for N-protection are the tert-butyloxycarbonyl (Boc) group (Carpino, *J. Am. Chem. Soc.,* 1957, 79, 4427; McKay, et al., *J. Am. Chem. Soc.,* 1957, 79, 4686; Anderson, et al., *J. Am. Chem. Soc.,* 1957, 79, 6180) normally in combination with benzyl-based groups for the protection of side chains, and the 9-fluorenylmethyloxycarbonyl (Fmoc) group (Carpino, et al., *J. Am. Chem. Soc.,* 1970, 92, 5748 and *J. Org. Chem.,* 1972, 37, 3404), normally in combination with tert-butyl (tBu) for the protection of any side chains, although a number of other possibilities exist which are well known in conventional solid-phase peptide synthesis. Thus, a wide range of other useful amino protecting groups exist, some of which are Adoc (Hass, et al., *J. Am. Chem. Soc.,* 1966, 88, 1988), Bpoc (Sieber, *Helv. Chem. Acta.,* 1968, 51, 614), Mcb (Brady, et al., *J. Org. Chem.,* 1977, 42, 143), Bic (Kemp, et al., *Tetrahedron,* 1975, 4624), the o-nitrophenylsulfenyl (Nps) (Zervas, et al., *J. Am. Chem. Soc.,* 1963, 85, 3660), and the dithiasuccinoyl (Dts) (Barany, et al., *J. Am. Chem. Soc.,* 1977, 99, 7363). These amino protecting groups, particularly those based on the widely-used urethane functionality, successfully prohibit racemization (mediated by tautomerization of the readily formed oxazolinone (azlactone) intermediates (Goodman, et al., *J. Am. Chem. Soc.,* 1964, 86, 2918)) during the coupling of most α-amino acids. In addition to such amino protecting groups, a whole range of otherwise "worthless" nonurethane-type of amino protecting groups are applicable when assembling PNA molecules, especially those built from achiral units. Thus, not only the above-mentioned amino protecting groups (or those derived from any of these groups) are useful within the context of the present invention, but virtually any amino protecting group which largely fulfills the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids). Additionally: (4) the protecting group must be close to quantitatively removable, without serious side reactions, and (5) the optical integrity, if any, of the incoming amino acid should preferably be highly preserved upon coupling. Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach), Following coupling of the first amino acid, the next stage of solid-phase synthesis is the systematic elaboration of the desired PNA chain. This elaboration involves repeated deprotection/coupling cycles. The temporary protecting group, such as a Boc or Fmoc group, on the last-coupled amino acid is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, it can be bound by providing the incoming amino acid in a form with the carboxyl group activated by any of several methods, including the initial formation of an active ester derivative such as a 2,4,5-trichlorophenyl ester (Pless, et al., *Helv. Chim. Acta,* 1963, 46, 1609), a phthalimido ester (Nefkens, et al., *J. Am. Chem. Soc.,* 1961, 83, 1263), a pentachlorophenyl ester (Kupryszewski, *Rocz. Chem.,* 1961, 35, 595), a pentafluorophenyl ester (Kovacs, et al., *J. Am. Chem. Soc.,* 1963, 85, 183), an o-nitrophenyl ester (Bodanzsky, *Nature,* 1955, 175, 685), an imidazole ester (Li, et al., *J. Am. Chem. Soc.,* 1970, 92, 7608), and a 3-hydroxy-4-oxo-3,4-dihydroquinazoline (Dhbt-OH) ester (Konig, et al., *Chem. Ber.,* 1973, 103, 2024 and 2034), or the initial formation of an anhydride such as a symmetrical anhydride (Wieland, et al., *Angew. Chem., Int. Ed. Engl.,* 1971, 10, 336). Alternatively, the carboxyl group of the incoming amino acid can be reacted directly with the N-terminal of the last-coupled amino acid with the assistance of a condensation reagent such as, for example, dicyclohexylcarbodiimide (Sheehan, et al., *J. Am. Chem. Soc.,* 1955, 77, 1067) or derivatives thereof. Benzotriazolyl N-oxy-trisdimethylaminophosphonium hexafluorophosphate (BOP), "Castro's reagent" (see, e.g., Rivaille, et al., *Tetrahedron,* 1980, 36, 3413) is recommended when assembling PNA molecules containing secondary amino groups. Finally, activated PNA monomers analogous to the recently-reported amino acid fluorides (Carpino, *J. Am. Chem. Soc.,* 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

In the above-mentioned "Boc-benzyl" protection scheme, the final deprotection of side-chains and release of the PNA molecule from the solid support is most often carried out by the use of strong acids such as anhydrous HF (Sakakibara, et al., *Bull. Chem. Soc. Jpn.,* 1965, 38, 4921), boron tris (trifluoroacetate) (Pless, et al., *Helv. Chim. Acta,* 1973, 46, 1609), and sulfonic acids such as trifluoromethanesulfonic acid and methanesulfonic acid (Yajima, et al., *J. Chem. Soc., Chem. Comm.,* 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol and, therefore, the sulfide-assisted acidolytic $S_N2$ deprotection method (Tam, et al., *J. Am. Chem. Soc.,* 1983, 105, 6442 and *J. Am. Chem. Soc.,* 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.,* 1973, 95, 4501), and ammonolysis as well as hydrazinolysis (Bodanszky, et al., *Chem. Ind.,* 1964 1423), hydrogenolysis (Jones, *Tetrahedron Lett.* 1977 2853 and Schlatter, et al., *Tetrahedron Lett.* 1977 2861)), and photolysis (Rich and Gurwara, *J. Am. Chem. Soc.,* 1975 97, 1575)).

Finally, in contrast with the chemical synthesis of "normal" peptides, stepwise chain building of achiral PNAs such as those based on aminoethylglycyl backbone units can start either from the N-terminus or the C-terminus, because the coupling reactions are free of racemization. Those skilled in the art will recognize that whereas syntheses commencing at the C-terminus typically employ protected amine groups and free or activated acid groups, syntheses commencing at the N-terminus typically employ protected acid groups and free or activated amine groups.

Based on the recognition that most operations are identical in the synthetic cycles of solid-phase peptide synthesis (as is also the case for solid-phase PNA synthesis), a new matrix, PEPS, was recently introduced (Berg, et al., *J. Am. Chem. Soc.,* 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple PNA molecules, these being conceptually simple to synthesize since only four different reaction compartments are normally required, one for each of the four "pseudo-nucleotide" units. Thus, the PEPS film support has been successfully tested in a number of PNA syntheses carried out in a parallel and substantially simultaneous fashion. The yield and quality of the products obtained from PEPS were comparable to those obtained by using the traditional polystyrene beaded support. Also, experiments with other geometries of the PEPS polymer such as, for example, non-woven felt, knitted net, sticks or microwellplates have not indicated any limitations of the synthetic efficacy.

Two other methods proposed for the simultaneous synthesis of large numbers of peptides also apply to the preparation of multiple, different PNA molecules. The first of these methods (Geysen, et al., *Proc. Natl. Acad. Sci. USA,* 1984, 81, 3998) utilizes acrylic acid-grafted polyethylenerods and 96-microtiter wells to immobilize the growing peptide chains and to perform the compartmentalized synthesis. While highly effective, the method is only applicable on a microgram scale. The second method (Houghten, *Proc. Natl. Acad. Sci. USA,* 1985, 82, 5131) utilizes a "tea bag" containing traditionally-used polymer beads. Other relevant proposals for multiple peptide or PNA synthesis in the context of the present invention include the simultaneous use of two different supports with different densities (Tregear, in "*Chemistry and Biology of Peptides*", J. Meienhofer, ed., Ann Arbor Sci. Publ., Ann Arbor, 1972 pp. 175–178), combining of reaction vessels via a manifold (Gorman, *Anal. Biochem.,* 1984, 136, 397), multicolumn solid-phase synthesis (e.g. Krchnak, et al., *Int. J. Peptide Protein Res.,* 1989, 33, 209), and Holm and Meldal, in "*Proceedings of the 20th European Peptide Symposium*", G. Jung and E. Bayer, eds., Walter de Gruyter & Co., Berlin, 1989 pp. 208–210), and the use of cellulose paper (Eichler, et al., *Collect. Czech. Chem. Commun.,* 1989, 54, 1746).

While the conventional cross-linked styrene/divinylbenzene copolymer matrix and the PEPS support are presently preferred in the context of solid-phase PNA synthesis, a non-limiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.,* 1975, 97, 6584, *Bioorg. Chem.* 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.,* 1970, 4503); (3) a third general type of useful solid supports can be termed composites in that they contain two major ingredients: a resin and another material that is also substantially inert to the organic synthesis reaction conditions employed. One exemplary composite (see Scott, et al., *J. Chrom. Sci.,* 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243) and van Rietschoten in "*Peptides* 1974", Y. Wolman, Ed., Wiley and Sons, New York, 1975, pp. 113–116); and (4) contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345), are suited for PNA synthesis as well.

Whether manually or automatically operated, solid-phase PNA synthesis in the context of the present invention is normally performed batchwise. However, most of the syntheses may equally well be carried out in the continuous-flow mode, where the support is packed into columns (Bayer, et al., *Tetrahedron Lett.*, 1970, 4503 and Scott, et al., *J. Chromatogr. Sci.*, 1971, 9, 577). With respect to continuous-flow solid-phase synthesis, the rigid poly (dimethylacrylamide)-Kieselguhr support (Atherton, et al., *J. Chem. Soc. Chem. Commun.*, 1981, 1151) appears to be particularly successful, but another valuable configuration concerns the one worked out for the standard copoly (styrene-1%-divinylbenzene) support (Krchnak, et al., *Tetrahedron Lett.*, 1987, 4469).

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, "*Principles of Peptide Synthesis*", Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., *Tetrahedron Lett.*, 1965, 2323) and polyethylene glycol (PEG) (Mutter and Bayer, *Angew. Chem., Int. Ed. Engl.*, 1974, 13, 88), is useful; (3) random polymerization (see, e.g., Odian, "*Principles of Polymerization*", McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., *J. Am. Chem. Soc.*, 1965, 87, 4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA molecules; (6) since antibodies can be generated to virtually any molecule of interest, the recently developed catalytic antibodies (abzymes), discovered simultaneously by the groups of Lerner (Tramantano, et al., *Science*, 1986, 234, 1566) and of Schultz (Pollack, et al., *Science*, 1986, 234, 1570), should also be considered as potential candidates for assembling PNA molecules. Thus, there has been considerable success in producing abzymes catalyzing acyl-transfer reactions (see for example Shokat, et al., *Nature*, 1989, 338, 269) and references therein). Finally, completely artificial enzymes, very recently pioneered by Stewart's group (Hahn, et al., *Science*, 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty natural by occurring (proteinogenic) amino acids constituting peptides. In conclusion, no single strategy may be wholly suitable for the synthesis of a specific PNA molecule, and therefore, sometimes a combination of methods may work best.

EXAMPLE B

Synthesis of Monomeric Building Blocks

The monomers preferably are synthesized by the general scheme outlined in FIG. 5. This involves preparation of either the methyl or ethyl ester of (Bocaminoethyl)glycine, by a protection/deprotection procedure as described in Examples 34–36. The synthesis of thymine monomer is described in Examples 37–38, and that of the protected cytosine monomer is described in Example 39.

The synthesis of the protected adenine monomer (FIG. 6) involved alkylation with ethyl bromoacetate (Example 40) and verification of the position of substitution by X-ray crystallography, as being the wanted 9-position. The $N^6$-amino group then was protected with the benzyloxycarbonyl group by the use of the reagent N-ethyl-benzyloxycarbonylimidazole tetrafluoroborate (Example 41). Simple hydrolysis of the product ester (Example 42) gave $N^6$-benzyloxycarbonyl-9-carboxymethyl adenine, which then was used in the standard procedure (Examples 43–44, FIG. 5). The adenine monomer has been built into two different PNA-oligomers (Examples 66, 67, 81 and 83).

The synthesis of the protected G-monomer is outlined in FIG. 7. The starting material, 2-amino-6-chloropurine, was alkylated with bromoacetic acid (Example 45) and the chlorine atom was then substituted with a benzyloxy group (Example 46). The resulting acid was coupled to the (bocaminoethyl) glycine methyl ester (from Example 46) with agent PyBrop™, and the resulting ester was hydrolysed (Example 47). The $O^6$-benzyl group was removed in the final HF-cleavage step in the synthesis of the PNA-oligomer. Cleavage was verified by finding the expected mass of the final PNA-oligomer, upon incorporation into an PNA-oligomer using diisopropyl carbodiimide as the condensation agent (Examples 65 and 81).

EXAMPLE C

Extended Backbones

Alterations of the groups A, C and D (FIG. 16) is demonstrated by the synthesis of monomeric building blocks and incorporation into PNA-oligomers.

In one example, the C group was a $CH(CH_3)$ group. The synthesis of the corresponding monomer is outlined in FIG. 8. It involves preparation of Boc-protected 1-amino-2,3-propanediol (Example 48), which is cleaved by periodate to give bocaminoacetaldehyde, which is used directly in the next reaction. The bocaminoacetaldehyde can be condensed with a variety of amines; in Example 49, alanine ethyl ester was used. In Examples 50–52, the corresponding thymine monomers were prepared. The monomer has been incorporated into an 8-mer (Example 70) by the DCC-coupling protocol (Examples 66 and 67).

In another example, the D group is a $(CH_2)_3$ group. The synthesis of the corresponding monomer is outlined in FIG. 18.A and described in Examples 53–54.

In another example, the A group is a $(CH_2)_2CO$ group. The synthesis of the corresponding thymine monomer is outlined FIG. 18.B and Examples 56 through 58.

In yet another example, the C group is a $(CH_2)_2$ group. The synthesis of the thymine and protected cytosine monomer is outlined in FIG. 9 and Examples 59 through 64. Hybridization experiments with a PNA-oligomer containing one unit is described in Examples 71 and 91, which shows a significant lowering of affinity but a retention of specificity.

GENERAL REMARKS

The following abbreviations are used in the experimental examples: DMF, N,N-dimethylformamide; DCC, N,N-dicyclohexyl carbodiimide; DCU, N,N-dicyclohexyl urea; THF, tetrahydrofuran; aeg, N-acetyl (2'-aminoethyl)glycine; pfp, pentafluorophenyl; Boc, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift;

NMR spectra were recorded on either a JEOL FX 90Q spectrometer, or a Bruker 250 MHz with tetramethylsilane as internal standard. Mass spectrometry was performed on a MassLab VG 12-250 quadropole instrument fitted with a VG FAB source and probe. Melting points were recorded on Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled before use. Dioxane was passed through basic alumina prior to use. Bocanhydride, 4-nitrophenol, methyl bromoacetate, benzyloxycarbonyl chloride, pentafluorophenol were all obtained through Aldrich Chemical Company. Thymine, cytosine, adenine were all obtained through Sigma.

Thin layer chromatography (Tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) or/and spraying with a ninhydrin solution (3 g ninhydrin in 1000 ml 1-butanol and 30 ml acetic acid), after heating at 120° C. for 5 min and, after spraying, heating again.

EXAMPLE 11 tert-Butyl 4-nitrophenyl carbonate

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was refluxed for 1 h, cooled to 0° C., filtered and concentrated to ⅓, and then poured into water (350 ml) at 0° C. After stirring for ½ h., the product was collected by filtration, washed with water, and then dried over sicapent, in vacuo. Yield 21.3 g (97%). M.p. 73.0–74.5° C. (litt. 78.5–79.5° C.). Anal. for $C_{11}H_{13}NO_5$ found(calc.) C: 55.20(55.23) H: 5.61(5.48) N: 5.82(5.85).

EXAMPLE 12

(N'-Boc-2'-aminoethyl) glycine (2)

The title compound was prepared by a modification of the procedure by Heimer, et al. *Int. J. Pept.*, 1984, 23, 203–211 N-(2-Aminoethyl)glycine (1, 3.00 g; 25.4 mmol) was dissolved in water (50 ml), dioxane (50 ml) was added, and the pH was adjusted to 11.2 with 2 N sodium hydroxide. tert-Butyl-4-nitrophenyl carbonate (7.29 g; 30.5 mmol) was dissolved in dioxane (40 ml) and added dropwise over a period of 2 h, during which time the pH was maintained at 11.2 with 2 N sodium hydroxide. The pH was adjusted periodically to 11.2 for three more hours and then the solution was left overnight. The solution was cooled to 0° C. and the pH was carefully adjusted to 3.5 with 0.5 M hydrochloric acid. The aqueous solution was washed with chloroform (3×200 ml), the pH adjusted to 9.5 with 2N sodium hydroxide and the solution was evaporated to dryness, in vacuo (14 mmHg). The residue was extracted with DMF (25+2×10 ml) and the extracts filtered to remove excess salt. This results in a solution of the title compound in about 60% yield and greater than 95% purity by tlc (system 1 and visualised with ninhydrin, Rf=0.3). The solution was used in the following preparations of Boc-aeg derivates without further purification.

EXAMPLE 13

N-1-Carboxymethylthymine (4)

This procedure is different from the literature synthesis, but is easier, gives higher yields, and leaves no unreacted thymine in the product. To a suspension of thymine (3, 40.0 g; 0.317 mol) and potassium carbonate (87.7 g; 0.634 mmol) in DMF (900 ml) was added methyl bromoacetate (30.00 ml; 0.317 mmol). The mixture was stirred vigorously overnight under nitrogen. The mixture was filtered and evaporated to dryness, in vacuo. The solid residue was treated with water (300 ml) and 4 N hydrochloric acid (12 ml), stirred for 15 min at 0° C., filtered, and washed with water (2×75 ml). The precipitate was treated with water (120 ml) and 2N sodium hydroxide (60 ml), and was boiled for 10 minutes. The mixture was cooled to 0° C., filtered, and the pure title compound was precipitated by the addition of 4 N hydrochloric acid (70 ml). Yield after drying, in vacuo over sicapent: 37.1 g (64%). $^1$H-NMR: (90 MHz; DMSO-$d_6$): 11.33 ppm (s,1H,N$\underline{H}$); 7.49(d,J=0.92 Hz,1H,Ar$\underline{H}$); 4.38 (s,2H,C$\underline{H}_2$); 1.76 (d,J=0.92 Hz,T-C$\underline{H}_3$)

EXAMPLE 14

N-1-Carboxymethylthymine pentafluorophenyl ester (5)

N-1-Carboxymethylthymine (4, 10.0 g; 54.3 mmol) and pentafluorophenol (10.0 g; 54.3 mmol) were dissolved in DMF (100 ml) and cooled to 5° C. in ice water. DCC (13.45 g; 65.2 mmol) then was added. When the temperature passed below 5° C., the ice bath was removed and the mixture was stirred for 3 h at ambient temperature. The precipitated DCU was removed by filtration and washed twice with DMF (2×10 ml). The combined filtrate was poured into ether (1400 ml) and cooled to 0° C. Petroleum ether (1400 ml) was added and the mixture was left overnight. The title compound was isolated by filtration and was washed thoroughly with petroleum ether. Yield: 14.8 g (78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C: 44.79(44.59); H: 2.14(2.01) N: 8.13(8.00). FAB-MS: 443 (M+1+glycerol), 351 (M+1). $^1$H-NMR (90 MHz; DMS-$d_6$): 11.52 ppm (s,1H,N$\underline{H}$) ; 7.64 (s,1H,Ar$\underline{H}$); 4.99 (s,2H, C$\underline{H}_2$); 1.76 (s,3H,C$\underline{H}_3$).

EXAMPLE 15

1-(Boc-aeg)thymine (6)

To the DMF-solution from above was added triethyl amine (7.08 ml; 50.8 mmol) followed by N-1-carboxymethylthymine pentafluorophenyl ester (5, 4.45 g; 12.7 mmol). The resultant solution was stirred for 1 h. The solution was cooled to 0° C. and treated with cation exchange material ("Dowex 50W X-8", 40 g) for 20 min. The cation exchange material was removed by filtration, washed with dichloromethane (2×15 ml), and dichloromethane (150 ml) was added. The resulting solution was washed with saturated sodium chloride, dried over magnesium sulfate, and evaporated to dryness, in vacuo, first by a water aspirator and then by an oil pump. The residue was shaken with water (50 ml) and evaporated to dryness. This procedure was repeated once. The residue then was dissolved in methanol (75 ml) and poured into ether (600 ml) and petroleum ether (1.4 L). After stirring overnight, the white solid was isolated by filtration and was washed with petroleum ether. Drying over sicapent, in vacuo, gave 3.50 g (71.7%). M.p. 142–147° C. Anal. for $C_{16}H_{24}N_4O_7$. Found (calc.) C: 49.59(50.00) H: 6.34(6.29) N: 14.58(14.58). $^1$H-NMR (250 MHz, DMSO-$d_6$): Due to the limited rotation around the secondary amide bond several of the signals were doubled in the ratio 2:1,(indicated in the list by mj. for major and mi. for minor). 12.73 ppm (b,1H, —$CO_2$H); 11.27 ppm (s, mj., imide); 11.25 ppm (s, mi., imide); 7.30 ppm (s, mj., ArH); 7.26 ppm (s, mi., ArH); 6.92 ppm (unres. t, mj., BocNH); 6.73 ppm (unres. t; mi., BocNH); 4.64 ppm (s, mj., T—$CH_2$—CO—); 4.47 ppm (s, mi., T—$CH_2$—CO—); 4.19 ppm (s, mi., CONRC$\underline{H}_2CO_2H$); 3.97 ppm (s, mj., CONRC$\underline{H}_2CO_2H$); 3.41–2.89 ppm (unres. m, —$CH_2CH_2$— and water); 1.75 ppm (s,3H, T—$CH_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C5"); 141.92 (C6"); 108.04 (C2'); 77.95 and 77.68 (Thy-C$\underline{H}_2$CO); 48.96, 47.45 and 46.70 (—$\underline{C}H_2CH_2$— and NC$\underline{H}_2CO_2H$); 37.98 (Thy-C$\underline{H}_3$); 28.07 (t-Bu). FAB-MS: 407 (M+Na$^+$); 385 (M+H$^+$).

EXAMPLE 16

1-(Boc-aeg)thymine pentafluorophenyl ester (7, Boc-Ta-eg.OPfp)

1-(Boc-aeg)thymine (6) (2.00 g; 5.20 mmol) was dissolved in DMF (5 ml) and methylene chloride (15 ml) was added. Pentafluorophenol (1.05 g; 5.72 mmol) was added and the solution was cooled to 0° C. in an ice bath. DDC then was added (1.29 g; 6.24 mmol) and the ice bath was removed after 2 min. After 3 h with stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 ml) and poured into water (200 ml) at 0° C. The title compound was isolated by filtration, washed with water, and dried over sicapent, in vacuo. Yield: 2.20 g (77%). An analytical sample was obtained by recrystallisation from 2-propanol. M.p. 174–175.5° C. Analysis for $C_{22}H_{23}N_4O_7F_5$, found(calc.): C: 48.22(48.01); H: 4.64(4.21); N: 9.67(10.18). $^1$H-NMR (250 MHz, CDCl$_3$): Due to the limited rotation around the secondary amide bond several of the signals were doubled in the ratio 6:1 (indicated in the list by mj. for major and mi. for minor). 7.01 ppm (s, mi., ArH); 6.99 ppm (s, mj., ArH); 5.27 ppm (unres. t, BocN$\underline{H}$); 4.67 ppm (s, mj., T—$CH_2$—CO—); 4.60 ppm (s, mi., T—$CH_2$—CO—); 4.45 ppm (s, mj., CONRC$\underline{H}_2CO_2$Pfp); 4.42 ppm (s, mi., CONRC$\underline{H}_2CO_2$Pfp); 3.64 ppm (t,2H,BocNHC$H_2$C$\underline{H}_2$—); 3.87 ppm ("q",2H,BocNHC$\underline{H}_2CH_2$—); 1.44(s,9H,t-Bu). FAB-MS: 551 (10; M+1); 495 (10; M+1-tBu); 451 (80; -Boc).

EXAMPLE 17

$N^4$-Benzyloxycarbonyl cytosine (9)

Over a period of about 1 h, benzyloxycarbonyl chloride (52 ml; 0.36 mol) was added dropwise to a suspension of cytosine (8, 20.0 g;0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH ~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo. Yield 24.7 g (54%). M.p.>250° C. Anal. for $C_{12}H_{11}N_3O_3$. Found(calc.); C: 58.59(58.77); H: 4.55 (4.52); N: 17.17(17.13). No NMR spectra were recorded since it was not possible to get the product dissolved.

EXAMPLE 18

$N^4$-Benzyloxycarbonyl-$N^1$-carboxymethyl cytosine (10)

In a three necked round bottomed flask equipped with mechanical stirring and nitrogen coverage was placed methyl bromacetate (7.82 ml;82.6 mmol) and a suspension of $N^4$-benzyloxycarbonyl-cytosine (9, 21.0 g; 82.6 mmol) and potassium carbonate (11.4 g; 82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal. for $C_{14}H_{13}N_3O_5$. Found(calc.); C: 55.41 (55.45); H: 4.23(4.32); N: 14.04(13.86). $^1$H-NMR (90 MHz; DMSO-$d_6$): 8.02 ppm (d,J=7.32 Hz,1H,H-6); 7.39 (s,5H, Ph) 7.01 (d,J=7.32 Hz,1H, H-5); 5.19 (s,2H,PhC$\underline{H}_2$—); 4.52 (s,2H).

EXAMPLE 19

$N^4$-Benzyloxycarbonyl-$N^1$-carboxymethyl-cytosine pentafluorophenyl ester (11)

$N^4$-Benzyloxycarbonyl-N-carboxymethyl-cytosine (10, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for $C_{20}H_{12}N_3F_5O_5$. Found(calc.); C: 51.56(51.18); H: 2.77(2.58); N: 9.24(8.95).$^1$H-NMR (90 MHz; CDCl$_3$): 7.66 ppm (d,J=7.63 Hz,1H,H-6); 7.37 (s,5H,Ph); 7.31 (d,J=7.63 Hz,1H,H-5); 5.21 (s,2H,PhC$\underline{H}_2$—); 4.97 (s,2H,NC$\underline{H}_2$—). FAB-MS: 470 (M+1)

EXAMPLE 20

$N^4$-Benzyloxycarbonyl-1-Boc-aeg-cytosine (12)

To a solution of (N-Boc-2-aminoethyl)glycine (2) in DMF, prepared as described above, was added triethyl amine (7.00 ml; 50.8 mmol) and $N^4$-benzyloxycarbonyl-$N^1$-carboxymethyl-cytosine pentafluorophenyl ester (11, 2.70 g; 5.75 mmol). After stirring the solution for 1 h at room temperature, methylene chloride (150 ml), saturated sodium chloride (250 ml), and 4 N hydrochloric acid to pH ~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C. (decomp.). $^1$H-NMR (250 MHz, $CDCl_3$): Due to the limited rotation around the secondary amide bond several of the signals were doubled in the ratio 2:1, (indicated in the list by mj. for major and mi. for minor). 7.88 ppm (dd,1H,H-6); 7.39 (m,5H,Ph); 7.00 (dd,1H,H-5); 6.92 (b,1H,BocN$\underline{H}$); 6.74 (b,1H,ZN$\underline{H}$)-?; 5.19 (s,2H,Ph—C$\underline{H}_2$); 4.81 ppm (s, mj., Cyt—$CH_2$—CO—); 4.62 ppm (s, mi., Cyt—$CH_2$—CO—); 4.23 (s, mi., CONRC$\underline{H}_2CO_2$H); 3.98 ppm (s, mj., CONRC$\underline{H}_2CO_2$H); 3.42–3.02 (unres. m, —$CH_2CH_2$— and water); 1.37 (s,9H,tBu). FAB-MS: 504 (M+1); 448 (M+1-tBu).

EXAMPLE 21

$N^4$-Benzyloxycarbonyl-1-Boc-aeg-cytosine pentafluorophenyl ester (13)

$N^4$-Benzyloxycarbonyl-1-Boc-aeg-cytosine (12, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over sicapent, in vacuo. Yield 1.30 g (65%). Analysis for $C_{29}H_{28}N_5O_8F_5$. Found(calc.); C: 52.63(52.02); H: 4.41(4. 22); N: 10.55(10.46). $^1$H-NMR (250 MHz; DMSO-$d_6$): showed essentially the spectrum of the above acid, most probably due to hydrolysis of the ester. FAB-MS: 670 (M+1); 614 (M+1-tBu)

EXAMPLE 22

4-Chlorocarboxy-9-chloroacridine

4-Carboxyacridone (6.25 g; 26.1 mmol), thionyl chloride (25 ml), and 4 drops af DMF were heated gently under a flow of nitrogen until all solid material had dissolved. The solution then was refluxed for 40 min. The solution was cooled and excess thionyl chloride was removed in vacuo. The last traces of thionyl chloride were removed by coevaporation with dry benzene (dried over Na—Pb) twice. The remaining yellow powder was used directly in the next reaction.

EXAMPLE 23

4-(5-Methoxycarbonylpentylamidocarbonyl)-9-chloroacridine

Methyl 6-aminohexanoate hydrochloride (4.70 g; 25.9 mmol) was dissolved in methylene chloride (90 ml), cooled to 0° C., triethyl amine (15 ml) was added, and the resulting solution then was immediately added to the acid chloride from above. The roundbottomed flask containing the acid chloride was cooled to 0° C. in an ice bath. The mixture was stirred vigorously for 30 min at 0° C. and 3 h at room temperature. The resulting mixture was filtered to remove the remaining solids, which were washed with methylene chloride (20 ml). The red-brown methylene chloride filtrate was subsequently washed twice with saturated sodium hydrogen carbonate, once with saturated sodium chloride, dried over magnesium sulfate, and evaporated to dryness, in vacuo. To the resulting oily substance was added dry benzene (35 ml) and ligroin (60–80° C., dried over Na—Pb). The mixture was heated to reflux. Activated carbon and celite were added and mixture was refluxed for 3 min. After filtration, the title compound crystallised upon cooling with magnetic stirring. It was isolated by filtration and washed with petroleum ether. The product was stored over solid potassium hydroxide. Yield 5.0 g (50%).

EXAMPLE 24

4-(5-Methoxycarbonylpentyl)amidocarbonyl-9-[6'-(4"-nitrobenzamido)hexylamino]-aminoacridine 4-(5-Methoxycarbonylpentylamidocarbonyl)-9-chloroacridine (1.30 g; 3.38 mmol) and phenol (5 g) were heated to 80° C. for 30 min under a flow of nitrogen, after which 6-(4'-nitrobenzamido)-1-hexylamine (897 mg; 3.38 mmol) was added. The temperature raised to 120° C. for 2 h. The reaction mixture was cooled and methylene chloride (80 ml) was added. The resulting solution was washed three times with 2N sodium hydroxide (60 ml portions) and once with water, dried over magnesium sulfate, and evaporated to dryness, in vacuo. The resulting red oil (1.8 g) was dissolved in methylene chloride (40 ml), cooled to 0° C. Ether (120 ml) was added and the resultant solution was stirred overnight. This results in a mixture of solid material and an oil. The solid was isolated by filtration. The solid and the oil were re-dissolved in methylene chloride (80 ml) and added dropwise to cold ether (150 ml). After 20 minutes of stirring, the title compound was isolated by filtration in the form of orange crystals. The product was washed with ether and dried in vacuo over potassium hydroxide. Yield 1.60 g (77%). M.p. 145–147° C.

EXAMPLE 25

4-(5-Carboxypentyl)amidocarbonyl-9-[6'-(4"-nitrobenzamido)hexylamino]-aminoacridine 4-(5-Methoxycarbonylpentyl)amidocarbonyl-9-[6'-(4"-nitrobenzamido)hexylamino]aminoacridine (503 mg; 0.82 mmol) was dissolved in DMF (30 ml), and 2 N sodium hydroxide (30 ml) was added. After stirring for 15 min, 2 N hydrochloric acid (35 ml) and water (50 ml) were added at 0° C. After stirring for 30 min, the solution was decanted, leaving an oily substance which was dissolved in boiling methanol (150 ml), filtered and concentrated to ⅓ volume. To the methanol solution were added ether (125 ml) and 5–6 drops of HCl in ethanol. The solution was decanted after 1 h of stirring at 0° C. The oily substance was redissolved in methanol (25 ml) and precipitated with ether (150 ml). The title compound was isolated as yellow crystals after stirring overnight. Yield 417 mg (80%). M.p. 173° C. (decomp.).

EXAMPLE 26

(a) 4-(5-pentafluorophenyloxycarbonylpentyl) amidocarbonyl-9-[6-(4"-nitrobenzamido)hexylamino]-aminoacridine (Acr$^1$Opfp)

The acid from above (300 mg; 0.480 mmol) was dissolved in DMF (2 ml) and methylene chloride (8 ml) was added. Pentafluorophenol (97 mg; 0.53 mmol), transferred with 2×2 ml of the methylene chloride, was added. The resulting solution was cooled to 0° C. after which DCC (124 mg; 0.60 mmol) was subsequently added. The ice bath was removed after 5 minutes and the mixture was left with stirring overnight. The precipitated DCU was removed by centrifugation and the centrifugate was evaporated to dryness, in vacuo, first by a water aspirator and then by an oil pump. The residue was dissolved in methylene chloride (20 ml), filtered, and evaporated to dryness, in vacuo. The residue was again dissolved in methylene chloride and petroleum ether (150 ml). A 1 ml portion of 5M HCl in ether was added. The solvent was removed by decanting after 30 min of stirring at 0° C. The residual oily substance was dissolved in methylene chloride (100 ml). Petroleum ether (150 ml) was added and the mixture was left with stirring overnight. The next day the yellow precipitated crystalline material was isolated by filtration and was washed with copious amounts of petroleum ether. Yield, after drying, 300 mg (78%). M.p. 97.5° C. (decomp.) All samples showed satisfactory elemental analysis, $^1$H- and $^{13}$C-NMR and mass spectra.

(b) Experimental for the Synthesis of PNA Compounds, cf. FIG. 4

Materials: Boc-Lys (ClZ), benzhydrylamine-copoly (styrene-1%-divinylbenzene) resin (BHA resin), and p-methylbenzhydrylamine-copoly(styrene-1%-divinylbenzene) resin (MBHA resin) were purchased from Peninsula Laboratories. Other reagents and solvents were: Biograde trifluoroacetic acid from Halocarbon Products; diisopropylethylamine (99%; was not further distilled) and N-acetylimidazole (98%) from Aldrich; H$_2$O was distilled twice; anhydrous HF from Union Carbide; synthesis grade N,N-dimethylformamide and analytical grade methylene chloride (was not further distilled) from Merck; HPLC grade acetonitrile from Lab-Scan; purum grade anisole, N,N'-dicyclohexylcarbodiimide, and puriss. grade 2,2,2-trifluoroethanol from Fluka.

(c) General Methods and Remarks

Except where otherwise stated, the following applies. The PNA compounds were synthezised by the stepwise solid-phase approach (Merrifield, *J. Am. Chem. Soc.,* 1963, 85, 2149) employing conventional peptide chemistry utilizing the TFA-labile tert-butyloxycarbonyl (Boc) group for "temporary" N-protection (Merrifield, *J. Am. Chem. Soc.,* 1964, 86, 304) and the more acid-stable benzyloxycarbonyl (Z) and 2-chlorobenzyloxycarbonyl (ClZ) groups for "permanent" side chain protection. To obtain C-terminal amides, the PNAs were assembled onto the HF-labile BHA or MBHA resins (the MBHA resin has increased susceptibility to the final HF cleavage relative to the unsubstituted BHA resin (Matsueda, et al., *Peptides,* 1981, 2, 45). All reactions (except HF reactions) were carried out in manually operated standard solid-phase reaction vessels fitted with a coarse glass frit (Merrifield, et al., *Biochemistry,* 1982, 21, 5020). The quantitative ninhydrin reaction (Kaiser test), originally developed by Merrifield and co-workers (Sarin, et al., *Anal. Biochem.,* 1981, 117, 147) for peptides containing "normal" amino acids, was successfully applied (see Table I–III) using the "normally" employed effective extinction coefficient $\epsilon$=15000 M$^{-1}$cm$^{-1}$ for all residues to determine the completeness of the individual couplings as well as to measure the number of growing peptide chains. The theoretical substitution $S_{n-1}$ upon coupling of residue number n (assuming both complete deprotection and coupling as well as neither chain termination nor loss of PNA chains during the synthetic cycle) is calculated from the equation:

$$S_n = S_{n-1} \times (1 + (S_{n-1} \times \Delta MW \times 10^{-3} mmol/mol))^{-1}$$

where $\Delta MW$ is the gain in molecular weight ([$\Delta MW$]=g/mol) and $S_{n-1}$ is the theoretical substitution upon coupling of the preceding residue n–1 ([S]=mmol/g). The estimated value (%) on the extent of an individual coupling is calculated relative to the measured substitution (unless S was not determined) and include correction for the number of remaining free amino groups following the previous cycle. HF reactions were carried out in a Diaflon HF apparatus from Toho Kasei (Osaka, Japan). Vydac C$_{18}$ (5 μm, 0.46×25 cm and 5 μm, 1.0×25 cm) reverse-phase columns, respectively were used for analytical and semi-preparative HPLC on an SP8000 instrument. Buffer A was 5 vol % acetonitrile in water containing 445 μl trifluoroacetic acid per liter, and buffer B was 60 vol % acetonitrile in water containing 390 μl trifluoroacetic acid per liter. The linear gradient was 0–100% of buffer B in 30 min, flow rates 1.2 ml/min (analytical) and 5 ml/min (semi-preparative). The eluents were monitored at 215 nm (analytical) and 230 nm (semi-preparative). Molecular weights of the PNAs were determined by $^{252}$Cf plasma desorption time-of-flight mass spectrometry from the mean of the most abundant isotopes.

EXAMPLE 27

Solid-Phase Synthesis of Acr$^1$-[Taeg]$_{15}$-NH$_2$ and Shorter Derivatives (a) Stepwise Assembly of Boc-[Taeg]$_{15}$-BHA Resin The synthesis was initiated on 100 mg of preswollen and neutralized BHA resin (determined by the quantitative ninhydrin reaction to contain 0.57 mmol NH$_2$/g) employing single couplings ("Synthetic Protocol 1") using 3.2 equivalents of BocTaeg-OPfp in about 33% DMF/CH$_2$Cl$_2$. The individual coupling reactions were carried out by shaking for at least 12 h in a manually operated 6 ml standard solid-phase reaction vessel and unreacted amino groups were blocked by acetylation at selected stages of the synthesis. The progress of chain elongation was monitored at several stages by the quantitative ninhydrin reaction (see Table I). Portions of protected Boc-[Taeg]$_5$-BHA, Boc-[Taeg]$_{10}$-BHA, and Boc-[Taeg]$_{15}$-BHA resins were taken out after assembling 5, 10, and 15 residues, respectively.

| Synthetic Step | Residue Coupled | Substitution After Deprotection (mmol/g) | | Remaining Free Amino Groups After (μmol/g) | | Estimated Extent of Coupling (%) |
|---|---|---|---|---|---|---|
| | | Measd | Theoretol | Single Coupling | Acetylation | |
| "0" | | 0.57 | | | | |
| 1 | BocTaeg | ND | 0.50 | 1.30 | | <99.7 |
| 2 | BocTaeg | ND | 0.44 | 1.43 | | <99.9 |
| 3 | BocTaeg | 0.29 | 0.39 | 3.33 | | 99.3 |
| 4 | BocTaeg | 0.27 | 0.35 | 13.30 | | 96.3 |
| 5 | BocTaeg | 0.26 | 0.32 | 8.33 | | >99.9 |
| 6 | BocTaeg | ND | 0.30 | 7.78 | | >99.9 |
| 7 | BocaTeg | ND | 0.28 | 13.81 | 7.22 | <97.8 |
| 8 | BocTaeg | ND | 0.26 | 14.00 | | <99.9 |
| 9 | BocTaeg | ND | 0.24 | 30.33 | | 93.2 |
| 10 | BocTaeg | 0.16 | 0.23 | 11.67 | 2.67 | >99.9 |
| 11 | BocTaeg | ND | 0.21 | 4.58 | | >99.9 |
| 12 | BocTaeg | ND | 0.20 | 5.87 | | <99.4 |
| 13 | BocTaeg | ND | 0.19 | 1.67 | | >99.9 |
| 14 | BocTaeg | ND | 0.18 | 14.02 | | <93.1 |
| 15 | BocTaeg | 0.07 | 0.17 | 4.20 | 3.33 | >99.9 |

(b) Synthesis of $Acr^1$-$[Taeg]_{15}$-BHA Resin

Following deprotection of the residual Boc-$[Taeg]_{15}$-BHA resin (estimated dry weight is about 30 mg; ~0.002 mmol growing chains), the H-$[Taeg]_{15}$-BHA resin was reacted with about 50 equivalents (80 mg; 0.11 mmol) of $Acr^1$-OPfp in 1 ml of about 66% $DMF/CH_2Cl_2$ (i.e., a 0.11 M solution of the pentafluorophenylester) in a 3 ml solid-phase reaction vessel. As judged by a qualitative ninhydrin reaction, coupling of the acridine moiety was close to quantitative.

(c) Cleavage, Purification, and Identification of H-$[Taeg]_5$-$NH_2$

A portion of protected Boc-$[Taeg]_5$-BHA resin was treated with 50% trifluoroacetic acid in methylene chloride to remove the N-terminal Boc group (which is a precursor of the potentially harmful tert-butyl cation) prior to the HF cleavage. Following neutralization and washing (performed in a way similar to those of steps 2–4 in "Synthetic Protocol 1"), and drying for 2 h in vacuum, the resulting 67.1 mg (dry weight) of H-$[Taeg]_5$-BHA resin was cleaved with 5 ml of HF:anisole (9:1, v/v) stirring at 0° C. for 60 min. After removal of HF, the residue was stirred with dry diethyl ether (4×15 ml, 15 min each) to remove anisole, filtered under gravity through a fritted glass funnel, and dried. The PNA was then extracted into a 60 ml (4×15 ml, stirring 15 min each) 10% aqueous acetic acid solution. Aliquots of this solution were analyzed by analytical reverse-phase HPLC to establish the purity of the crude PNA. The main peak at 13.0 min accounted for about 93% of the total absorbance. The remaining solution was frozen and lyophilized to afford about 22.9 mg of crude material. Finally, 19.0 mg of the crude product was purified from five batches, each containing 3.8 mg in 1 ml of $H_2O$. The main peak was collected by use of a semi-preparative reverse-phase column. Acetonitrile was removed on a speed vac and the residual solution was frozen (dry ice) and subsequently lyophilized to give 13.1 mg of >99% pure H-$[Taeg]_5$-$NH_2$. The PNA molecule readily dissolved in water and had the correct molecular weight based on mass spectral determination. For $(M+H)^+$ the calculated m/z value was 1349.3 and the measured m/z value was 1347.8.

(d) Cleavage, Purification, and Identification of H-$[Taeg]_{10}$-$NH_2$

A portion of protected Boc-$[Taeg]_{10}$-BHA resin was treated as described in section (c) to yield 11.0 mg of crude material upon HF cleavage of 18.9 mg dry H-$[Taeg]_{10}$-BHA resin. The main peak at 15.5 min accounted for about 53% of the total absorbance. About 1 mg of the crude product was purified repeatedly (for reasons described below) to give approximately 0.1 mg of at least 80% but presumably >99% pure H-$[Taeg]_{10}$-$NH_2$. A rather broad tail eluting after the target peak and accounting for about 20% of the total absorbance could not be removed (only slightly reduced) upon the repeated purification. Judged by the mass spectrum, which only confirms the presence of the correct molecular weight H-$[Taeg]_{10}$-$NH_2$, the tail phenomonen is ascribed to more or less well-defined aggregational/conformational states of the target molecule. Therefore, the crude product is likely to contain more than the above-mentioned 53% of the target molecule. H-$[Taeg]_{10}$-$NH_2$ is readily dissolved in water. For $(M+H)^+$ the calculated m/z value was 2679.6 and the measured m/z value was 2681.5.

(e) Cleavage, Purification, and Identification of H-$[Taeg]_{15}$-$NH_2$.

A portion of protected Boc-$[Taeg]_{15}$-BHA resin was treated as described in section (c) to yield 3.2 mg of crude material upon HF cleavage of 13.9 mg dry H-$[Taeg]_{15}$-BHA resin. The main peak at 22.6 min was located in a broad bulge accounting for about 60% of the total absorbance (FIG. 12a). Again (see the preceding section), this bulge is ascribed to aggregational/conformational states of the target molecule H-$[Taeg]_{15}$-NH2 since mass spectral analysis of the collected "bulge" did not significantly reveal the presence of other molecules. All of the crude product was purified collecting the "bulge" to give approximately 2.8 mg material. For $(M+Na)^+$ the calculated m/z value was 4033.9 and the measured m/z value was 4032.9.

(f) Cleavage, Purification, and Identification of $Acr^1$-$[Taeg]_{15}$-$NH_2$.

A portion of protected $Acr^1$-$[Taeg]_{15}$-BHA resin was treated as described in section (b) to yield 14.3 mg of crude material upon HF cleavage of 29.7 mg dry $Acr^1$-$[Taeg]_{15}$-BHA resin. Taken together, the main peak at 23.7 min and a "dimer" (see below) at 29.2 min accounted for about 40% of the total absorbance (FIG. 12b). The crude product was purified repeatedly to give approximately 1 mg of presumably >99% pure $Acr^1$-$[Taeg]_{15}$-$NH_2$ "contaminated" with self-aggregated molecules eluting at 27.4 min, 29.2 min, and finally as a huge broad bulge eluting with 100% buffer B (FIG. 12c). This interpretation is in agreement with the observation that those peaks grow upon standing (for hours) in aqueous acetic acid solution, and finally precipitate out quantitatively. For (M+H)$^+$ the calculated m/z value was 4593.6 and the measured m/z value was 4588.7.

(g) Synthetic Protocol 1

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin may be taken out and dried thoroughly for a quantitative ninhydrin analysis to determine the substitution; (6) addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h shaking at room temperature; (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a rapid qualitative ninhydrin test and further 2–5 mg is dried thoroughly for a quantitative ninhydrin analysis to determine the extent of coupling (after cycles 7, 10, and 15 unreacted amino groups were blocked by acetylation with N-acetylimidazol in methylene chloride).

EXAMPLE 28

Solid-Phase Synthesis of Acr$^1$-[Taeg]$_{15}$-Lys-NH$_2$ and Shorter Derivatives (a) Stepwise Assembly of Boc-[Taeg]$_{15}$-Lys(ClZ)-BHA Resin The synthesis was initiated by a quantitative loading (standard DCC in situ coupling in neat CH$_2$Cl$_2$) of Boc-Lys (ClZ) onto 100 mg of preswollen and neutralized BHA resin (0.57 mmol NH$_2$/g). Further extension of the protected PNA chain employed single couplings ("Synthetic Protocol 2") for cycles 1 to 5 and cycles 10 to 15 using 3.2 equivalents of BocTaeg-OPfp in about 330 DMF/CH$_2$Cl$_2$. Cycles 5 to 10 employed an extra straight DCC (i.e., in situ) coupling of the free acid BocTaeg-OH in about 33% DMF/CH$_2$Cl$_2$. All coupling reactions were carried out by shaking for at least 12 h in a manually operated 6 ml standard solid-phase reaction vessel. Unreacted amino groups were blocked by acetylation at the same stages of the synthesis, as was done in Example 27. Portions of protected Boc-[Taeg]$_5$-Lys(ClZ)-BHA and Boc-[Taeg]$_{10}$-Lys(ClZ)-BHA resins were taken out after assembling 5 and 10 PNA residues, respectively. As judged by the analytical HPLC chromatogram of the crude cleavage product from the Boc-[Taeg]$_{10}$-Lys(ClZ)-BHA resin (see section (e)), an additional "free acid" coupling of PNA residues 5 to 10 gave no significant improvement of the synthetic yield as compared to the throughout single-coupled residues in Example 27.

(b) Synthesis of Acr$^1$-[Taeg]$_{10}$-Lys(ClZ)-BHA Resin

Following deprotection of a portion of Boc-[Taeg]$_{10}$-Lys (ClZ)-BHA resin (estimated dry weight is about 90 mg; ~0.01 mmol growing chains), the H-[Taeg]$_{15}$-BHA resin was reacted with about 20 equivalents (141 mg; 0.19 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(c) Synthesis of Acr$^1$-[Taeg]$_{15}$-Lys(ClZ)-BHA Resin

Following deprotection of the residual Boc-[Taeg]$_{15}$-Lys (ClZ)-BHA resin (estimated dry weight about 70 mg; ~0.005 mmol growing chains), the H-[Taeg]$_{15}$-Lys(ClZ)-BHA resin was reacted with about 25 equivalents (91 mg; 0.12 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(d) Cleavage, Purification, and Identification of H-[Taeg]$_5$-Lys-NH$_2$

A portion of protected Boc-[Taeg]$_5$-Lys (ClZ)-BHA resin was treated as described in Example 27c to yield 8.9 mg of crude material upon HF cleavage of 19.0 mg dry H-[Taeg]$_5$-Lys(ClZ)-BHA resin. The main peak at 12.2 min (eluted at 14.2 min if injected from an aqueous solution instead of the 10% aqueous acetic acid solution) accounted for about 90% of the total absorbance. About 2.2 mg of the crude product was purified to give approximately 1.5 mg of 99% pure H-[Taeg]$_5$-Lys-NH$_2$.

(e) Cleavage, Purification, and Identification of H-[Taeg]$_{10}$-Lys-NH$_2$

A portion of protected Boc-[Taeg]$_{10}$-Lys (ClZ)-BHA resin was treated as described in Example 27c to yield 1.7 mg of crude material upon HF cleavage of 7.0 mg dry H-[Taeg]$_{10}$-Lys(ClZ)-BHA resin. The main peak at 15.1 min (eluted at 17.0 min if injected from an aqueous solution instead of the 10% aqueous acetic acid solution) accounted for about 50% of the total absorbance. About 1.2 mg of the crude product was purified to give approximately 0.2 mg of >95% pure H-[Taeg]$_{10}$-Lys-NH$_2$. FIG. 10a. For (M+H)$^+$ the calculated m/z value was 2807.8 and the measured m/z value was 2808.2.

(f) Cleavage, Purification, and Identification of Acr$^1$-[Taeg]$_{10}$-Lys-NH$_2$ 99.1 mg protected Acr$^1$-[Taeg]$_{10}$-Lys(ClZ)-BHA resin (dry weight) was cleaved as described in Example 27c to yield 42.2 mg of crude material. The main peak at 25.3 min (eluted at 23.5 min if injected from an aqueous solution instead of the 10% aqueous acetic acid solution) accounted for about 45% of the total absorbance. An 8.87 mg portion of the crude product was purified to give approximately 5.3 mg of >97% pure H-[Taeg]$_{10}$-Lys-NH$_2$. For (M+H)$^+$ the calculated m/z value was 2850.8 and the measured m/z value was 2849.8.

(g) Cleavage and Purification of Acr$^1$-[Taeg]$_{15}$-Lys-NH$_2$

A 78.7 mg portion of protected Acr$^1$-[Taeg]$_{15}$-Lys(ClZ)-BHA resin (dry weight) was cleaved as described in Example 27(c) to yield 34.8 mg of crude material. The main peak at 23.5 min (about the same elution time if injected from an aqueous solution instead of the 10% aqueous acetic acid solution) and a "dimer" at 28.2 min accounted for about 35% of the total absorbance. About 4.5 mg of the crude product was purified to give approximately 1.6 mg of presumably >95% pure H-[Taeg]$_{10}$-Lys-NH$_2$. This compound could not be free of the "dimer" peak, which grew upon standing in aqueous acetic acid solution.

(h) Synthetic Protocol 2

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin can be taken out and dried thoroughly for a qualitative ninhydrin analysis; (6) for cycles 1 to 5 and cycles 10 to 15 the coupling reaction was carried out by addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h with shaking; cycles 5 to 10 employed an additional 0.12 M DCC coupling of 0.12 M BocTaeg-OH in 1.5 ml DMF/CH$_2$Cl$_2$ (1:2, v/v); (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a qualitative ninhydrin test (after cycles 7, 10, and 15 unreacted amino groups were blocked by acetylation with N-acetylimidazol in methylene chloride).

EXAMPLE 29

Improved Solid-Phase Synthesis of H-[Taeg]$_{10}$-Lys-NH$_2$

The protected PNA was assembled onto an MBHA resin, using approximately half the loading of the BHA resin used in the previous examples. Furthermore, all cycles except one was followed by acetylation of uncoupled amino groups. The following describes the synthesis in full detail:

(a) Preparation of Boc-Lys(ClZ)-NH-CH(p-CH$_3$-C$_6$H$_4$)-C$_6$H$_4$ Resin (MBHA Resin) with an Initial Substitution of 0.3 mmol/g The desired substitution of Boc-Lys(ClZ)-MBHA resin was 0.25–0.30 mmol/g. In order to get this value, 1.5 mmol of Boc-Lys(ClZ) was coupled to 5.0 g of neutralized and preswollen MBHA resin (determined by the quantitative ninhydrin reaction to contain 0.64 mmol NH$_2$/g) using a single "in situ" coupling (1.5 mmol of DCC) in 60 ml of CH$_2$Cl$_2$. The reaction was carried out by shaking for 3 h in a manually operated, 225 ml, standard, solid-phase reaction vessel. Unreacted amino groups were then blocked by acetylation with a mixture of acetic anhydride/pyridine/CH$_2$Cl$_2$ (1:1:2, v/v/v) for 18 h. A quantitative ninhydrin reaction on the neutralized resin showed that only 0.00093 mmol/g free amine remained (see Table I), i.e. 0.15% of the original amino groups. The degree of substitution was estimated by deprotection and ninhydrin analysis, and was found to be 0.32 mmol/g for the neutralized H-Lys (ClZ)-MBHA resin. This compares well with the maximum value of 0.28 mmol/g for a quantitative coupling of 0.30 mmol Boc-Lys(ClZ)/g resin (see Table II).

(b) Stepwise Assembly of Boc-[Taeg]$_3$-Lys(ClZ)-MBHA Resin

The entire batch of H-Lys(ClZ)-MBHA resin prepared in section (a) was used directly (in the same reaction vessel) to assemble Boc-[Taeg]$_3$-Lys(ClZ)-MBHA resin by single couplings ("Synthetic Protocol 3") utilizing 2.5 equivalents of BocTaeg-OPfp in neat CH$_2$Cl$_2$. The quantitative ninhydrin reaction was apppplied throughout the synthesis (see Table II).

(c) Stepwise Assembly of Boc-[Taeg]$_8$-Lys(ClZ)-MBHA Resin

About 4.5 g of wet Boc-[Taeg]$_3$-Lys(ClZ)-MBHA resin (~0.36 mmol growing chains; taken out of totally ~19 g wet resin prepared in section (b)) was placed in a 55 ml SPPS reaction vessel. Boc-[Taeg]$_8$-Lys(ClZ)-MBHA resin was assembled by single couplings ("Synthetic Protocol 4") utilizing 2.5 equivalents of BocTaeg-OPfp in about 30% DMF/CH$_2$Cl$_2$. The progress of the synthesis was monitored at all stages by the quantitative ninhydrin reaction (see Table II).

(d) Stepwise Assembly of Boc-[Taeg]$_{10}$-Lys(ClZ)-MBHA Resin

About 1 g of wet Boc-[Taeg]$_8$-Lys(ClZ)-MBHA resin (~0.09 mmol growing chains; taken out of totally ~4 g wet resin prepared in section (c)) was placed in a 20 ml SPPS reaction vessel. Boc-[Taeg]$_{10}$-Lys(ClZ)-MBHA resin was assembled by the single-coupling protocol employed in the preceding section utilizing 2.5 equivalents of BocTaeg-OPfp in about 30% DMF/CH$_2$Cl$_2$. The reaction volume was 3 ml (vigorous shaking). The synthesis was monitored by the quantitative ninhydrin reaction (see Table II).

| Synthetic Step | Residue Coupled | Substitution After Deprotection (mmol/g) | | Remaining Free Amino Groups After ($\mu$mol/g) | | Estimated Extent of Coupling (%) |
| --- | --- | --- | --- | --- | --- | --- |
| | | Measd | Theoret | Single Coupling | Acetylation | |
| "0" | BocLys(ClZ) | 0.32 | 0.28 | | 0.93 | |
| 1 | BocTaeg | 0.23 | 0.26 | 0.97 | 0.54 | >99.9 |
| 2 | BocTaeg | 0.21 | 0.24 | 0.92 | 0.46 | 99.8 |
| 3 | BocTaeg | 0.19 | 0.23 | 1.00 | 0.57 | 99.7 |
| 4 | BocTaeg | 0.18 | 0.21 | 1.85 | | 99.3 |
| 5 | BocTaeg | 0.17 | 0.20 | 2.01 | 0.19 | 99.9 |
| 6 | BocTaeg | 0.15 | 0.19 | 1.69 | 0.10 | 99.0 |
| 7 | BocaTeg | 0.11 | 0.18 | 1.11 | 0.66 | 99.1 |
| 8 | BocTaeg | 0.12 | 0.17 | 1.82 | 0.44 | 99.0 |
| 9 | BocTaeg | 0.10 | 0.17 | 5.63 | 0.56 | 94.8 |
| 10 | BocTaeg | 0.11 | 0.16 | 1.54 | 0.67 | 99.1 |

(e) Synthesis of Ac-[Taeg]$_{10}$-Lys(ClZ)-MBHA Resin

Following deprotection of a portion of Boc-[Taeg]$_{10}$-Lys (ClZ)-MBHA resin (estimated dry weight is about 45 mg), the resin was next acetylated quantitatively with a 2 ml mixture of acetic anhydride/pyridine/CH$_2$Cl$_2$ (1:1:2, v/v/v) for 2 h in a 3 ml solid-phase reaction vessel.

(f) Cleavage, Purification, and Identification of H-[Taeg]$_{10}$-Lys-NH$_2$

A portion of protected Boc-[Taeg]$_{10}$-Lys(ClZ)-BHA resin was treated as described in Example 27c to yield about 24 mg of crude material upon HF cleavage of 76 mg dry H-[Taeg]$_5$-Lys(ClZ)-BHA resin. The main peak at 15.2 min (which includes impurities such as deletion peptides and various byproducts) accounted for about 78% of the total absorbance. The main peak also accounted for about 88% of the "main peak plus deletion peaks" absorbance, which is in good agreement with the overall estimated coupling yield of 90.1% obtained by summarizing the individual coupling yields in Table II. A 7.2 mg portion of the crude product was purified from two batches by use of a semi-preparative reserse-phase column, (collecting the main peak in a beaker cooled with dry ice/2-propanol). Each contained 3.6 mg in 1 ml of H$_2$O. The frozen solution was lyophilized directly (without prior removal of acetonitrile on a speed vac) to give 4.2 mg of 82% pure H-[Taeg]$_{10}$-Lys-NH$_2$.

(g) Cleavage, Purification, and Identification of Ac-[Taeg]$_{10}$-Lys-NH$_2$

A 400.0 mg portion of protected Ac-[Taeg]$_{10}$-Lys(ClZ)-BHA resin (dry weight) was cleaved as described in Example 27c, except for the TFA treatment to yield 11.9 mg of crude material. The main peak at 15.8 min accounted for about 75% of the total absorbance. A 4.8 mg portion of the crude product was purified to give approximately 3.5 mg of >95% pure Ac-[Taeg]$_{10}$-Lys-NH$_2$. For (M+H)$^+$ the calculated m/z value=2849.8 and the measured m/z value=2848.8.

(h) Synthetic Protocol 3.

(1) Boc-deprotection with TFA/CH$_2$Cl$_2$ (1:1, v/v), 100 ml, 3×1 min and 1×30 min; (2) washing with CH$_2$Cl$_2$, 100 ml, 6×1 min; (3) neutralization with DIEA/CH$_2$Cl$_2$(1:19, v/v), 100 ml, 3×2 min; (4) washing with CH$_2$Cl$_2$, 100 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (3.75 mmol; 2.064 g) BocTaeg-OPfp dissolved in 35 ml CH$_2$Cl$_2$ (final concentration of pentafluorophenylester ~0.1 M); the coupling reaction was allowed to proceed for a total of 20–24 h with shaking; (7) washing with DMF, 100 ml, 1×2 min (to remove precipitate of BocTaeg-OH); (8) washing with CH$_2$Cl$_2$, 100 ml, 4×1 min; (9) neutralization with DIEA/CH$_2$Cl$_2$ (1:19, v/v), 100 ml, 2×2 min; (10) washing with CH$_2$Cl$_2$, 100 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 100 ml mixture of acetic anhydride/pyridine/CH$_2$Cl$_2$ (1:1:2, v/v/v) for 2 h; (13) washing with CH$_2$Cl$_2$, 100 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

(i) Synthetic Protocol 4.

(1) Boc-deprotection with TFA/CH$_2$Cl$_2$ (1:1, v/v), 25 ml, 3×1 min and 1×30 min; (2) washing with CH$_2$Cl$_2$, 25 ml, 6×1 min; (3) neutralization with DIEA/CH$_2$Cl$_2$ (1:19, v/v), 25 ml, 3×2 min; (4) washing with CH$_2$Cl$_2$, 25 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (0.92 mmol; 0.506 g) BocTaeg-OPfp dissolved in 6 ml CH$_2$Cl$_2$ followed by addition of 3 ml DMF (final concentration of pentafluorophenylester ~0.1 M); the coupling reaction was allowed to proceed for a total of 20–24 hrs with shaking; (7) washing with DMF, 25 ml, 1×2 min; (8) washing with CH$_2$Cl$_2$, 25 ml, 4×1 min; (9) neutralization with DIEA/CH$_2$Cl$_2$ (1:19, v/v), 25 ml, 2×2 min; (10) washing with CH$_2$Cl$_2$, 25 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the first cycle); (13) washing with CH$_2$Cl$_2$, 25 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

EXAMPLE 30

Solid-Phase Synthesis of H-[Taeg]$_5$-Caeg-[Taeg]$_4$-Lys-NH$_2$ (a) Stepwise Assembly of Boc-[Taeg]$_5$-C(z) aeg-[Taeg]$_4$-Lys(ClZ)-MBHA Resin About 2.5 g of wet Boc-[Taeg]$_5$-Lys(ClZ)-MBHA resin (~⅙ of the total remaining about 16 g wet resin; ~0.75 g dry resin ~0.15 mmol growing chains) was placed in a 6 ml SPPS reaction vessel. Boc-[Taeg]$_5$-Caeg-[Taeg]$_4$-Lys(ClZ)-MBHA resin was assembled by double coupling of all Taeg-residues utilizing the usual 2.5 equivalents of BocTaeg-OPfp in 2.5 ml about 30% DMF/CH$_2$Cl$_2$, except that the first residue was single-coupled. Incorporation of the C(Z)aeg-residue was accomplished by coupling with 2.0 equivalents of BocC(Z)aeg-OPfp in TFE/CH$_2$Cl$_2$ (1:2, v/v). The progress of the synthesis was monitored at all stages by the quantitative ninhydrin reaction (see Table III).

| Synthetic Step | Residue Coupled | Substitution After Deprotection (mmol/g) | | Remaining Free Amino Groups After ($\mu$mol/g) | | Acetyl-ation | Estimated Extent of Coupling |
|---|---|---|---|---|---|---|---|
| | | Measd. | Theoret. | 1st Coupl | 2nd Coupl | | |
| 3 | | 0.19 | 0.23 | 1.00 | | 0.57 | |
| 4 | BocTaeg | 0.17 | 0.21 | 4.88 | | 97.3 | 97.3 |
| 5 | BocC(Z)aeg | 0.11 | 0.20 | 70.20 | 27.98 | 1.33 | 78.4 (46) |
| 6 | BocTaeg | 0.10 | 0.19 | 24.79 | 4.58 | 2.40 | 95.4 (75) |
| 7 | BocTaeg | 0.09 | 0.18 | 8.55 | 1.61 | 0.20 | >99.9 (93) |
| 8 | BocTaeg | 0.08 | 0.17 | 6.53 | 0.80 | 0.45 | 99.0 (91) |
| 9 | BocTaeg | 0.07 | 0.16 | 9.26 | 3.66 | 0.61 | 94.8 (86) |
| 10 | BocTaeg | 0.07 | 0.15 | 5.32 | 1.48 | 0.60 | 98.8 (93) |

(b) Cleavage, Purification, and Identification of H-[Taeg]$_5$-Caeg-[Taeg]$_4$-Lys -NH$_2$ A portion of protected Boc-[Taeg]$_5$-Caeg-[Taeg]$_4$-Lys (ClZ)-BHA resin was treated as described in Example 27(c) to yield about 14.4 mg of crude material upon HF cleavage of 66.9 mg dry H-[Taeg]$_5$-Caeg-[Taeg]$_4$-Lys(ClZ)-BHA resin. The main peak at 14.5 min accounted for >50% of the total absorbance. A 100.0 mg portion of the crude product was purified (8 batches; each dissolved in 1 ml H$_2$O) to give approximately 9.1 mg of 96% pure H-[Taeg]$_5$-Caeg-[Taeg]$_4$-Lys-NH$_2$ (FIG. 10b). For (M+H)$^+$ the calculated m/z value=2793,8 and the measured m/z value=2790,6.

EXAMPLE 31

Binding of Acr$^1$-(Taeg)$_{10}$-Lys-NH$_2$ to dA$_{10}$ (FIG. 11)

Acr$^1$-(Taeg)$_{10}$-Lys (100 ng) was incubated for 15 min at room temperature with 50 cps 5'-[$^{32}$P]-end-labelled oligonucleotide [d(GATCCA$_{10}$G)] in 20 µl TE buffer (10 mM Tris-HCl, 1 mM EDTA, pH 7.4). The sample was cooled in ice (15 min) and analyzed by gel electrophoresis in polyacrylamide (PAGE). To 10 µl of the sample was added 2 µl 50% glycerol, 5 TBE (TBE=90 mM Tris-borate, 1 mM EDTA, pH 8.3), and the sample was analysed by PAGE (15% acrylamide, 0.5% bisacrylamide) in TBE buffer at 4° C. A 10 µl portion of the sample was lyophilized and redissolved in 10 µl 80% formamide, 1 TBE, heated to 90° C. (5 min), and analyzed by urea/PAGE (15% acrylamide, 0.5% bisacrylamide, 7 M urea) in TBE. [$^{32}$P]-containing DNA bands were visualized by autoradiography using intensifying screens and Agfa Curix RPI X-ray films exposed at −80° C. for 2 h.

Oligonucleotides were synthesized on a Biosearch 7500 DNA synthesizer, labelled with γ[$^{32}$P]-ATP (Amersham, 5000 Ci/mmol) and polynucleotide kinase, and purified by PAGE using standard techniques (Maniatis et al. (1986): A laboratory manual, Cold Spring Harbor Laboratories).

EXAMPLE 32

Formation of Strand Displacement Complex

A dA$_{10}$–dT$_{10}$ target sequence contained within a plasmid DNA sequence was constructed by cloning of two oligonucleotides (d(GATCCA$_{10}$G) (SEQ ID NO: 9)+d (GATCCT$_{10}$G)) (SEQ ID NO: 10)) into the BamHI restriction enzyme site of pUC19 using the *Eschericia coli* JM101 strain by standard techniques (Maniatis et al., 1986). The desired plasmid (designated pT10) was isolated from one of the resulting clones and purified by the alkaline extraction procedure and CsCl centrifugation (Maniatis et al., 1986). A 3'-[$^{32}$P]-end-labelled DNA fragment of 248 bp containing the dA$_{10}$/dT$_{10}$ target sequence was obtained by cleaving the pT10 DNA with restriction enzymes EcoRI and PvuII, labelling of the cleaved DNA with α[$^{32}$P]-dATP (4000 Ci/mmol, Amersham) using the Klenow fragment of *E. coli* DNA polymerase (Boehringer Mannheim), and purifying the 248 bp DNA fragment by PAGE (5% acrylamide, 0.06% bisacrylamide, TBE buffer). This DNA fragment was obtained with [32P]-end-labelling at the 5'-end by treating the EcoRI-cleaved pT10 plasmid with bacterial alkaline phosphatase (Boehringer Mannheim), purifying the plasmid DNA by gel electrophoresis in low melting agarose, and labelling with γ[32P] ATP and polynucleotide kinase. Following treatment with PvuII, the 248 bp DNA fragment was purified as above.

The complex between Acr$^1$-(Taeg)$_{10}$-Lys-NH$_2$ and the 248 bp DNA fragment was formed by incubating 50 ng of Acr$^1$-(Taeg)$_{10}$-Lys-NH$_2$ with 500 cps $^{32}$P-labelled 248 bp fragment and 0.5 µg calf thymus DNA in 100 µl buffer for 60 min at 37° C.

EXAMPLE 33

Probing of Strand Displacement Complex with:

(a) Staphylococcus Nuclease (FIG. 12*b*)

The strand displacement complex was formed in 25 mM Tris-HCl, 1 mM MgCl$_2$, 0.1 mM CaCl$_2$, pH 7.4 as described above. The complex was treated with Staphylococcus nuclease (Boehringer Mannheim) at 750 U/ml for 5 min at 20° C. and the reaction was stopped by addition of EDTA to 25 mM. The DNA was precipitated with 2 vols. of ethanol, 2% potassium acetate redissolved in 80% formamide, TBE, heated to 90° C. (5 min), and analyzed by high resolution PAGE (10% acrylamide, 0.3% bisacrylamide, 7 M urea) and autoradiography.

(b) Affinity Photocleavage (FIG. 12*a*+12*b*)

The complex was formed in TE buffer. A sample contained in an Eppendorf tube was irradiated from above at 300 nm (Philips TL 20 W/12 fluorescent light tube, 24 Jm$^{-2}$s$^{-1}$) for 30 min. The DNA was precipitated as above, taken up in 1 M piperidine, and heated to 90° C. for 20 min. Following lyophilization, the DNA was analysed by PAGE as above.

(c) Potassium Permanganate (FIG. 12*b*)

The complex was formed in 100 µl TE and 5 µl 20 mM KMnO$_4$ was added. After 15 s at 20° C., the reaction was stopped by addition of 50 µl 1.5 M sodium acetate, pH 7.0, 1 M 2-mercaptoethanol. The DNA was precipitated, treated with piperidine and analyzed, as above.

(d) Photofootprinting (FIG. 12*b*)

The complex was formed in 100 µl TE and diazo-linked acridine (0.1 µg/µl) (DHA, Nielsen et al. (1988) Nucl. Acids Res. 16, 3877–88) was added. The sample was irradiated at 365 nm (Philips TL 20 W/09N, 22 Jm$^{-2}$s$^{-1}$) for 30 min and treated as described for "affinity photocleavage".

(e) S$_1$-nuclease (FIG. 12*c*)

The complex was formed in 50 mM sodium acetate, 200 mM NaCl, 0.5% glycerol, 1 mM ZnCl$_2$, pH 4.5 and treated with nuclease S$_1$ (Boehringer Mannheim) at 0.5 U/ml for 5 min at 20° C. The reaction was stopped and treated further as described under "Staphylococcus nuclease".

EXAMPLE 34

N-Benzyloxycarbonyl-N-'(bocaminoethyl)glycine.

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2 N NaOH at 0° C. Benzyloxycarbonyl chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml). Yield 124.7 g (79%). M.p. 64.5–85° C. Anal. for C$_{17}$H$_{24}$N$_2$O$_6$ found(calc.) C: 58.40(57.94); H: 7.02(6.86); N: 7.94(7.95). $^1$H-NMR (250 MHz, CDCl$_3$) 7.33 & 7.32 (5H, Ph); 5.15 & 5.12 (2H, PhC$\underline{H}_2$); 4.03 & 4.01 (2H, NC$\underline{H}_2$CO$_2$H); 3.46 (b, 2H, BocNHCH$_2$C$\underline{H}_2$); 3.28 (b, 2H, BocNHC$\underline{H}_2$CH$_2$); 1.43 & 1.40 (9H, $^t$Bu). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 35

N'-Boc-aminoethyl glycine ethyl ester

N-Benzyloxycarbonyl-N'-(bocaminoethyl)glycine (60.0 g; 0.170 mol) and N,N-dimethyl-4-aminopyridine (6.00 g)

were dissolved in absolute ethanol (500 ml), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g $SiO_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, $CD_3OD$); 4.77 (b. s, NH); 4.18 (q, 2H, $MeCH_2$—); 3.38 (s, 2H, NC $H_2CO_2Et$); 3.16 (t, 2H, $BocNHCH_2CH_2$); 2.68 (t, 2H, $BocNHCH_2CH_2$); 1.43 (s, 9H, $^tBu$) and 1.26 (t, 3H, $CH_3$) $^{13}$C-NMR 171.4 ($\underline{C}OEt$); 156.6 (CO); 78.3 (($CH_3$)$_3\underline{C}$); 59.9 ($CH_2$); 49.0 ($CH_2$); 48.1 ($CH_2$); 39.0 ($CH_2$); 26.9 ($CH_2$) and 12.6 ($CH_3$).

EXAMPLE 36

N'-Boc-aminoethyl glycine methyl ester

The above procedure was used, with methanol being substituted for ethanol. The final product was purified by column purification.

EXAMPLE 37

1-(Boc-aeg)thymine ethyl ester

N'-Boc-aminoethyl glycine ethyl ester (13.5 g; 54.8 mmol), DhbtOH (9.84 g; 60.3 mmol) and 1-carboxymethyl thymine (11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration. The organic phase was dried over magnesium sulfate and evaporated to dryness, in vacuo. The oily residue was dissolved in methylene chloride (150 ml), filtered, and the title compound was precipitated by the addition of petroleum ether (350 ml) at 0° C. The methylene chloride/petroleum ether procedure was repeated once. This afforded 16.0 g (71) of a material which was more than 99% pure by HPLC.

EXAMPLE 38

1-(Boc-aeg)thymine

The material from above was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to the solution which was then washed with methylene chloride (300 ml). Additional water (30 ml) was added, and the alkaline solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts were dried over magnesium sulfate and were evaporated to dryness, in vacuo. The residue was evaporated once from methanol, which after drying overnight afforded a colorless glassy solid. Yield 9.57 g (64%). HPLC >98% $R_T$=14.8 min . Anal. for $C_{16}H_{24}N_4O_7$°0.25 $H_2O$ Found (calc.) C: 49.29(49.42); H: 6.52(6.35); N: 14.11(14.41). Due to the limited rotation around the secondary amide, several of the signals were doubled in the ratio 2:1 (indicated in the list by mj. for major and mi. for minor). $^1$H-NMR (250 MHz, DMSO-$d_6$): 12.75 (b.s., 1H, $CO_2H$); 11.28 (s, "1H", mj., imide NH); 11.26 (s, "1H", mi., imide NH); 7.30 (s, "1H", mj., T H-6); 7.26 (s, "1H", mi., T H-6); 6.92 (b.t., "1H", mj., BOcNH); 6.73 (b.t., "1H", mi., BOcNH); 4.64 (s, "2H", mj., $CH_2CON$); 4.46 (s, "2H", mj., $CH_2CON$); 4.19 (s, "2H", mi., $CH_2CO_2H$); 3.97 (s, "2H", mj., $CH_2CO_2H$); 3.63–3.01 (unresolved m, includes water, $CH_2CH_2$); 1.75 (s, 3H, $CH_3$) and 1.38 (s, 9H, $^tBu$).

EXAMPLE 39

$N^4$-Benzyloxycarbonyl-1-(Boc-aeg)cytosine

N'-Boc-aminoethyl glycine ethyl ester (5.00 g; 20.3 mmol), DhbtOH (3.64 g; 22.3 mmol) and $N^4$-benzyloxycarbonyl-1-carboxymethyl cytosine (6.77 g; 22.3 mmol) were suspended in DMF (100 ml). Methylene chloride (100 ml) then was added. The solution was cooled to 0° C. and DCC (5.03 g; 24.4 mmol) was added. The ice bath was removed after 2 h and stirring was continued for another hour at ambient temperature. The reaction mixture then was evaporated to dryness, in vacuo. The residue was suspended in ether (100 ml) and stirred vigorously for 30 min. The solid material was isolated by filtration and the ether wash procedure was repeated twice. The material was then stirred vigorously for 15 min with dilute sodium hydrogencarbonate (aprox. 4% solution, 100 ml), filtered and washed with water. This procedure was then repeated once, which after drying left 17.0 g of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for 15 minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% $R_T$=19.5 min, and a minor impurity at 12.6 min (approx. 1%) most likely the Z-de protected monomer. Anal. for $C_{23}H_{29}N_5O_8$ found(calc.) C: 54.16(54.87); H: 5.76(5.81) and N: 13.65(13.91). $^1$H-NMR (250 MHz, DMSO-$d_6$). 10.78 (b.s, 1H, CO$_2$H); 7.88 (2 overlapping dublets, 1H, Cyt H-5); 7.41–7.32 (m, 5H, Ph); 7.01 (2 overlapping doublets, 1H, Cyt H-6); 6.94 & 6.78 (unres. triplets, 1H, BocNH); 5.19 (s, 2H, PhCH$_2$); 4.81 & 4.62 (s, 2H, CH$_2$CON); 4.17 & 3.98 (s, 2H, CH$_2$CO$_2$H); 3.42–3.03 (m, includes water, CH$_2$CH$_2$) and 1.38 & 1.37 (s, 9H, $^t$Bu). $^{13}$C-NMR. 150.88; 128.52; 128.18; 127.96; 93.90; 66.53; 49.58 and 28.22. IR: Frequency in cm$^{-1}$ (intensity). 3423 (26.4), 3035 (53.2), 2978(41.4), 1736(17.3), 1658(3.8), 1563(23.0), 1501(6.8) and 1456 (26.4).

EXAMPLE 40

9-Carboxymethyl adenine ethyl ester

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5–220° C. Anal. for $C_9H_{11}N_5O_2$ found(calc.): C: 48.86 (48.65); H: 5.01(4.91); N: 31.66(31.42). $^1$H-NMR (250 MHz; DMSO-$d_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0), 1671(1.8), 1644(10.9), 1606(0.6), 1582(7.1), 1522(43.8), 1477(7.2), 1445(35.8) and 1422(8.6). The position of alkylation was verified by X-ray crystallography on crystals, which were obtained by recrystallization from 96% ethanol.

Alternatively, 9-carboxymethyl adenine ethyl ester can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) haxane washed sodium hydride-mineral oil dispersion. The mixture was stirred vigorously for 2 hours, whereafter ethy bromacetate 75 ml, 0.67 mol) was added dropwise over the course of 3 hours. The mixture was stirred for one additional hour, whereafter tlc indicated complete conversion of adenine. The mixture was evaporated to dryness at 1 mmHg and water (500 ml) was added to the oily residue which caused crystallisation of the title compound. The solid was recrystallised from 06% ethanol (600 ml). Yield after drying 53.7 (65.6%). HPLC (215 nm) purity >99.5%.

EXAMPLE 41

N$^6$-Benzyloxycarbonyl-9-carboxymethyl adenine ethyl ester

9-Carboxymethyladenine ethyl ester (3.40 g, 15.4 mmol) was dissolved in dry DMF (50 ml) by gentle heating, cooled to 20° C., and added to a solution of N-ethyl-benzyloxycarbonylimidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleumeum ether (50 ml). This procedure was repeated once to give 3.45 g (63%) of the title compound. M.p. 132–350° C. Analysis for $C_{17}H_{17}N_5O_4$ found (calc.): C: 56.95(57.46); H: 4.71(4.82); N: 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N-CH$_2$); 4.96 (s, 2H, Ph-CH$_2$); 4.27 (q, 2H, J=7.15 Hz, CH$_2$CH$_3$) and 1.30 (t, 3H, J=7.15 Hz, CH$_2$CH$_3$). $^{13}$C-NMR: 153.09; 143.11; 128.66; 67.84; 62.51; 44.24 and 14.09. FAB-MS: 356 (MH+) and 312 (MH+—CO$_2$). IR: frequency in cm$^{-1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 1492(37.9); 1465(14.0) and 1413(37.3).

EXAMPLE 42

N$^6$-Benzyloxycarbonyl-9-carboxymethyl adenine

N$^6$-Benzyloxycarbonyl-9-carboxymethyladenine ethyl ester (3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C: 46.32(55.05); H: 4.24(4.00); N: 18.10 (21.40) and C/N: 2.57(2.56). $^1$H-NMR(250 MHz; DMSO-$d_6$): 8.70 (s, 2H, H-2 and H-8); 7.50–7.35 (m, 5H, Ph); 5.27 (s, 2H, N-CH$_2$); and 5.15 (s, 2H, Ph-CH$_2$). $^{13}$C-NMR. 168.77, 152.54, 151.36, 148.75, 145.13, 128.51, 128.17, 127.98, 66.76 and 44.67.IR (KBr) 3484(18.3); 3109(15.9); 3087(15.0); 2966(17.1); 2927(19.9); 2383(53.8); 1960 (62.7); 1739(2.5); 1688(5.2); 1655(0.9); 1594(11.7); 1560 (12.3); 1530(26.3); 1499(30.5); 1475(10.4); 1455(14.0); 1429(24.5) and 1411(23.6). FAB-MS: 328 (MH+) and 284 (MH+—CO$_2$). HPLC (215 nm, 260 nm) in system 1:15.18 min, minor impurities all less than 2%.

EXAMPLE 43

N$^6$-Benzyloxycarbonyl-1-(Boc-aeg)adenine ethyl ester

N'-Boc-aminoethyl glycine ethyl ester (2.00 g; 8.12 mmol), DhbtOH (1.46 g; 8.93 mmol) and N$^6$-benzyloxycarbonyl-9-carboxymethyl adenine (2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95%. Anal. for $C_{26}H_{33}N_7O_7 \cdot H_2O$ found(calc.) C: 55.01(54.44; H: 6.85 (6.15) and N: 16.47(17.09). $^1$H-NMR (250 MHz, $CDCl_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BocNH); 5.30 (s, 2H, $PhCH_2$); 5.16 & 5.00 (s, 2H, C$\underline{H}_2$CON); 4.29 & 4.06 (s, 2H, C$\underline{H}CO_2$H); 4.20 (q, 2H, OC$\underline{H}_2CH_3$); 3.67–3.29 (m, 4H, $C\underline{H}_2C\underline{H}_2$); 1.42 (s, 9H, $^tBu$) and 1.27 (t, 3H, $OCH_2C\underline{H}_3$). The spectrum shows traces of ethanol and DCU.

EXAMPLE 44

$N^6$-Benzyloxycarbonyl-1-(Boc-aeg)adenine $N^6$-Benzyloxycarbonyl-1-(Boc-aeg)adenine ethyl ester (1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, and drief affording 0.82 g (58%). The product reprecipitated twice with methylene chloride/petroleum ether, 0.77 g (55%) after drying. M.p. 119° C. (decomp.) Anal. for $C_{24}H_{29}N_7O_7 \cdot H_2O$ found(calc.) C: 53.32(52.84); H: 5.71 (5.73); N: 17.68(17.97). FAB-MS. 528.5 (MH+). $^1$H-NMR (250 MHz, DMSO-$d_6$). 12.75 (very b, 1H, $CO_2H$); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BocNH); 5.33 & 5.16 (s, 2H, $CH_2CON$); 5.22 (s, 2H, $PhC\underline{H}_2$); 4.34–3.99 (s, 2H, $CH_2CO_2H$); 3.54–3.03 (m's, includes water, $C\underline{H}_2C\underline{H}_2$) and 1.39 & 1.37 (s, 9H, $^tBu$). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 45

2-Amino-6-chloro-9-carboxymethylpurine

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over sicapent. Yield (3.02 g; 44.8%). $^1$H-NMR(DMSO-d6): d=4.88 ppm (s,2H); 6.95 (s,2H); 8.10 (s,1H).

EXAMPLE 46

2-Amino-6-benzyloxy-9-carboxymethylpurine

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacou, over sicapent: 2.76 g (52%). M.p. 159–65° C. Anal. (calc., found) C(56.18; 55.97), H(4.38; 4.32), N(23.4; 23.10). $^1$H-NMR (DMSO-$d_6$): 4.82 ppm.(s,2H); 5.51 (s,2H); 6.45 (s,2H); 7.45 (m,5H); 7.82 (s,1H).

EXAMPLE 47

N-([2-Amino-6-benzyloxy-purine-9-yl]-acetyl)-N-(2-Boc-aminoethyl)-glycine [BocGaeg-OH monomer].

2-Amino-6-benzyloxy-9-carboxymethyl-purine (0.50 g; 1.67 mmol), methyl-N(2-[tert-butoxycarbonylamino]ethyl) glycinate (0.65 g; 2.80 mmol), diisopropylethyl amine (0.54 g; 4.19 mmol), and bromo-tris-pyrrolidino-phosphonium-hexafluoro-phosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3×40 ml). The organic layer was washed with potassium hydrogen sulfate solution (1 N; 2×40 ml), sodium hydrogen carbonate (1 N; 1×40 ml) and saturated sodium chloride solution (60 ml). After drying with anhydrous sodium sulfate and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^1$H-NMR(250, MHz, DMSO-$d_6$): d=1.4 ppm. (s,9H); 3.2 (m,2H); 3.6 (m,2H); 4.1 (s, mj., $CONRC\underline{H}_2COOH$); 4.4 (s, mi., CONRC$\underline{H}_2$COOH); 5.0 (s, mi., Gua-C$\underline{H}_2$CO—); 5.2 (s, mj., Gua-C$\underline{H}_2$CO); 5.6 (s,2H); 6.5 (s,2H); 6.9 (m, mi., BOcNH); 7.1 (m, mj., BOcNH); 7.5 (m.,3H); 7.8 (s,1H); 12,8 (s; 1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 48

3-Boc-amino-1,2-propanediol

3-Amino-1,2-propanediol (40.00 g, 0.440 mol, 1.0 eq.) was dissolved in water (1000 ml) and cooled to 0° C. Di-tert-butyl dicarbonate (115.0 g, 0.526 mol, 1.2 eq.) was added in one portion. The reaction mixture was heated to room temperature on a water bath during stirring. The pH was maintained at 10.5 with a solution of sodium hydroxide (17.56 g, 0.440 mol, 1.0 eq.) in water (120 ml). When the addition of aqueous sodium hydroxide was completed, the reaction mixture was stirred overnight at room temperature. Subsequently, ethyl acetate (750 ml) was added to the reaction mixture, followed by cooling to 0° C. The pH was adjusted to 2.5 with 4 N sulphuric acid with vigorous stirring. The phases were separated and the water phase was washed with additional ethyl acetate (6×350 ml). The volume of the organic phase was reduced to 900 ml by evaporation under reduced pressure. The organic phase then was washed with a saturated aqueous solution of potassium hydrogen sulfate diluted to twice its volume (1×1000 ml) and with saturated aqueous sodium chloride (1×500 ml). The organic phase was dried ($MgSO_4$) and evaporated under reduced pressure to yield 50.12 g (60%) of the title compound. The product could be solidified by evaporation from methylene chloride and subsequent freezing. $^1$H-NMR ($CDCl_3$/TMS): d=1.43 (s, 9H, $Me_3C$), 3.25 (m, 2H, $CH_2$), 3.57 (m, 2H, $CH_2$), 3.73 (m, 1H, CH). $^{13}$C-NMR ($CDCl_3$/TMS): d=28.2 ($Me_3C$), 42.6 ($CH_2$), 63.5, 71.1 ($CH_2OH$, CHOH), 79.5 ($Me_3C$), 157.0 (C=O).

EXAMPLE 49

2-(Boc-amino)ethyl-L-alanine methyl ester

3-Boc-amino-1,2-propanediol (20.76 g, 0.109 mol, 1 eq.) was suspended in water (150 ml). Potassium m-periodate (24.97 g, 0.109 mol, 1 eq.) was added and the reaction mixture was stirred for 2 h at room temperature under nitrogen. The reaction mixture was filtered and the water phase extracted with chloroform (6×250 ml) The organic phase was dried ($MgSO_4$) and evaporated to afford an almost quantitative yield of Boc-aminoacetaldehyde as a colourless oil, which was used without further purification in the following procedure.

Palladium-on-carbon (10%, 0.8 g) was added to MeOH (250 ml) under nitrogen with cooling (0° C.) and vigorous stirring. Anhydrous sodium acetate (4.49 g, 54.7 mmol, 2 eqv) and L-alanine methyl ester, hydrochloride (3.82 g, 27.4 mmol, 1 eqv) were added. Boc-aminoacetaldehyde (4.79 g, 30.1 mmol, 1.1 eqv) was dissolved in MeOH (150 ml) and added to the reaction mixture. The reaction mixture was hydrogenated at atmospheric pressure and room temperature until hydrogen uptake had ceased. The reaction mixture was filtered through celite, which was washed with additional MeOH. The MeOH was removed under reduced pressure. The residue was suspended in water (150 ml) and pH adjusted to 8.0 by dropwise addition of 0.5 N NaOH with vigorous stirring. The water phase was extracted with methylene chloride (4×250 ml). The organic phase was dried ($MgSO_4$), filtered through celite, and evaporated under reduced pressure to yield 6.36 g (94%) of the title compound as a clear, slightly yellow oil. MS (FAB-MS): m/z (%)=247 (100, M+1, 191 (90), 147 (18). $^1$H-NMR (250 MHz, $CDCl_3$). 1.18 (d, J=7.0 Hz, 3H, Me), 1.36 (s, 9H, $Me_3C$), 1.89 (b, 1H, NH), 2.51 (m, 1H, $CH_2$), 2.66 (m, 1H, $CH_2$), 3.10 (m, 2H, $CH_2$), 3.27 (q, J=7.0 Hz, 1H, CH), 3.64 (s, 3H, OMe), 5.06 (b, 1H, carbamate NH). $^{13}$C-NMR. d=18.8 (Me), 28.2 ($Me_3C$), 40.1, 47.0 ($CH_2$), 51.6 (OMe), 56.0 (CH), 155.8 (carbamate C=O), 175.8 (ester C=O).

EXAMPLE 50

N-(Boc-aminoethyl)-N-(1-thyminylacetyl)-L-alanine methyl ester

To a solution of Boc-aminoethyl-(L)-alanine methyl ester (1.23 g, 5.0 mmol) in DMF (10 ml) was added Dhbt-OH (0.90 g, 5.52 mmol) and 1-thyminylacetic acid (1.01 g, 5.48 mmol). When the 1-thyminylacetic acid was dissolved, dichloromethane (10 ml) was added and the solution was cooled on an ice bath. After the reaction mixture had reached 0° C., DCC (1.24 g, 6.01 mmol) was added. Within 5 min after the addition, a precipitate of DCU was seen. After a further 5 min, the ice bath was removed. Two hours later, TLC analysis showed the reaction to be finished. The mixture was filtered and the precipitate washed with dichloromethane (100 ml). The resulting solution was extracted twice with 5% sodium hydrogen carbonate (150 ml) and twice with saturated potassium hydrogen sulfate (25 ml) in water (100 ml). After a final extraction with saturated sodium chloride (150 ml), the solution was dried with magnesium sulfate and evaporated to give a white foam. The foam was purified by column chromatography on silica gel using dichloromethane with a methanol gradient as eluent. This yielded a pure compound (>99% by HPLC) (1.08 g, 52.4%) FAB-MS: 413 (M+1) and 431 (M+1+water). $^1$H-NMR ($CDCl_3$): 4.52 (s, 2 H, CH'$_2$); 3.73 (s, 3 H, OMe); 3.2–3.6 (m, 4 H, ethyl $CH_2$'s); 1.90 (s, 3 H, Me in T); 1.49 (d, 3 H, Me in Ala, J=7.3 Hz); 1.44 (s, 9 H, Boc).

EXAMPLE 51

N-(Boc-aminoethyl)-N-(1-thyminylacetyl)-L-alanine

The methyl ester of the title compound (2.07 g, 5.02 mmol) was dissolved in methanol (100 ml), and cooled on an ice bath. 2 M sodium hydroxide (100 ml) was added. After stirring for 10 min, the pH of the mixture was adjusted to 3 with 4 M hydrogen chloride. The solution was subsequently extracted with ethyl acetate (3×100 ml). The combined organic extracts were dried over magnesium sulfate. After evaporation, the resulting foam was dissolved in ethyl acetate (400 ml) and a few ml of methanol to dissolve the solid material. Petroleum ether then was added until precipitation started. After standing overnight at −20° C., the precipitate was removed by filtration. This gave 1.01 g (50.5%) of pure compound (>99% by HPLC). The compound can be recrystallized from 2-propanol. FAB-MS: 399 (M+1). $^1$H-NMR (DMSO-$d_6$): 11.35 (s, 1 H, COO); 7.42 (s, 1 H, H'$_6$); 4.69 (s, 2 H, CH'$_2$); 1.83 (s, 3 H, Me in T); 1.50–1.40 (m, 12 H, Me in Ala+Boc).

EXAMPLE 52

(a) N-(Boc-aminoethyl)-N-(1-thyminylacetyl)-D-alanine methyl ester

To a solution of Boc-aminoethyl alanine methyl ester (2.48 g, 10.1 mmol) in DMF (20 ml) was added Dhbt-OH (1.80 g, 11.0 mmol) and thyminylacetic acid (2.14 g, 11.6 mmol). After dissolution of the 1-thyminylacetic acid, methylene chloride (20 ml) was added and the solution cooled on an ice bath. When the reaction mixture had reached 0° C., DCC (2.88 g, 14.0 mmol) was added. Within 5 min after the addition a precipitate of DCU was seen. After 35 min the ice bath was removed. The reaction mixture was filtered 3.5 h later and the precipitate washed with methylene chloride (200 ml). The resulting solution was extracted twice with 5% sodium hydrogen carbonate (200 ml) and twice with saturated potassium hydrogen sulfate in water (100 ml). After a final extraction with saturated sodium chloride (250 ml), the solution was dried with magnesium sulfate and evaporated to give an oil. The oil was purified by short column silica gel chromatography using methylene chloride with a methanol gradient as eluent. This yielded a compound which was 96% pure according to HPLC (1.05 g, 25.3%)

after precipitation with petroleum ether. FAB-MS: 413 (M+1). $^1$H-NMR (CDCl$_3$): 5.64 (t, 1 H, BocNH, J=5.89 Hz); 4.56 (d, 2 H, CH'$_2$); 4.35 (q, 1 H, CH in Ala, J=7.25 Hz); 3.74 (s, 3 H, OMe); 3.64–3.27 (m, 4 H, ethyl H's); 1.90 (s, 3 H, Me in T); 1.52–1.44 (t, 12 H, Boc+Me in Ala).

(b) N-(Boc-aminoethyl)-N-(1-thyminylacetyl)-D-alanine

The methyl ester of the title compound (1.57 g, 3.81 mmol) was dissolved in methanol (100 ml) and cooled on an ice bath. Sodium hydroxide (100 ml; 2 M) was added. After stirring for 10 min the pH of the mixture was adjusted to 3 with 4 M hydrogen chloride. The solution then was extracted with ethyl acetate (3×100 ml). The combined organic extracts were dried over magnesium sulfate. After evaporation, the oil was dissolved in ethyl acetate (200 ml). Petroleum ether was added (to a total volume of 600 ml) until precipitation started. After standing overnight at −20° C., the precipitate was removed by filtration. This afforded 1.02 g (67.3%) of the title compound, which was 94% pure according to HPLC. FAB-MS: 399 (M+1). $^1$H-NMR: 11.34 (s, 1 H, COOH); 7.42 (s, 1 H, H'$_6$); 4.69 (s, 2 H, CH'$_2$); 4.40 (q, 1 H, CH in Ala, J=7.20 Hz); 1.83 (s, 3 H, Me in T); 1.52–1.40 (m, 12 H, Boc+Me in Ala).

EXAMPLE 53

N-(N'-Boc-3'-aminopropyl)-N-[(1-thyminyl)acetyl] glycine methyl ester

N-(N'-Boc-3'-aminopropyl)glycine methyl ester (2.84 g, 0.0115 mol) was dissolved in DMF (35 ml), followed by addition of DhbtOH (2.07 g, 0.0127 mol) and 1-thyminylacetic acid (2.34 g, 0.0127 mol). Methylene chloride (35 ml) was added and the mixture cooled to 0° C. on an ice bath. After addition of DCC (2.85 g, 0.0138 mol), the mixture was stirred at 0° C. for 2 h, followed by 1 h at room temperature. The precipitated DCU was removed by filtration, washed with methylene chloride (25 ml), and a further amount of methylene chloride (150 ml) was added to the filtrate. The organic phase was extracted with sodium hydrogen carbonate (1 volume saturated diluted with 1 volume water, 6×250 ml), potassium sulfate (1 volume saturated diluted with 4 volumes water, 3×250 ml), and saturated aqueous sodium chloride (1×250 ml), dried over magnesium sulfate, and evaporated to dryness, in vacuo. The solid residue was suspended in methylene chloride (35 ml) and stirred for 1 h. The precipitated DCU was removed by filtration and washed with methylene chloride (25 ml). The filtrate was evaporated to dryness, in vacuo, and the residue purified by column chromatography on silica gel, eluting with a mixture of methanol and methylene chloride (gradient from 3–7% methanol in methylene chloride). This afforded the title compound as a white solid (3.05 g, 64%). M.p. 76–79° C. (decomp.). Anal. for C$_{18}$H$_{28}$N$_4$O$_7$, found (calc.) C: 52.03 (52.42) H: 6.90 (6.84) N: 13.21 (13.58). The compound showed satisfactory $^1$H and $^{13}$C-NMR spectra.

EXAMPLE 54

N-(N'-Boc-3'-aminopropyl)-N-[(1-thyminyl)acetyl] glycine

N-(N'-Boc-3'-aminopropyl)-N-[(1-thyminyl)acetyl] glycine methyl ester (3.02 g, 0.00732 mol) was dissolved in methanol (25 ml) and stirred for 1.5 h with 2 M sodium hydroxide (25 ml). The methanol was removed by evaporation, in vacuo, and pH adjusted to 2 with 4 M hydrochloric acid at 0° C. The product was isolated as white crystals by filtration, washed with water (3×10 ml), and dried over sicapent, in vacuo. Yield 2.19 g (75%). Anal. for C$_{17}$H$_{26}$N$_4$O$_7$, H$_2$O, found (calc.) C: 49.95 (49.03) H: 6.47 (6.29) N: 13.43 (13.45). The compound showed satisfactory $^1$H and $^{13}$C-NMR spectra.

EXAMPLE 55

3-(1-Thyminyl)-propanoic acid methyl ester

Thymine (14.0 g, 0.11 mol) was suspended in methanol. Methyl acrylate (39.6 ml, 0.44 mol) was added, along with catalytic amounts of sodium hydroxide. The solution was refluxed in the dark for 45 h, evaporated to dryness, in vacuo, and the residue dissolved in methanol (8 ml) with heating. After cooling on an ice bath, the product was precipitated by addition of ether (20 ml), isolated by filtration, washed with ether (3×15 ml), and dried over sicapent, in vacuo. Yield 11.23 g (48%). M.p. 112–119° C. Anal. for C$_9$H$_{12}$N$_2$O$_4$, found (calc.) C: 51.14 (50.94) H: 5.78 (5.70) N: 11.52 (13.20). The compound showed satisfactory $^1$H and $^{13}$C-NMR spectra.

EXAMPLE 56

3-(1-Thyminyl)-propanoic acid 3-(1-Thyminyl)-propanoic acid methyl ester (1.0 g, 0.0047 mol) was suspended in 2 M sodium hydroxide (15 ml), boiled for 10 min. The pH was adjusted to 0.3 with conc. hydrochloric acid. The solution was extracted with ethyl acetate (10×25 ml). The organic phase was extracted with saturated aqueous sodium chloride, dried over magnesium sulfate, and evaporated to dryness, in vacuo, to give the title compound as a white solid (0.66 g, 71%). M.p. 118–121° C. Anal. for C$_8$H$_{10}$N$_2$O$_4$, found (calc.) C: 48.38 (48.49) H: 5.09 (5.09) N: 13.93 (14.14). The compound showed satisfactory $^1$H and $^{13}$C-NMR spectra.

EXAMPLE 57

N-(N'-Boc-aminoethyl)-N-[(1-thyminyl)propanoyl] glycine ethyl ester

N-(N'-Boc-aminoethyl)glycine ethyl ester (1.0 g, 0.0041 mol) was dissolved in DMF (12 ml). DhbtOH (0.73 g, 0.0045 mol) and 3-(1-thyminyl)-propanoic acid (0.89 g, 0.0045 mol) were added. Methylene chloride (12 ml) then was added and the mixture was cooled to 0° C. on an ice bath. After addition of DCC (1.01 g, 0.0049 mol), the mixture was stirred at 0° C. for 2 h, followed by 1 h at room temperature. The precipitated DCU was removed by filtration, washed with methylene chloride (25 ml), and a further amount of methylene chloride (50 ml) was added to the filtrate. The organic phase was extracted with sodium hydrogen carbonate (1 volume saturated diluted with 1 volume water, 6×100 ml), potassium sulfate (1 volume saturated diluted with 4 volumes water, 3×100 ml), and saturated aqueous sodium chloride (1×100 ml), dried over magnesium sulfate, and evaporated to dryness, in vacuo. The solid residue was suspended in methylene chloride (15 ml), and stirred for 1 h. The precipitated DCU was removed by filtration and washed with methylene chloride. The filtrate was evaporated to dryness, in vacuo, and the residue purified by column chromatography on silica gel, eluting with a mixture of methanol and methylene chloride (gradient from 1 to 6% methanol in methylene chloride). This afforded the title compound as a white solid (1.02 g, 59%). Anal. for C$_{19}$H$_{30}$N$_4$O$_7$, found (calc.) C: 53.15 (53.51) H: 6.90 (7.09) N: 12.76 (13.13). The compound showed satisfactory $^1$H and $^{13}$C-NMR spectra.

EXAMPLE 58

N-(N'-Boc-aminoethyl)-N-[(1-thyminyl)propanoyl] glycine

N-(N'-Boc-aminoethyl)-N-[(1-thyminyl)propanoyl] glycine ethyl ester (0.83 g, 0.00195 mol) was dissolved in methanol (25 ml). Sodium hydroxide (25 ml; 2 M) was added. The solution was stirred for 1 h. The methanol was removed by evaporation, in vacuo, and the pH adjusted to 2 with 4 M hydrochloric acid at 0° C. The product was isolated by filtration, washed with ether (3×15 ml), and dried over sicapent, in vacuo. Yield 0.769 g, 99%). M.p. 213° C. (de-comp.).

EXAMPLE 59

Mono-Boc-ethylenediamine (2).

tert-Butyl-4-nitrophenyl carbonate (1) (10.0 g; 0.0418 mol) dissolved in DMF (50 ml) was added dropwise over a period of 30 min to a solution of ethylenediamine (27.9 ml; 0.418 mol) and DMF (50 ml) and stirred overnight. The mixture was evaporated to dryness, in vacuo, and the resulting oil dissolved in water (250 ml). After cooling to 0° C., pH was adjusted to 3.5 with 4 M hydrochloric acid. The solution then was filtered and extracted with chloroform (3×250 ml). The pH was adjusted to 12 at 0° C. with 2 M sodium hydroxide, and the aqueous solution extracted with methylene chloride (3×300 ml). After treatment with sat. aqueous sodium chloride (250 ml), the methylene chloride solution was dried over magnesium sulfate. After filtration, the solution was evaporated to dryness, in vacuo, resulting in 4.22 g (63%) of the product (oil). $^1$H-NMR (90 MHz; CDCl$_3$): δ1.44 (s, 9H); 2.87 (t, 2H); 3.1 (q, 2H); 5.62 (s, broad)

EXAMPLE 60

(N-Boc-aminoethyl)-β-alanine methyl ester, HCl

Mono-Boc-ethylenediamine (2) (16.28 g; 0.102 mol) was dissolved in acetonitrile (400 ml) and methyl acrylate (91.50 ml; 1.02 mol) was transferred to the mixture with acetonitrile (200 ml). The solution was refluxed overnight under nitrogen in the dark to avoid polymerization of methyl acrylate. After evaporation to dryness, in vacuo, a mixture of water and ether (200+200 ml) was added, and the solution was filtered and vigorously stirred. The aqueous phase was extracted one more time with ether and then freeze dried to yield a yellow solid. Recrystallization from ethyl acetate yielded 13.09 g (46%) of the title compound. M.p. 138–140° C. Anal. for C$_{11}$H$_{23}$N$_2$O$_4$Cl, found (calc.) C: 46.49 (46.72) H: 8.38 (8.20) N: 9.83 (9.91) Cl: 12.45 (12.54). $^1$H-NMR (90 MHz; DMSO-d$_6$): δ 1.39 (s, 9H); 2.9 (m, 8H); 3.64 (s, 3H).

EXAMPLE 61

N-[(1-Thyminyl)acetyl]-N'-Boc-aminoethyl-β-alanine methyl ester (N-Boc-amino-ethyl)-β-alanine methyl ester, HCl (3) (2.0 g; 0.0071 mol) and 1-thyminylacetic acid pentafluorophenyl ester (5) (2.828 g; 0.00812 mol) were dissolved in DMF (50 ml). Triethyl amine (1.12 ml; 0.00812 mol) was added and the mixture stirred overnight. After addition of methylene chloride (200 ml) the organic phase was extracted with aqueous sodium hydrogen carbonate (3×250 ml), half-sat. aqueous potassium hydrogen sulfate (3×250 ml), and sat. aqueous sodium chloride (250 ml) and dried over magnesium sulfate. Filtration and evaporation to dryness, in vacuo, resulted in 2.9 g (99%) yield (oil). $^1$H-NMR (250 MHz; CDCl$_3$): due to limited rotation around the secondary amide several of the signals were doubled; δ1.43 (s, 9H); 1.88 (s, 3H); 2.63 (t, 1H); 2.74 (t, 1H); 3.25–3.55 (4×t, 8H); 3.65 (2×t, 2H); 3.66 (s, 1.5); 3.72 (s, 1.5); 4.61 (s, 1H); 4.72 (s, 2H); 5.59 (s, 0.5H); 5.96 (s, 0.5H); 7.11 (s, 1H); 10.33 (s, 1H).

EXAMPLE 62

N-[(1-Thyminyl)acetyl]-N'-Boc-aminoethyl-β-alanine

N-[(1-Thyminyl)acetyl]-N'-Boc-aminoethyl-β-alanine methyl ester (3.0 g; 0.0073 mol) was dissolved in 2 M sodium hydroxide (30 ml), the pH adjusted to 2 at 0° C. with 4 M hydrochloric acid, and the solution stirred for 2 h. The precipitate was isolated by filtration, washed three times with cold water, and dried over sicapent, in vacuo. Yield 2.23 g (77%). M.p. 170–176° C. Anal. for C$_{17}$H$_{26}$N$_4$O$_7$, H$_2$O, found (calc.) C: 49.49 (49.03) H: 6.31 (6.78) N: 13.84 (13.45). $^1$H-NMR (90 MHz; DMSO-d$_6$): δ1.38 (s, 9H); 1.76 (s, 3H); 2.44 and 3.29 (m, 8H); 4.55 (S, 2H); 7.3 (s, 1H); 11.23 (s, 1H). FAB-MS: 399 (M+1).

EXAMPLE 63

N-[(1-(N$^4$-Z)-cytosyl)acetyl]-N'-Boc-aminoethyl-β-alanine methyl ester (N-Boc-amino-ethyl)-β-alanine methyl ester, HCl (3) (2.0 g; 0.0071 mol) and 1-(N-4-Z)-cytosylacetic acid pentafluorophenyl ester (5) (3.319 g; 0.0071 mol) were dissolved in DMF (50 ml). Triethyl amine (0.99 ml; 0.0071 mol) was added and the mixture stirred overnight. After addition of methylene chloride (200 ml), the organic phase was extracted with aqueous sodium hydrogen carbonate (3×250 ml), half-sat. aqueous potassium hydrogen sulfate (3×250 ml), and sat. aqueous sodium chloride (250 ml), and dried over magnesium sulfate. Filtration and evaporation to dryness, in vacuo, resulted in 3.36 g of solid compound which was recrystallized from methanol. Yield 2.42 g (64%). M.p. 158–161° C. Anal. for C$_{25}$H$_{33}$N$_5$O$_8$, found (calc.) C: 55.19 (56.49) H: 6.19 (6.26) N: 12.86 (13.18). $^1$H-NMR (250 MHz; CDCl$_3$): due to limited rotation around the secondary amide several of the signals were doubled; δ1.43 (s, 9H); 2.57 (t, 1H); 3.60–3.23 (m's, 6H); 3.60 (s, 1,5H); 3.66 (s, 1.5H); 4.80 (s, 1H); 4.88 (s, 1H); 5.20 (s, 2H); 7.80–7.25 (m's, 7H). FAB-MS: 532 (M+1).

EXAMPLE 64

N-[(1-(N$^4$-Z)-cytosyl)acetyl]-N'-Boc-aminoethyl-β-alanine

N-[(1-(N-4-Z)-cytosyl)acetyl]-N'-Boc-aminoethyl-β-alanine methyl ester (0.621 g; 0.0012 mol) was dissolved in 2 M sodium hydroxide (8.5 ml) and stirred for 2 h. Subsequently, pH was adjusted to 2 at 0° C. with 4 M hydrochloric acid and the solution stirred for 2 h. The precipitate was isolated by filtration, washed three times with cold water, and dried over sicapent, in vacuo. Yield 0.326 g (54%). The white solid was recrystallized from 2-propanol and washed with petroleum ether. Mp.163° C. (decomp.). Anal. for C$_{24}$H$_{31}$N$_5$O$_8$, found (calc.) C: 49.49 (49.03) H: 6.31 (6.78) N: 13.84 (13.45). $^1$H-NMR (250 MHz; CDCl$_3$): due to limited rotation around the secondary amide several of the signals were doubled; δ1.40 (s, 9H); 2.57 (t, 1H); 2.65 (t, 1H); 3.60–3.32 (m's, 6H); 4.85 (s, 1H); 4.98 (s, 1H); 5.21 (s, 2H); 5.71 (s, 1H, broad); 7.99–7.25 (m's, 7H). FAB-MS: 518 (M+1).

EXAMPLE 65

Example of a PNA-Oligomer with a Guanine Residue (a) Solid-Phase Synthesis of H-[Taeg]$_5$-[Gaeg]-[Taeg]$_4$-Lys-NH$_2$ The protected PNA was assembled onto a Boc-Lys(ClZ) modified MBHA resin with a substitution of approximately 0.15 mmol/g (determined by quantitative Ninhydrin reaction). Capping of uncoupled amino groups was only carried out before the incorporation of the BocGaeg-OH monomer.

(b) Stepwise Assembly of H-[Taeg]$_5$-[Gaeg]-[Taeg]$_4$-Lys-NH$_2$ (Synthetic Protocol)

Synthesis was initiated on 102 mg (dry weight) of pre-swollen (overnight in DCM) and neutralized Boc-Lys (ClZ)-MBHA resin. The steps performed were as follows: (1) Boc-deprotection with TFA/DCM (1:1, v/v), 1×2 min and 1×½h, 3 ml; (2) washing with DCM, 4×20 sec, 3 ml; washing with DMF, 2×20 sec, 3 ml; washing with DCM, 2×20 sec, 3 ml, and drain for 30 sec; (3) neutralization with DIEA/DCM (1:19 v/v), 2×3 min, 3 ml; (4) washing with DCM, 4×20 sec, 3 ml, and drain for 1 min.; (5) addition of 4 equiv. diisopropyl carbodiimide (0.06 mmol; 9.7 μl) and 4 equiv. (0.06 mmol; 24 mg) BocTaeg-OH or (0.06 mmol; 30 mg) BocGaeg-OH dissolved in 0.6 ml DCM/DMF (1:1, v/v) (final concentration of monomer 0.1 M), the coupling reaction was allowed to proceed for ½ h shaking at room temperature; (6) drain for 20 sec; (7) washing with DMF, 2×20 sec and 1×2 min, 3 ml; washing with DCM 4×20 sec, 3 ml; (8) neutralization with DIEA/DCM (1:19 v/v), 2×3 min, 3 ml; (9) washing with DCM 4×20 sec, 3 ml, and drain for 1 min.; (10) qualitative Kaiser test; (11) blocking of unreacted amino groups by acetylation with Ac$_2$O/pyridine/DCM (1:1:2, v/v/v), 1×½ h, 3 ml; and (12) washing with DCM, 4×20 sec, 2×2 min and 2×20 sec. 3 ml. Steps 1–12 were repeated until the desired sequence was obtained. All qualitative Kaiser tests were negative (straw-yellow colour with no coloration of the beads) indicating near 100% coupling yield. The PNA-oligomer was cleaved and purified by the normal procedure. FAB-MS: 2832.11 [M*+1] (calc. 2832.15)

EXAMPLE 66

Solid-Phase Synthesis of H-Taeg-Aaeg-[Taeg]$_8$-Lys-NH$_2$ (a) Stepwise Assembly of Boc-Taeg-A(Z)aeg-[Taeg]$_8$-Lys (ClZ)-MBHA Resin About 0.3 g of wet Boc-[Taeg]$_8$-Lys(ClZ)-MBHA resin was placed in a 3 ml SPPS reaction vessel. Boc-Taeg-A(Z)aeg-[Taeg]$_8$-Lys(ClZ)-MBHA resin was assembled by in situ DCC coupling (single) of the A(Z)aeg residue utilizing 0.19 M of BocA(Z)aeg-OH together with 0.15 M DCC in 2.5 ml 50% DMF/CH$_2$Cl$_2$ and a single coupling with 0.15 M BocTaeg-OPfp in neat CH$_2$Cl$_2$ ("Synthetic Protocol 5"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-NH$_2$ The protected Boc-Taeg-A(Z)aeg-[Taeg]$_8$-Lys(ClZ)-BAH resin was treated as described in Example 27c to yield about 15.6 mg of crude material upon HF cleavage of 53.1 mg dry H-Taeg-A(Z)aeg-[Taeg]$_8$-Lys(ClZ)-BHA resin. The main peak at 14.4 min accounted for less than 50% of the total absorbance. A 0.5 mg portion of the crude product was purified to give approximately 0.1 mg of H-Taeg-Aaeg-[Taeg]$_8$-Lys-NH$_2$. For (MH+)* the calculated m/z value was 2816.16 and the measured m/z value was 2816.28.

(c) Synthetic Protocol 5

(1) Boc-deprotection with TFA/CH$_2$Cl$_2$ (1:1, v/v), 2.5 ml, 3×1 min and 1×30 min; (2) washing with CH$_2$Cl$_2$, 2.5 ml, 6×1 min; (3) neutralization with DIEA/CH$_2$Cl$_2$ (1: 19, v/v), 2.5 ml, 3×2 min; (4) washing with CH$_2$Cl$_2$, 2.5 ml, 6×1 min, and drain for 1 min; (5) 2–5 mg sample of PNA-resin is taken out and dried thoroughly for a quantitative ninhydrin analysis to determine the substitution; (6) addition of 0.47 mmol (0.25 g) BocA(Z)aeg-OH dissolved in 1.25 ml DMF followed by addition of 0.47 mmol (0.1 g) DCC in 1.25 ml CH$_2$Cl$_2$ or 0.36 mmol (0.20 g) BocTaeg-OPfp in 2.5 ml CH$_2$Cl$_2$; the coupling reaction was allowed to proceed for a total of 20–24 hrs shaking; (7) washing with DMF, 2.5 ml, 1×2 min; (8) washing with CH$_2$Cl$_2$, 2.5 ml, 4×1 min; (9) neutralization with DIEA/CH$_2$Cl$_2$ (1: 19, v/v), 2.5 ml, 2×2 min; (10) washing with CH$_2$Cl$_2$, 2.5 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the last cycle); and (13) washing with CH$_2$Cl$_2$, 2.5 ml, 6×1 min; (14) 2×2–5 mg samples of protected PNA-resin are taken out, neutralized with DIEA/CH$_2$Cl$_2$ (1: 19, v/v) and washed with CH$_2$Cl$_2$ for ninhydrin analyses.

EXAMPLE 67

Solid-Phase Synthesis of H-[Taeg]$_2$-Aaeg-[Taeg]$_5$-Lys-NH$_2$ (a) Stepwise Assembly of Boc-[Taeg]$_2$-A(Z)aeg-[Taeg]$_5$-Lys (ClZ) -MBHA Resin About 0. 5 g of wet Boc-[Taeg]$_5$-Lys(ClZ)-MBHA resin was placed in a 5 ml SPPS reaction vessel. Boc-[Taeg]$_2$-A(Z)aeg-[Taeg]$_5$-Lys(ClZ)-MBHA resin was assembled by in situ DCC coupling of both the A(Z)aeg and the Taeg residues utilising 0.15 M to 0.2 M of protected PNA monomer (free acid) together with an equivalent amount of DCC in 2 ml neat CH$_2$Cl$_2$ ("Synthetic Protocol 6"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/CH2Cl2 did not increase the total coupling yield significantly) and quantitative incorporation (single couplings) of the Taeg residues.

(b) Cleavage, Purification, and Identification of H-[Taeg]$_2$-Aaeg- [Taeg]$_5$-Lys-NH$_2$ The protected Boc-[Taeg]$_2$-A(Z)aeg-[Taeg]$_5$-Lys(ClZ)-BHA resin was treated as described in Example 27c to yield about 16.2 mg of crude material upon HF cleavage of 102.5 mg dry H-[Taeg]$_2$-A(Z)aeg-[Taeg]$_5$-Lys(ClZ)-BHA resin. A small portion of the crude product was purified. For (MH+)*, the calculated m/z value was 2050.85 and the measured m/z value was 2050.90

(c) Synthetic Protocol 6

(1) Boc-deprotection with TFA/CH$_2$Cl$_2$ (1:1, v/v) , 2 ml, 3×1 min and 1×30 min; (2) washing with CH$_2$Cl$_2$, 2 ml, 6×1 min; (3) neutralization with DIEA/CH$_2$Cl$_2$ (1: 19, v/v), 2 ml, 3×2 min; (4) washing with CH$_2$Cl$_2$, 2 ml, 6×1 min, and drain for 1 min; (5) 2–5 mg sample of PNA-resin was taken out and dried thoroughly for a quantitative ninhydrin analysis to determine the substitution; (6) addition of 0.44 mmol (0.23 g) BocA(Z)aeg-OH dissolved in 1.5 ml CH$_2$Cl$_2$ followed by addition of 0.44 mmol (0.09 g) DCC in 0.5 ml CH$_2$Cl$_2$ or 0.33 mmol (0.13 g) BocTaeg-OH in 1.5 ml CH$_2$Cl$_2$ followed by addition of 0.33 mmol (0.07 g) DCC in 0.5 ml CH$_2$Cl$_2$,; the coupling reaction was allowed to proceed for a total of 20–24 hrs with shaking; (7) washing with DMF, 2 ml, 1×2 min; (8) washing with CH$_2$Cl$_2$, 2 ml, 4×1 min; (9) neutralization with DIEA/CH$_2$Cl$_2$ (1: 19, v/v), 2 ml, 2×2 min; (10) washing with CH$_2$Cl$_2$, 2 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/ pyridine/CH$_2$Cl$_2$ (1:1:2, v/v/v) for 2 h (except after the last cycle); (13) washing with CH$_2$Cl$_2$, 2 ml, 6×1 min; and (14) 2×2–5 mg samples of protected PNA-resin were taken out, neutralized with DIEA/CH$_2$Cl$_2$ (1: 19, v/v) and washed with CH$_2$Cl$_2$ for ninhydrin analyses.

EXAMPLE 68

The PNA-oligomer H-T$_4$C$_2$TCTC-LysNH$_2$ (SEQ ID NO:11) was prepared as described in Example 103. Hybridization experiments with this sequence should resolve the issue of orientation, since it is truly asymmetrical. Such experiments should also resolve the issues of pH-dependency of the Tm, and the stoichiometry of complexes formed.

Hybridization experiments with the PNA-oligomer H-T$_4$C$_2$TCTC-LysNH$_2$ were performed as follows:

| Row | Hybridized With | pH | Tm | § |
|---|---|---|---|---|
| 1 | 5'-(dA)$_4$(dG)$_2$(dA)(dG)(dA)(dG) | 7.2 | 55.5 | 2:1 |
| 2 | 5'-(dA)$_4$(dG)$_2$(dA)(dG)(dA)(dG) | 9.0 | 26.0 | 2:1 |
| 3 | 5'-(dA)$_4$(dG)$_2$(dA)(dG)(dA)(dG) | 5.0 | 88.5 | 2:1 |
| 4 | 5'-(dG)(dA)(dG)(dA)(dG)$_2$(dA)$_4$ | 7.2 | 38.0 | 2:1 |
| 5 | 5'-(dG)(dA)(dG)(dA)(dG)$_2$(dA)$_4$ | 9.0 | 31.5 | — |
| 6 | 5'-(dG)(dA)(dG)(dA)(dG)$_2$(dA)$_4$ | 5.0 | 52.5 | — |
| 7 | 5'-(dA)$_4$(dG)(dT)(dA)(dG)(dA)(dG) | 7.2 | 39.0 | — |
| 8 | 5'-(dA)$_4$(dG)(dT)(dA)(dG)(dA)(dG) | 9.0 | <20 | — |
| 9 | 5'-(dA)$_4$(dG)(dT)(dA)(dG)(dA)(dG) | 5.0 | 51.5 | — |
| 10 | 5'-(dA)$_4$(dG)$_2$(dT)(dG)(dA)(dG) | 7.2 | 31.5 | — |
| 11 | 5'-(dA)$_4$(dG)$_2$(dT)(dG)(dA)(dG) | 5.0 | 50.5 | — |
| 12 | 5'-(dG)(dA)(dG)(dA)dT)(dG)(dA)$_4$ | 7.2 | 24.5 | — |
| 13 | 5'-(dG)(dA)(dG)(dA)dT)(dG)(dA)$_4$ | 9.0 | <20 | — |
| 14 | 5'-(dG)(dA)(dG)(dA)dT)(dG)(dA)$_4$ | 5.0 | 57.0 | — |
| 15 | 5'-(dG)(dA)(dG)(dT)(dG)$_2$(dA)$_4$ | 7.2 | 25.0 | — |
| 16 | 5'-(dG)(dA)(dG)(dT)(dG)$_2$(dA)$_4$ | 5.0 | 39.5 | — |
|  |  |  | 52.0 |  |

§ = stoichiometry determined by UV-mixing curves
— = not determined

These results show that a truly mixed sequence gave rise to well defined melting curves. The PNA-oligomers can actually bind in both orientations (compare row 1 and 4), although there is preference for the N-terminal/5'-orientation. Introducing a single mismatch opposite either T or C caused a lowering of T$_m$ by more than 16° C. at pH 7.2; at pH 5.0 the T$_m$-value was lowered more than 27° C. This shows that there is a very high degree a sequence-selectivity which should be a general feature for all PNA C/T sequences.

As indicated above, there is a very strong pH-dependency for the T$_m$-value, indicating that Hoogsteen basepairing is important for the formation of hybrids. Therefore, it is not surprising that the stoichiometry was found to be 2:1.

The lack of symmetry in the sequence and the very large lowering of T$_m$ when mismatches are present show that the Watson-Crick strand and the Hoogsteen strand are parallel when bound to complementary DNA. This is true for both of the orientations, i.e., 5'/N-terminal and 3'/N-terminal.

EXAMPLE 69

The results of hybridization experiments with H-T$_5$GT$_4$-LysNH$_2$ to were performed as follows:

| Row | Deoxyoligonucleotide | Tm |
|---|---|---|
| 1 | 5'-(dA)5(dA)(dA)4-3' | 55.0 |
| 2 | 5'-(dA)5(dG)(dA)4-3' | 47.0 |
| 3 | 5'-(dA)5(dG)(dA)4-3' | 56.5 |
| 4 | 5'-(dA)5(dT)(dA)4-3' | 46.5 |
| 5 | 5'-(dA)4(dA)(dA)5-3' | 48.5 |
| 6 | 5'-(dA)4(dC)(dA)5-3' | 55.5 |
| 7 | 5'-(dA)4(dT)(dA)5-3' | 47.0 |

As shown by comparing rows 1, 3, and 6 with rows 2, 4, 5, and 7, G can in this mode discriminate between C/A and G/T in the DNA-strand, i.e., sequence discrimination is observed. The complex in row 3 was furthermore determined to be 2 PNA: 1 DNA complex by UV-mixing curves.

EXAMPLE 70

The masses of some synthesized PNA-oligomers, as determined by FAB mass spectrometry, are as follows:

| SEQUENCE | CALC. | FOUND |
|---|---|---|
| H-T$_4$C$_2$TCTC-LysNH$_2$ | 2747.15 | 2746.78 |
| H-T$_5$GT$_4$-LysNH$_2$ | 2832.15 | 2832.11 |
| H-T$_7$-LysNH$_2$ | 2008.84 | 2540.84 |
| H-T$_9$-LysNH$_2$ | 2541.04 | 2540.84 |
| H-T$_{10}$-LysNH$_2$ | 2807.14 | 2806.69 |
| H-T$_2$CT$_5$-LysNH$_2$ | 2259.94 | 2259.18 |
| H-T$_3$(L-alaT)T$_4$-LysNH$_2$ | 2287.95 | 2288.60 |
| H-T$_4$(Ac)T$_5$-LysNH$_2$ | 2683.12 | 2683.09 |

EXAMPLE 71

Hybridization data for a PNA-oligomer with a single unit with an extended backbone (the β-alanine modification) is as follows:

| PNA | DNA | T$_m$ |
|---|---|---|
| H-T$_{10}$-LysnH$_2$ | (dA)$_{10}$ | 73° C. |
| H-T$_4$(βT)T$_5$-LysNH$_2$ | (dA)$_{10}$ | 57° C. |
| H-T$_4$(βT)T$_5$-LysNH$_2$ | (dA)$_4$(dG)(dA)$_5$ | 47° C. |
| H-T$_4$(βT)T$_5$-LysNH$_2$ | (dA)$_4$(dT)(dA)$_5$ | 49° C. |
| H-T$_4$(βT)T$_5$-LysNH$_2$ | (dA)$_4$(dT)(dA)$_5$ | 47° C. |

Although the melting temperature decreases, the data demonstrates that base specific recognition is retained.

EXAMPLE 72

An example with a "no base" substitution.

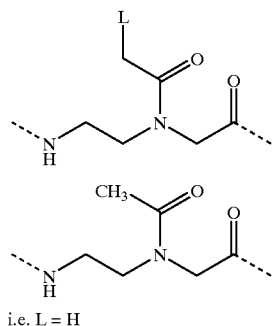

i.e. L = H

| PNA | DNA | $T_m$ |
|---|---|---|
| H-$T_{10}$-LysNH$_2$ | (dA)$_{10}$ | 73° C. |
| H-$T_4$(Ac)$T_5$-LysNH$_2$ | (dA)$_{10}$ | 49° C. |
| H-$T_4$(AC)$T_5$-LysNH$_2$ | (dA)$_4$(dG)(dA)$^5$ | 37° C. |
| H-$T_4$(Ac)$T_5$-LysNH$_2$ | (dA)$_4$(dC)(dA)$^5$ | 41° C. |
| H-$T_4$(Ac)$T_5$-LysNH$_2$ | (dA)$_4$(dT)(dA)$^5$ | 41° C. |
| H-$T_4$(AC)$T_5$-LysNH$_2$ | (dA)$_5$(dG)(dA)$^4$ | 36° C. |
| H-$T_4$(AC)$T_5$-LysNH$_2$ | (dA)$_5$(dC)(dA)$^4$ | 40° C. |
| H-$T_4$(AC)$T_5$-LysNH$_2$ | (dA)$_5$(dT)(dA)$^4$ | 40° C. |

EXAMPLE 73

Iodination Procedure

A 5 µg portion of Tyr-PNA-$T_{10}$-Lys-NH$_2$ is dissolved in 40 µl 100 mM Na-phosphate, pH 7.0, and 1 mCi Na$^{125}$I and 2 µl chloramine-T (50 mM in CH$_3$CN) are added. The solution is left at 20° C. for 10 min and then passed through a 0.5+5 cm Sephadex G10 column. The first 2 fractions (100 µl each) containing radioactivity are collected and purified by HPLC: reversed phase C-18 using a 0–60% CH$_3$CN gradient in 0.1% CF$_3$COOH in H$_2$O. The $^{125}$I-PNA elutes right after the PNA peak. The solvent is removed under reduced pressure.

EXAMPLE 74

Binding of PNAs-$T_{10}$/$T_9$C/$T_8$C$_2$ to Double Stranded DNA Targets $A_{10}$/$A_9$G/$A_8$G$_2$ (FIG. 13)

A mixture of 200 cps $^{32}$P-labeled EcoRI-PvuII fragment (the large fragment labeled at the 3'-end of the EcoRI site) of the indicated plasmid, 0.5 µg carrier calf thymus DNA, and 300 ng PNA in 100 µl buffer (200 mM NaCl, 50 mM Na-acetate, pH 4.5, 1 mM ZnSO$_4$) was incubated at 37° C. for 120 min. A 50 unit portion of nuclease S$_1$ was added and incubated at 20° C. for 5 min. The reaction was stopped by addition of 3 µl 0.5 M EDTA and the DNA was precipitated by addition of 250 µl 2% potassium acetate in ethanol. The DNA was analyzed by electrophoresis in 10% polyacrylamide sequencing gels and the radiolabeled DNA bands visualized by autoradiography.

The target plasmids were prepared by cloning of the appropriate oligonucleotides into pUC19. Target $A_{10}$: oligonucleotides GATCCA$_{10}$G & GATCCT$_{10}$G cloned into the BamHI site (plasmid designated pT10). Target $A_5$GA$_4$: oligonucleotides TCGACT$_4$CT$_5$G & TCGACA$_5$GA$_4$G cloned into the SalI site (plasmid pT9C). Target $A_2$GA$_2$GA$_4$: oligonucleotides GA$_2$GA$_2$GA$_4$TGCA & GT$_4$CT$_2$CT$_2$CTGCA into the PstI site (plasmid pT8C2). The positions of the targets in the gel are indicated by bars to the left. A/G is an A+G sequence ladder of target P10.

EXAMPLE 75

Inhibition of Restriction Enzyme Cleavage by PNA (FIG. 14)

A 2 µg portion of plasmid pT10 was mixed with the indicated amount of PNA-$T_{10}$ in 20 µl TE buffer (10 mM Tris-HCl, 1 mM EDTA, pH 7.4) and incubated at 37° C. for 120 min. 2 µl 10×buffer (10 mM Tris-HCl, pH 7.5, 10 mM, MgCl$_2$, 50 mM NaCl, 1 mM DTT). PvuII (2 units) and BamHI (2 units) were added and the incubation was continued for 60 min. The DNA was analyzed by gel electrophoresis in 5% polyacrylamide and the DNA was visualized by ethidium bromide staining.

EXAMPLE 76

Kinetics of PNA-$T_{10}$-dsDNA Strand Displacement Complex Formation (FIG. 15)

A mixture of 200 cps $^{32}$P-labeled EcoRI-PvuII fragment of pT10 (the large fragment labeled at the 3'-end of the EcoRI site), 0.5 µg carrier calf thymus DNA, and 300 ng of PNA-$T_{10}$-LysNH$_2$ in 100 µl buffer (200 mM NaCl, 50 mM Na-acetate, pH 4.5, 1 mM ZnSO$_4$) were incubated at 37° C. At the times indicated, 50 U of S$_1$ nuclease was added to each of 7 samples and incubation was continued for 5 min at 20° C. The DNA was then precipitated by addition of 250 µl 2% K-acetate in ethanol and analyzed by electrophoresis in a 10% polyacrylamide sequencing gel. The amount of strand displacement complex was calculated from the intensity of the S$_1$-cleavage at the target sequence, as measured by densitometric scanning of autoradiographs.

EXAMPLE 77

Stability of PNA-dsDNA Complexes (FIG. 16)

A mixture of 200 cps $^{32}$P-pT10 fragment, 0.5 µg calf thymus DNA and 300 ng of the desired PNA (either $T_{10}$-LysNH$_2$, $T_8$-LysNH$_2$ or $T_6$-LysNH$_2$) was incubated in 100 µl 200 mM NaCl, 50 mM Na-acetate, pH 4.5, 1 mM ZnSO$_4$ for 60 min at 37° C. A 2 µg portion of oligonucleotide GATCCA$_{10}$G was added and each sample was heated for 10 min at the temperature indicated, cooled in ice for 10 min and warmed to 20° C. A 50 U portion of S$_1$ nuclease was added and the samples treated and analyzed and the results quantified.

EXAMPLE 78

Inhibition of Transcription by PNA

A mixture of 100 ng plasmid DNA (cleaved with restriction enzyme PvuII (see below) and 100 ng of PNA in 15 µl 10 mM Tris-HCl, 1 mM EDTA, pH 7.4 was incubated at 37° C. for 60 min. Subsequently, 4 µl 5× concentrated buffer (0.2 M Tris-HCl (pH 8.0), 40 mM MgCl$_2$, 10 mM spermidine, 125 mM NaCl) were mixed with 1 µl NTP-mix (10 mM ATP, 10 mM CTP, 10 mM GTP, 1 MM UTP, 0.1 µCi/µl $^{32}$P-UTP, 5 mM DTT, 2 µg/ml tRNA, 1 µg/ml heparin) and 3 units RNA polymerase. Incubation was continued for 10 min at 37° C. The RNA was then precipitated by addition of 60 µl 2% postassium acetate in 96% ethanol at −20° C. and analyzed by electrophoresis in 8% polyacrylamide sequencing gels. RNA transcripts were visualized by autoradiography. The following plasmids were used: pT8C2-KS/pA8G2-KS: oligonucleotides $GA_2GA_2GA_4GTGAC$ & $GT_4CT_2CT_2CTGCA$ cloned into the PstI site of pBluescript-KS+; pT10-KS/pA10-KS (both orientations of the insert were obtained). pT10UV5: oligonucleotides $GATCCA_{10}G$ & $GATCCT_{10}G$ cloned into the BamHI site of a pUC18 derivative in which the lac UV5 E. coli promoter had been cloned into the EcoRI site (Jeppesen, et al., *Nucleic Acids Res.*, 1988, 16, 9545).

Using $T_3$-RNA polymerase, transcription elongation arrest was obtained with PNA-$T_8C_2$-LysNH$_2$ and the pA8G2-KS plasmid having the PNA recognition sequence on the template strand, but not with pT8C2-KS having the PNA recognition sequence on the non-template strand. Similar results were obtained with PNA-T10-LysNH$_2$ and the plasmids pA10-KS and pT10-KS. Using *E. coli* RNA polymerase and the pT10UV5 plasmid ($A_{10}$-sequence on the template strand) transcription elongation arrest was obtained with PNA-$T_{10}$-LysNH$_2$.

EXAMPLE 79

Biological Stability of PNA

A mixture of PNA-$T_5$ (10 μg) and a control, "normal" peptide (10 μg) in 40 μl 50 mM Tris-HCl, pH 7.4 was treated with varying amounts of peptidase from porcine intestinal mucosa or protease from *Streptomyces caespitosus* for 10 min at 37° C. The amount of PNA and peptide was determined by HPLC analysis (reversed phase C-18 column: 0–60% acetonitrile, 0.1% trifluoroacetic acid).

At peptidase/protease concentrations where complete degradation of the peptide was observed (no HPLC peak) the PNA was still intact.

EXAMPLE 80

Inhibition of Gene Expression

A preferred assay to test the ability of peptide nucleic acids to inhibit expression of the E2 mRNA of papillomavirus is based on the well-documented transactivation properties of E2. Spalholtz, et al., *J. Virol.*, 1987, 61, 2128–2137. A reporter plasmid (E2RECAT) was constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of antisense PNAs to the growth medium at final concentrations of 5, 15 and 30 mM. The next day cells are transfected with 10 μg of E2RE1CAT by calcium phosphate precipitation. Ten micrograms of E2RE1CAT and 10 μg of carrier DNA (PUC 19) are mixed with 62 μl of 2 M CaCl$_2$ in a final volume of 250 μl of H$_2$O, followed by addition of 250 μl of 2× HBSP (1.5 mM Na$_2$PO$_2$. 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 mM Na$_2$PO$_2$, 5 mM KCl, 140 mM NaCl, 6 mM glucose and 25 mM HEPES, pH 7.0. After shocking, cells are washed 2 times with serum free DMEM and refed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 μl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 μl of cell extract, 5 μl of 4 mM acetyl coenzyme A, 18 μl H$_2$O and 1 μl $^{14}$C-chloramphenicol, 40–60 mCi/mM. After incubation, chloramphenicol (acetylated and nonacetylated forms) is extracted with ethyl acetate and evaporated to dryness. Samples are resuspended in 25 μl of ethyl acetate, spotted onto a TLC plate and chromatographed in chloroform:methanol (19:1). Chromatographs are analyzed by autoradiography. Spots corresponding to acetylated and nonacetylated $^{14}$C-chloramphenicol are excised from the TLC plate and counted by liquid scintillation for quantitation of CAT activity. Peptide nucleic acids that depress CAT activity in a dose dependent fashion are considered positives.

B. Inhibition of HPV E2 Expression

The assay for inhibition of human papillomavirus (HPV) E2 by peptide nucleic acids is essentially the same as that for BPV-1 E2. For HPV assays appropriate HPVs are cotransfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for antisense studies. For each PNA, cells are pretreated as above, transfected with E2RE1CAT, and analyzed for CAT activity as above. Peptide nucleic acids are considered to have a positive effect if they can depress CAT activity in a dose dependent fashion.

EXAMPLE 81

Synthesis of PNA 15-mer Containing Four Naturally Occurring Nucleobases; H-[Taeg]-[Aaeg]-[Gaeg]-[Taeg]-[Taeg]-[Aaeg]-[Taeg]-[Caeg]-[Taeg]-[Caeg]-[Taeg]-[Aaeg]-[Taeg]-[Caeg]-[Taeg]-LYS-NH2

The protected PNA was assembled onto a Boc-Lys(ClZ) modified MBHA resin with a substitution of approximately 0.145 mmol/g. Capping of uncoupled amino groups was only carried out before the incorporation of the BocGaeg-OH monomer.

Synthesis was initiated on 100 mg (dry weight) of neutralised Boc-Lys (ClA)-MBHA resin that had been preswollen overnight in DCM. The incorporation of the monomers followed the protocol of Example 42, except at step 5 for the incorporation of the BocAaeg-OH monomer. Step 5 for the present synthesis involved addition of 4 equiv. diisopropyl carbodiimide (0.06 ml; 9.7 μl) and 4 equiv. BocAaeg-OH (0.06 mmol; 32 mg) dissolved in 0.6 ml DCM/DMF (1:1, v/v) (final concentration of monomer 0.1M). The coupling reaction was allowed to proceed for 1×15 min and 1×60 min. (recoupling).

All qualitative Kaiser tests were negative (straw-yellow color with no coloration of the beads). The PNA-oligomer was cleaved and purified by the standard procedure. FAB-MS average mass found(calc.) (M+H) 4145.1 (4146.1).

EXAMPLE 82

Hybridization of H-TAGTTATCTCTATCT-LysNH$_2$

| DNA -target | pH | Tm |
|---|---|---|
| 5'----3' | 5 | 60.5 |
| 5'----3' | 7.2 | 43.0 |
| 5'----3' | 9 | 38.5 |
| 5'----3' | 5 | 64.5/49.0 |
| 5'----3' | 7.2 | 53.5 |
| 5'----3' | 9 | 51.5 |

The fact that there is almost no loss in Tm in going from pH 7.2 to 9.0 indicates that Hoogsteen basepairing is not involved. The increase in Tm in going from 7.2 to 5 is large for the parallel orientation and is probably due to the formation of a 2:1 complex. It is believed that the most favorable orientation in the Watson-Crick binding motif is the 3'/N-orientation and that in the Hoogsteen motif the 5'/N-orientation is the most stable. Thus, it may be the case that the most stable complex is with the two PNA's strands anti parallel.

There is apparently a very strong preference for a parallel orientation of the Hoogsteen strand. This seems to explain why even at pH 9 a 2:1 complex is seen with the 5'/N-orientation. Furthermore, it explains the small loss in going from pH 7.2 to 9 in the 3'/N, as this is probably a 1:1 complex.

EXAMPLE 83

Solid-Phase Synthesis of H-[Taeg]$_2$-Aaeg-Taeg-Caeg-Aaeg-Taeg-Caeg-Taeg-Caeg-Lys-NH2

(a) Stepwise Assembly of Boc-[Taeg]2-A(Z)aeg-Taeg-C(Z)aeg-A(Z)aeg-Taeg-C(Z)aeg-Taeg-C(Z)aeg-Lys(ClZ)-MBHA Resin About 1 g of wet Boc-Lys(ClZ)-MBHA (0.28 mmol Lys/g) resin was placed in a 5 ml SPPS reaction vessel. Boc-[Taeg]2-A(Z)aeg-Taeg-C(Z)aeg-A(Z)aeg-Taeg-C(Z)aeg-Taeg-C(Z)aeg-Lys(ClZ)-MBHA resin was assembled by in situ DCC coupling of the five first residues utilizing 0.16 M of BocC[Z]-OH, BocTaeg-OH or BocA(Z)aeg-OH, together with 0.16 M DCC in 2.0 ml 50% DMF/CH2Cl2 ("Synthetic Protocol 9") and by analogous in situ DIC coupling of the five last residues ("Synthetic Protocol 10"). Each coupling reaction was allowed to proceed for a total of 20–24 hrs with shaking. The synthesis was monitored by the ninhydrin reaction, which showed nearly quantitative incorporation of all residues except of the first A(Z)aeg residue, which had to be coupled twice. The total coupling yield was about 96% (first coupling, about 89% efficiency).

(b) Cleavage, Purification, and Identification of H-[Taeg]2-Aaeg-Taeg-Caeg-Aaeg-Taeg-Caeg-Taeg-Caeg-Lys-NH2

The protected Boc-[Taeg]2-A(Z)aeg-Taeg-C(Z)aeg-A(Z)aeg-Taeg-C(Z)aeg-Taeg-C(Z)aeg-Lys(ClZ)-MBHA resin was treated as described in Example 27c to yield about 53.4 mg of crude material upon HF cleavage of 166.1 mg dry Boc-[Taeg]2-A(Z)aeg-Taeg-C(Z)aeg-A(Z)aeg-Taeg-C(Z)aeg-Taeg-C(Z)aeg-Lys(ClZ)-MBHA resin. The crude product (53.4 mg) was purified to give 18.3 mg of H-[Taeg]2-Aaeg-Taeg-Caeg-Aaeg-Taeg-Caeg-Taeg-Caeg-Lys-NH2. For (M+H)+, the calculated m/z value=2780.17 and the measured m/z value=2780.07.

EXAMPLE 84

Hybridization Properties of H-TTA TCA TCT C-Lys-NH$_2$

The title compound hybridized with the following oligonucleotides:

| Oligodeoxynucleotide | pH | Tm (° C.) |
|---|---|---|
| 5'-AAT AGT AGT G-3 | 5 | 31.5† |
| 5'-ATT AGT AGT G-3' | 7.2 | 28.5† |
| 5'-AAT AGT AGT G-3" | 9 | 28.0† |
| 5'-GTG ATG ATA A-3' | 7.2 | 30.5 |
| 5'-GTG ATG ATA A-3' | 9 | 28.0 |

†Low hypochromicity

EXAMPLE 85

Synthesis of a PNA With Two Parallel Strings Tied Together

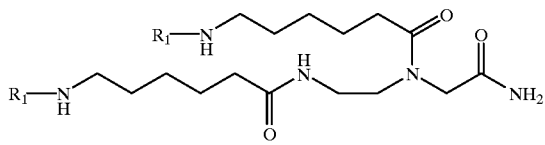

A 375 mg portion of MBHA resin (loading 0.6 mmol/g) was allowed to swell over night in dichloromethane (DCM). After an hour in DMF/DCM, the resin was neutralized by washing 2 times with 5% diisopropylethylamine in DCM (2 min.), followed by washing with DCM (2 ml; 6×1 min.) N,N'-di-Boc-aminoethyl glycine (41.9 mg; 0.132 mmol) disolved in 2 ml DMF was added to the resin, followed by DCC (64.9 mg; 0.315 mmol) dissolved in 1 ml of DCM. After 2.5 hours, the resin was washed with DMF 3 times (1 min.) and once with DCM (1 min.). The unreacted amino groups were then capped by treatment with acetic anhydride/DCM/pyridine (1 ml\2 ml\2 ml) for 72 hours. After washing with DCM (2 ml; 4×1 min), a Kaiser test showed no amino groups were present. The resin was deprotected and washed as described above. This was followed by reaction with 6-(Bocamino)-hexanoic acid DHBT ester (255.8 mg; 67 mmol) dissolved in DMF/DCM 1:1 (4 ml) overnight. After washing and neutraliation, a Kaiser test and an isatin test were performed. Both were negative. After capping, the elongenation of the PNA-chains was performed according to standard procedures for DCC couplings. All Kaiser tests performed after the coupling reactions were negative (Yellow). Qualitative Kaiser tests were done after deprotection of PNA units number 1, 2, 4, and 6. Each test was blue. The PNA oligomers were cleaved and purified by standard procedures.

The amount of monomer and DCC used for each coupling was as follows (total volume 4.5 ml):

| Coupling | Monomer (T) | DCC |
|---|---|---|
| 1. | 173 mg | 95 mg |
| 2. | 176 mg | 101 mg |
| 3. | 174 mg | 97 mg |
| 4. | 174 mg | 103 mg |
| 5. | 178 mg | 97 mg |
| 6. | 173 mg | 99 mg |
| 7. | 174 mg | 95 mg |
| 8. | 175 mg | 96 mg |

For the PNA having the Structure (70) where $R_{70}=T_6$, there was 24.5 mg of crude product, which resulted in 6.9 mg. after purification. For the PNA where $R_1=T_8$, there was 28.8 mg of crude product, which resulted in 2.8 mg. after purification. The products had a high tendency of aggregation, as indicated by a complex HPLC chromatogram after a few hours at room temperature in concentration above 1 mg/ml. The PNA-$(T_6)_2$ and PNA-$(T_8)_2$ were hybridised to $(dA)_6$ and $(dA)_8$, respectively, with recorded Tm of 42° C. and 59° C., respectively.

EXAMPLE 86

Solid-Phase Synthesis of H-[Taeg]$_5$-Lys(ClZ)-MBHA Resin

The PNA oligomer was assembled onto 500 mg (dry weight) of MBHA resin that had been preswollen overnight in DCM. The resin was initially substituted with approximately 0.15 mmol/g Boc-Lys (ClZ) as determined by quantitative ninhydrin reaction. The stepwise synthesis of the oligomer followed the synthetic protocol described in Example 42 employing 0.077 g (0.2 mmol) BocTaeg-OH and 31.3 µl (0.2 mmol) diisopropyl carbodiimide in 2.0 ml 50% DMF/CH$_2$Cl$_2$ in each coupling. Capping of uncoupled amino groups was carried out before deprotection in each step. All qualitative Kaiser tests were negative indicating near 100% coupling yield.

EXAMPLE 87

Solid-Phase Synthesis of H-[Taeg]$_4$-[apgT]-[Taeg]$_5$-Lys-NH$_2$

Synthesis was initiated on approximately ¼ of the wet H-[Taeg]$_5$-Lys(ClZ)-MBHA resin from Example 86. In situ diisopropyl carbodiimide (DIC) couplings of both Boc-(apgT)-OH and BocTaeg-OH were carried out in 1.2 ml 50% DMF/CH$_2$Cl$_2$ using 119 0.048 g (0.12 mmol) and 0.046 g (0.12 mmol) monomer, respectively, and 18.7 µl (0.12 mmol) diisopropyl carbodiimide in each coupling. All qualitative Kaiser tests were negative, indicating near 100% coupling yield. The PNA oligomer was cleaved and purified by standard procedures. For (M+H)+, the calculated m/z value was 2820.15 and the measured m/z value was 2820.92.

EXAMPLE 88

Solid-Phase Synthesis of H-[Taeg]$_4$-[proT]-[Taeg]$_5$-Lys-NH$_2$

Synthesis was initiated on approximately ¼ of the wet H-[Taeg]$_5$-Lys(ClZ)-MBHA resin from Example 86. In situ diisopropyl carbodiimide couplings of BocTaeg-OH were carried out in 1.2 ml 50% DMF/CH$_2$Cl$_2$ using 0.046 g (0.12 mmol) monomer and 18.7 µl (0.12 mmol) diisopropyl carbodiimide in each coupling. Due to solubility problems, Boc-(proT)-OH 0.048 g (0.12 mmol) was suspended in 2.5 ml 50% DMF/DMSO prior to coupling, the suspension filtered, and approximately 2 ml of the filtrate used in the overnight coupling. All qualitative Kaiser tests were negative, indicating near 100% coupling yield. The PNA oligomer was cleaved and purified by standard procedures.

EXAMPLE 89

Hybridization Properties of H-[Taeg]$_4$-[proT]-[Taeg]5_Lys-NH$_2$

| Oligodeoxynucleotide | Tm (° C.) |
|---|---|
| 5'-AAA AAA AAA A | 53.5 |
| 5-'AAA AGA AAA A | 44.0 |
| 5'-AAA AAG AAA A | 43.5 |
| 5'-AAA ACA AAA A | 46.5 |
| 5'-AAA AAC AAA A | 46.5 |
| 5'-AAA ATA AAA A | 46.5 |
| 5'-AAA AAT AAA A | 46.0 |

EXAMPLE 90

Solid-Phase Synthesis of H-[Taeg]$_4$-[bC]-[Taeg]$_5$-Lys-NH$_2$

The PNA oligomer was assembled onto 100 mg (dry weight) MBHA resin that had been preswollen overnight in DCM. The resin was initially substituted with approximately 0.25 mmol/g Boc-Lys (ClZ) as determined by quantitative ninhydrin reaction. The stepwise synthesis of the oligomer followed synthetic Protocol 9 employing 0.023 g (0.06 mmol) BocTaeg-OH, 0.062 g (0.12 mmol) BocbC(Z)-OH and 0.012 g (0.06 mmol) DCC in 1.2 ml 50% DMF/CH$_2$Cl$_2$ in each coupling. Capping of uncoupled amino groups was carried out before deprotection in each step. All qualitative Kaiser tests were negative, indicating near 100% coupling yield. The PNA-oligomer was cleaved and purified by standard procedures.

EXAMPLE 91

Hybridization properties of H-T$_4$bCT$_5$-Lys-NH$_2$

| Oligodeoxynucleotide | Tm (° C.) |
|---|---|
| 5'-AAA AAA AAA A | 43.5 |
| 5-'AAA AGA AAA A | 58.0 |
| 5'-AAA AAG AAA A | 60.0 |
| 5'-AAA ACA AAA A | 34.5 |
| 5'-AAA AAC AAA A | 34.5 |
| 5'-AAA ATA AAA A | 34.0 |
| 5'-AAA AAT AAA A | 36.0 |

EXAMPLE 92

Stepwise Assembly of H-[Taeg]-[Taeg]-[Taeg]-[Taeg]-[Aaeg]-[Taeg]-[Taeg]-[Taeg]-[Taeg]-[Taeg]-LYS-NH$_2$ Synthesis was initiated on a Boc-[Taeg]$_5$-Lys(ClZ)-MBHA resin (from example 76) that had been preswollen overnight in DCM. The resin resembled approximately 100 mg (dry Weight) of Boc-Lys(ClZ)-MBHA resin (loading 0.15 mmol/g). The incorporation of the monomers followed the protocol of example 55, except for step 5 (incorporation of the BocA(Z)aeg-OH monomer). New step 5 (incorporation of A(Z)aeg) involved addition of 4 equiv. diisopropyl carbodiimide (0.06 mmol; 9.7 µl) and 4 equiv. BocA(Z)aeg-OH (0.06 mmol; 32 mg) dissolved in 0.6 ml DCM/DMF (1:1, v/v) (final concentration of monomer 0.1 M). The coupling reaction was allowed to proceed for 1×15 min. and 1×60 min. (recoupling).

Capping of uncoupled amino groups was only carried out before the incorporation of the BocA(Z)aeg-OH monomer. The coupling reaction was monitored by qualitative ninhydrin reaction (Kaiser test). All qualitative Kaiser tests were negative (straw-yellow color with no coloration of the beads). The PNA oligomer was cleaved and purified by standard procedures.

EXAMPLE 94

Hybridization properties of H-$T_4AT_5$-LysNH$_2$

| Oligodeoxynucleotide | Tm (° C.) |
| --- | --- |
| 5'-AAA AAA AAA A | 59.5 |
| 5-'AAA AGA AAA A | 45.0 |
| 5'-AAA AAG AAA A | 45.5 |
| 5'-AAA ACA AAA A | 48.0 |
| 5'-AAA AAC AAA A | 48.0 |
| 5'-AAA ATA AAA A | 52.0 |
| 5'-AAA AAT AAA A | 52.5 |

EXAMPLE 95

Stepwise Assembly of H-[Taeg]-[Taeg]-[Taeg]-[Taeg]-[Gaeg]-[Gaeg]-[Taeg]-[Gaeg]-[Taeg]-[Gaeg]-LYS-NH$_2$ The protected PNA was assembled onto a Boc-Lys(ClZ) modified MBHA resin with a substitution of 0 15 mmol/g. The incorporation of the monomers followed the protocol of example 32, except that the capping step 11 and the washing step 12 were omitted. After the incorporation and deprotection of the first, second, and fourth G(Bzl)aeg-monomer there were some difficulties getting the resin to swell properly. Three hours of shaking in neat DCM gave acceptable swelling. For the incorporation of residues Taeg-4, G(Bzl) aeg-6, and Taeg-7 to Taeg-10, recoupling was necessary to obtain near quantitative coupling yields. Taeg$_4$ (2× in 50% DMF/DCM), Gaeg$_6$ (2× in 50% DMF/DCM), Taeg$_7$ (2× in 50% DMF/DCM, 1× in 50% NMP/DCM and 1× in neat DCM), Taeg$_8$ (1× in 50% DMF/DCM and 2× in neat DCM), Taeg$_9$ (2× in 50% DMF/DCM), Taeg$_{10}$ (2× in 50% DMF/DCM). All qualitative Kaiser tests were negative (straw-yellow color with no coloration of the beads). The PNA oligomer was cleaved and purified by standard procedures

EXAMPLE 96

Hybridization Properties of Crude (Approx. 50%) H-$T_4G_2$TGTG-LysNH$_2$

| Oligodeoxynucleotide | Tm |
| --- | --- |
| 5'-A4C2ACAC | 38 |
| 5'-CACAC2A4 | 55 |

EXAMPLE 97

Large Scale Solid-Phase Synthesis of H-[Taeg]$_6$-Lys-NH$_2$, H-[Taeg]$_7$-Lys-NH$_2$, H-[Taeg]$_8$-Lys-NH$_2$, H-[Taeg]-Lys-NH$_2$, and H-[Taeg]$_{10}$-Lys-NH$_2$ (a) Stepwise Assembly of Boc-[Taeg]$_{10}$-Lys(ClZ)-MBHA Resin and Shorter Fragments About 9 g of wet Boc-[Taeg]$_3$-Lys(ClZ)-MBHA (see, Example 29b) resin was placed in a 60 ml SPPS reaction vessel. Boc-[Taeg]$_5$-Lys(ClZ)-MBHA resin was assembled by single coupling of both residues with 0.15 M of BocTaeg-OPfp in 10 ml neat CH$_2$Cl$_2$ ("Synthetic Protocol 8"). Both coupling reactions were allowed to proceed overnight. The synthesis was monitored by the ninhydrin reaction, which showed close to quantitative incorporation of both residues. After deprotection of the N-terminal Boc group, about 4.5 g of H-[Taeg]$_5$-Lys(ClZ)-MBHA was placed in a 20 ml SPPS reaction vessel and elongated to Boc-[Taeg]$_8$-Lys(ClZ)-MBHA by single in situ DCC coupling of all residues (close to quantitative, except for residue number eight) overnight with 0.2 M of BocTaeg-OH together with 0.2 M DCC in 7.5 ml neat CH$_2$Cl$_2$ ("Synthetic Protocol 9"). Before coupling of Taeg residues number seven and eight, respectively, small portions of H-[Taeg]$_6$-Lys(ClZ)-MBHA and H-[Taeg]$_7$-Lys (ClZ)-MBHA, respectively, were taken out for HF cleavage. Taeg residue number eight was coupled twice (overnight) to give close to quantitative incorporation. After deprotection of the N-terminal Boc group, a large portion of H-[Taeg]$_8$-Lys(ClZ)-MBHA was taken out for HF cleavage. Boc-[Taeg]$_{10}$-Lys(ClZ)-MBHA resin was assembled by double in situ DCC coupling of 0.16 M BocTaeg-OH, together with 0.16 M DCC in 2.0 ml 50% DMF/CH$_2$Cl$_2$ ("Synthetic Protocol" 9). Before coupling of the final residue, a small portion of H-[Taeg]$_9$-Lys(ClZ)-MBHA was taken out for HF cleavage.

(b) Cleavage, Purification, and Identification of H-[Taeg]$_6$-Lys-NH$_2$

The protected Boc-[Taeg]$_6$-Lys(ClZ)-MBHA resin was treated as described in Example 27c to yield about 14.0 mg of crude material upon HF cleavage of 52.4 mg dry H-Taeg]$_6$-Lys(ClZ)-MBHA resin. The crude product was not purified (about 99% purity).

(c) Cleavage, Purification, and Identification of H-[Taeg]$_7$-Lys-NH$_2$

The protected Boc-[Taeg]$_7$-Lys(ClZ)-MBHA resin was treated as described in Example 27c to yield about 5.2 mg of crude material upon HF cleavage of 58.4 mg dry H-Taeg]$_7$-Lys(ClZ)-MBHA resin.

(d) Cleavage, Purification, and Identification of H-[Taeg]$_8$-Lys-NH$_2$

The protected Boc-[Taeg]$_8$-Lys(ClZ)-MBHA resin was treated as described in Example 27c to yield about 114 mg of crude material upon HF cleavage of about 604 mg dry H-Taeg]$_8$-Lys(ClZ)-MBHA resin.

(e) Cleavage, Purification, and Identification of H-[Taeg]$_9$-Lys-NH$_2$

The protected Boc-[Taeg]$_9$-Lys(ClZ)-MBHA resin was treated as described in Example 27c to yield about 19.3 mg of crude material upon HF cleavage of 81.0 mg dry H-Taeg]$_9$-Lys(ClZ)-MBHA resin.

(f) Cleavage, Purification, and Identification of H-[Taeg]$_{10}$-Lys-NH$_2$

The protected Boc-[Taeg]$_{10}$-Lys(ClZ)-MBHA resin was treated as described in Example 27c to yield about 141 mg of crude material upon HF cleavage of about 417 mg dry H-Taeg]$_{10}$-Lys(ClZ)-MBHA resin.

(g) Synthetic Protocol 8 (General Protocol)

(1) Boc-deprotection with TFA/CH$_2$Cl$_2$ (1:1, v/v), 3×1 min and 1×30 min; (2) washing with CH$_2$Cl$_2$, 6×1 min; (3) neutralization with DIEA/CH$_2$Cl$_2$ (1: 19, v/v), 3×2 min; (4) washing with CH$_2$Cl$_2$, 6×1 min, and drain for 1 min; (5) at some stages of the synthesis, 2–5 mg sample of PNA-resin is taken out and dried thoroughly for a ninhydrin analysis to determine the substitution; (6) addition of Boc-protected PNA monomer (Pfp ester); the coupling reaction was allowed to proceed for a total of X hrs shaking; (7) washing with DMF, 1×2 min; (8) washing with CH$_2$Cl$_2$, 4×1 min; (9) neutralization with DIEA/CH$_2$Cl$_2$ (1: 19, v/v), 2×2 min; (10) washing with CH$_2$Cl$_2$, 6×1 min; (11) occasionally, 2–5 mg sample of protected PNA-resin is taken out and dried thoroughly for a ninhydrin analysis to determine the extent of coupling; (12) at some stages of the synthesis, unreacted amino groups are blocked by acetylation with a mixture of acetic anhydride/pyridine/CH$_2$Cl$_2$ (1:1:2, v/v/v) for 2 h followed by washing with CH$_2$Cl$_2$, 6×1 min, and, occasionally, ninhydrin analysis.

EXAMPLE 98

Solid-Phase Synthesis of H-[Taeg]4-Caeg-[Taeg]5-Lys-NH$_2$ (a) Stepwise Assembly of Boc-[Taeg]4-C[Z]aeg-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-C[Z]aeg-[Taeg]5-Lys(ClZ)-MBHA resin was assembled by in situ DCC coupling of all residues utilizing 0.16 M of BocC[Z]aeg-OH together with 0.16 M DCC in 2.0 ml 50% DMF/CH$_2$Cl$_2$ or 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed about 98% incorporation of C[Z]aeg and close to quantitative incorporation of all the Taeg residues.

(b) Cleavage, Purification, and Identification of H-[Taeg]4-C[Z]aeg-[Taeg]5-Lys-NH$_2$ The protected Boc-[Taeg]4-C[Z]aeg-[Taeg]5-Lys(ClZ)-MBHA resin was treated as described in Example 27c to yield about 22.5 mg of crude material upon HF cleavage of 128.2 mg dry H-[Taeg]4-C[Z]aeg-[Taeg]5-Lys(ClZ)-MBHA resin. Crude product (5.8 mg) was purified to give 3.1 mg of H-[Taeg]4-Caeg-[Taeg]5-Lys-NH$_2$.

(c) Synthetic Protocol 9 (General Protocol)

(1) Boc-deprotection with TFA/CH$_2$Cl$_2$ (1:1, v/v), 3×1 min and 1×30 min; (2) washing with CH$_2$Cl$_2$, 6×1 min; (3) neutralization with DIEA/CH$_2$Cl$_2$ (1: 19, v/v), 3×2 min; (4) washing with CH$_2$Cl$_2$, 6×1 min, and drain for 1 min; (5) at some stages of the synthesis, 2–5 mg sample of PNA-resin is taken out and dried thoroughly for a ninhydrin analysis to determine the substitution; (6) addition of Boc-protected PNA monomer (free acid) in X ml DMF followed by addition of DCC in X ml CH$_2$Cl$_2$; the coupling reaction was allowed to proceed for a total of Y hrs shaking; (7) washing with DMF, 1×2 min; (8) washing with CH$_2$Cl$_2$, 4×1 min; (9) neutralization with DIEA/CH$_2$Cl$_2$ (1: 19, v/v), 2×2 min; (10) washing with CH$_2$Cl$_2$, 6×1 min; (11) occasionally, 2–5 mg sample of protected PNA-resin is taken out and dried thoroughly for a ninhydrin analysis to determine the extent of coupling; (12) at some stages of the synthesis, unreacted amino groups are blocked by acetylation with a mixture of acetic anhydride/pyridine/CH$_2$Cl$_2$ (1:1:2, v/v/v) for 2 h followed by washing with CH$_2$Cl$_2$, 6×1 min, and, occasionally, ninhydrin analysis.

EXAMPLE 99

Solid-Phase Synthesis of H-[Taeg]4-(NBaeg)-[Taeg]5-Lys-NH$_2$ (NB=COCH3)

(a) Stepwise Assembly of Boc-[Taeg]4-(NBaeg)-[Taeg]5-Lys(ClZ)-MBHA Resin

About 1 g of wet Boc-[Taeg]5-Lys(ClZ)-MBHA resin was placed in a 5 ml SPPS reaction vessel. Boc-[Taeg]4-(NBaeg)-[Taeg]5-Lys(ClZ)-MBHA resin was assembled by in situ DCC coupling utilizing 0.16 M of Boc(NBaeg)-OH together with 0.16 M DCC in 2.0 ml neat CH$_2$Cl$_2$ or 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The NBaeg residue was coupled three times and the Taeg residues were all coupled once. The synthesis was monitored by the ninhydrin reaction which showed >99% total incorporation of NBaeg (about 88% after the first coupling and about 93% after the second coupling) and close to quantitative incorporation of all the Taeg residues.

(b) Cleavage, Purification, and Identification of H-[Taeg]4-(NBaeg)-[Taeg]5-Lys-NH$_2$ The protected Boc-[Taeg]4-(NBaeg)-[Taeg]5-Lys(ClZ)-MBHA resin was treated as described in Example 27c to yield about 33.6 mg of crude material upon HF cleavage of 108.9 mg dry H-[Taeg]4-(NBaeg)-[Taeg]5-Lys(ClZ)-MBHA resin. Crude product (20.6 mg) was purified to give 4.6 mg of H-[Taeg]4-(NBaeg)-[Taeg]5-Lys-NH$_2$. For (M+H)+, the calculated m/z value was 2683.12 and the measured m/z value was 2683.09.

EXAMPLE 100

Solid-Phase Synthesis of H-[Taeg]4-aeg-[Taeg]5-Lys-NH$_2$ (a) Stepwise Assembly of Boc-[Taeg]4-aeg-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-aeg-[Taeg]5-Lys(ClZ)-MBHA resin was assembled by in situ DCC single coupling of all residues utilizing: (1) 0.16 M of Bocaeg-OH together with 0.16 M DCC in 2.0 ml 50% DMF/CH$_2$Cl$_2$ or (2) 0.16 M BocTaeg-OH together with (2) 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-aeg-[Taeg]5-Lys-NH$_2$ The protected Boc-[Taeg]4-aeg-[Taeg]5-Lys(ClZ)-MBHA resin was treated as described in Example 27c to yield about 22.2 mg of crude material upon HF cleavage of 126.0 mg dry H-[Taeg]4-aeg-[Taeg]5-Lys(ClZ)-MBHA resin. Crude product (22.2 mg) was purified to give 7.6 mg of H-[Taeg]4-aeg-[Taeg]5-Lys-NH$_2$. For (M+H)+, the calculated m/z value was 2641.11 and the measured m/z value was 2641.16.

EXAMPLE 101

Solid-Phase Synthesis of H-[Taeg]4-Gly-[Taeg]5-Lys-NH$_2$ (a) Stepwise Assembly of Boc-[Taeg]4-Gly-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-Gly-[Taeg]5-Lys(ClZ)-MBHA resin was assembled by in situ DCC single coupling of all residues utilizing: (1) 0.16 M of BocGly-OH together with 0.16 M DCC in 2.0 ml 50% DMF/CH$_2$Cl$_2$ or (2) 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly-[Taeg]5-Lys-NH$_2$ The protected Boc-[Taeg]4-Gly-[Taeg]5-Lys(ClZ)-MBHA resin was treated as described in Example 28c to yield about 45.0 mg of crude material upon HF cleavage of 124.1 mg dry H-[Taeg]4-Gly-[Taeg]5-Lys(ClZ)-MBHA resin. Crude product (40.4 mg) was purified to give 8.2 mg of H-[Taeg]4-Gly-[Taeg]5-Lys-NH$_2$.

EXAMPLE 102

Solid-Phase Synthesis of H-[Taeg]4-Gly2-[Taeg]5-Lys-NH$_2$ (a) Stepwise Assembly of Boc-[Taeg]4-Gly2-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-[C[Z]aeg]2-Taeg-C[Z]aeg-Taeg-C[Z]aeg-Lys(ClZ)-MBHA resin was assembled by in situ DCC single coupling of all residues utilizing: (1) 0.16 M of BocGly-OH together with 0.16 M DCC in 2.0 ml 50% DMF/CH$_2$Cl$_2$ or (2) 0.16 M BocTaeg-OH together with 0.16, M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly2-[Taeg]5-Lys-NH$_2$ The protected Boc-[Taeg]4-Gly2-[Taeg]5-Lys(ClZ)-MBHA resin was treated as described in Example 27c to yield about 32.6 mg of crude material upon HF cleavage of 156.6 mg dry H-[Taeg]4-Gly2-[Taeg]5-Lys(ClZ)-MBHA resin. Crude product (30 mg) was purified to give 7.8 mg of H-[Taeg]4-Gly2-[Taeg]5-Lys-NH$_2$. For (M+H)+, the calculated m/z value was 2655.09 and the measured m/z value was 2655.37.

EXAMPLE 103

Solid-Phase Synthesis of H-[Taeg]4-[Caeg]2-Taeg-Caeg-Taeg-Caeg-Lys-NH$_2$ (a) Stepwise Assembly of Boc-[Taeg]4-[C[Z]aeg]2-Taeg-C[Z]aeg-Taeg-C[Z]aeg-Lys(Clz)-MBHA Resin About 1.5 g of wet Boc-Lys(ClZ)-MBHA (0.28 mmol Lys/g) resin was placed in a 5 ml SPPS reaction vessel. Boc-[Taeg]4-[C[Z]aeg]2-Taeg-C[Z]aeg-Taeg-C[Z]aeg-Lys(ClZ)-MBHA resin was assembled by in situ DCC single coupling of all residues utilizing: (1) 0.16 M of BocC[Z]-OH together with 0.16 M DCC in 2.0 ml 50% DMF/CH$_2$Cl$_2$ or (2) 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]$_4$-[Caeg]$_2$-Taeg-Caeg-Taeg-Caeg-Lys-NH$_2$ The protected Boc-[Taeg]4-[C[Z]aeg]2-Taeg-C[Z]aeg-Taeg-C[Z]aeg-Lys(ClZ)-MBHA resin was treated as described in Example 27c to yield about 52.1 mg of crude material upon HF cleavage of 216.7 mg dry H-[Taeg]4-[C[Z]aeg]2-Taeg-C[Z]aeg-Taeg-C[Z]aeg-Lys(CLZ)-MBHA resin. Crude product (30.6 mg) was purified to give 6.2 mg of H-[Taeg]4-[Caeg]2-Taeg-Caeg-Taeg-Caeg-Lys-NH$_2$. For (M+H)+ the calculated m/z value was 2747.15 and the measured m/z value was 2746.78.

EXAMPLE 104

Solid-Phase Synthesis of H-Caeg-Taeg-Caeg-Taeg-[Caeg]3-Taeg-Caeg-Taeg-Lys-NH$_2$ (a) Stepwise Assembly of Boc-C[Z]aeg-Taeg-C[Z]aeg-Taeg-[C[Z]aeg]3-Taeg-C[Z]aeg-Taeg-Lys(ClZ)-MBHA Resin About 1.5 g of wet Boc-Lys(ClZ)-MBHA (0.28 mmol Lys/g) resin was placed in a 5 ml SPPS reaction vessel. Boc-C[Z]aeg-Taeg-C[Z]aeg-Taeg-[C[Z]aeg]3-Taeg-C[Z]aeg-Taeg-Lys(ClZ)-MBHA resin was assembled by in situ DCC single coupling of all residues utilizing: (1) 0.16 M of BocC[Z]-OH together with 0.16 M DCC in 2.0 ml 50% DMF/CH$_2$Cl$_2$ or (2) 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-Caeg-Taeg-Caeg-Taeg-[Caeg]3-Taeg-Caeg-Taeg-Lys-NH 2

The protected Boc-C[Z]aeg-Taeg-C[Z]aeg-Taeg-[C[Z]aeg]3-Taeg-C[Z]aeg-TaegLys(ClZ)-MBHA resin was treated as described in Example 27c to yield about 56.1 mg of crude material upon HF cleavage of 255.0 mg dry H—C[Z]aeg-Taeg-C[Z]aeg-Taeg-[C[Z]aeg]3-Taeg-C[Z]aeg-TaegLys(ClZ)-MBHA resin. Crude product (85.8 mg) was purified to give 46.2 mg of H-Caeg-Taeg-Caeg-Taeg-[Caeg]3-Taeg-Caeg-Taeg-LysNH$_2$. For (M+H)+ the calculated m/z value was 2717.15 and the measured m/z value was 2716.93.

EXAMPLE 105

Solid-Phase Synthesis of H-[Taeg]2-[Caeg]3-[Taeg]2-[Caeg]2-Lys-NH$_2$, H-Caeg-[Taeg]2-[Caeg]3-[Taeg]2-[Caeg]2-Lys-NH$_2$, and H-Tyr-[Taeg]2-[Caeg]3-[Taeg]2-[Caeg]2-Lys-NH$_2$ (a) Stepwise Assembly of Boc-[Taeg]2-[C(Z)aeg]3-[Taeg]2-[C(Z)aeg]2-Lys(ClZ)-MBHA Resin, Boc-Caeg-[Taeg]2-[C(Z)aeg]3-[Taeg]2-[C(Z)aeg]2-Lys(ClZ)-MBHA Resin, and Boc-Tyr(BrZ)-[Taeg]2-[C(Z)aeg]3-[Taeg]2-[C(Z)aeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]-OH together with 0.16 M DCC in 3.0 ml 50% DMF/$CH_2Cl_2$ or (2) 0.16 M BocTaeg-OH together with 0.16 M DCC in 3.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)-OH and a small portion was coupled quantitatively onto one more Caeg residue. Both couplings employed the above-mentioned synthetic protocol.

(b) Cleavage, Purification, and Identification of H-[Taeg]2-[Caeg]3-[Taeg]2-[Caeg]2-Lys-$NH_2$ The protected Boc-[Taeg]2-[C(Z)aeg]3-[Taeg]2-[C(Z)aeg]2-Lys(ClZ)-MBHA resin was treated as described in Example 27c to yield about 50.9 mg of crude material upon HF cleavage of 182.5 mg dry H-[Taeg]2-[C(Z)aeg]3-[Taeg]2-[C(Z)aeg]2-Lys(ClZ)-MBHA resin. Crude product (50.9) mg was purified to give 13.7 mg of H-[Taeg]2-[Caeg]3-[Taeg]2-[Caeg]2-Lys$NH_2$. For (M+H)+ the calculated m/z value was 2466.04; the m/z value was not measured.

(c) Cleavage, Purification, and Identification of H-Tyr-[Taeg]2-[Caeg]3-[Taeg]2-[Caeg]2-Lys-$NH_2$ The protected Boc-Tyr(BrZ)-[Taeg]2-[C(Z)aeg]3-[Taeg]2-[C(Z)aeg]2-Lys(ClZ)-MBHA resin was treated as described in Example 27c to yield about 60.8 mg of crude material upon HF cleavage of 188.8 mg dry H-Tyr(BrZ)-[Taeg]2-[C(Z)aeg]3-[Taeg]2-[C(Z)aeg]2-Lys(ClZ)-MBHA resin. Crude product (60.8 mg) was purified to give 20.7 mg of H-Tyr-[Taeg]2-[Caeg]3-[Taeg]2-[Caeg]2-Lys$NH_2$. For (M+H)+ the calculated m/z value was 2629.11 and the measured m/z value was 2629.11.

(d) Cleavage, Purification, and Identification of H-Caeg-[Taeg]2-[Caeg]3-[Taeg]2-[Caeg]2-Lys-$NH_2$ The protected Boc-C(Z)aeg-[Taeg]2-[C(Z)aeg]3-[Taeg]2-[C(Z)aeg]2-Lys(ClZ)-MBHA resin was treated as described in Example 27c to yield about 11.7 mg of crude material upon HF cleavage of 42.0 mg dry H—C(Z)aeg-[Taeg]2-[C(Z)aeg]3-[Taeg]2-[C(Z)aeg]2-Lys(ClZ)-MBHA resin. Crude product (11.6 mg) was purified to give 3.1 mg of H-Caeg-[Taeg]2-[Caeg]3-[Taeg]2-[Caeg]2-Lys$NH_2$. For (M+H)+ the calculated m/z value was 2717.15; the m/z value was not measured.

EXAMPLE 106

Solid-Phase Synthesis of H-[Caeg]2-[Taeg]2-[Caeg]3-[Taeg]2-Lys-$NH_2$, H-Taeg-[Caeg]2-[Taeg]2-[Caeg]3-[Taeg]2-Lys-$NH_2$, and H-Tyr-[Caeg]2-[Taeg]2-[Caeg]3-[Taeg]2-Lys-$NH_2$ (a) Stepwise Assembly of Boc-[C(Z)aeg]2-[Taeg]2-[C(Z)aeg]3-[Taeg]2-Lys(ClZ)-MBHA Resin, Boc-Taeg-[C(Z)aeg]2-[Taeg]2-[C(Z)aeg]3-[Taeg]2-Lys(ClZ)-MBHA Resin, and Boc-Tyr(BrZ)-[C(Z)aeg]2-[Taeg]2-[C(Z)aeg]3-[Taeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]-OH together with 0.16 M DCC in 3.0 ml 50% DMF/$CH_2Cl_2$ or (2) 0.16 M BocTaeg-OH together with 0.16 M DCC in 3.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)-OH and a small portion was coupled quantitatively onto one more Taeg residue. Both couplings employed the above-mentioned synthetic protocol.

(b) Cleavage, Purification, and Identification of H-[C(Z)aeg]2-[Taeg]2-[C(Z)aeg]3-[Taeg]2-Lys-$NH_2$ The protected Boc-[C(Z)aeg]2-[Taeg]2-[C(Z)aeg]3-[Taeg]2-Lys(ClZ)-MBHA resin was treated as described in Example 27c to yield about 57.6 mg of crude material upon HF cleavage of 172.7 mg dry H-[C(Z)aeg]2-[Taeg]2-[C(Z)aeg]3-[Taeg]2-Lys(ClZ)-MBHA resin. Crude product (57.6 mg) was purified to give 26.3 mg of H-[Caeg]2-[Taeg]2-[Caeg]3-[Taeg]2-Lys-$NH_2$. For (M+H)+ the calculated m/z value was 2466.04; the m/z value was not measured.

(c) Cleavage, Purification, and Identification of H-Tyr-[C(Z)aeg]2-[Taeg]2-[C(Z)aeg]3-[Taeg]2-Lys-$NH_2$ The protected Boc-Tyr(BrZ)-[C(Z)aeg]2-[Taeg]2-[C(Z)aeg]3-[Taeg]2-Lys(ClZ)-MBHA resin was treated as described in Example 27c to yield about 57.6 mg of crude material upon HF cleavage of 172.7 mg dry H-Tyr(BrZ)-[C(Z)aeg]2-[Taeg]2-[C(Z)aeg]3-[Taeg]2-Lys(ClZ)-MBHA resin. Crude product (47.1 mg) was purified to give 13.4 mg of H-Tyr-[Caeg]2-[Taeg]2-[Caeg]3-[Taeg]2-Lys-$NH_2$. For (M+H)+ the calculated m/z value was 2629.11 and the measured m/z value was 2629.11.

(d) Cleavage, Purification, and Identification of H-Taeg-[C(Z)aeg]2-[Taeg]2-[C(Z)aeg]3-[Taeg]2-Lys-$NH_2$ The protected Boc-Taeg-[C(Z)aeg]2-[Taeg]2-[C(Z)aeg]3-[Taeg]2-Lys(ClZ)-MBHA resin was treated as described in Example 27c to yield about 53.4 mg of crude material upon HF cleavage of 42.4 mg dry H-Taeg-[C(Z)aeg]2-[Taeg]2-[C(Z)aeg]3-[Taeg]2-Lys(ClZ)-MBHA resin. Crude product (11.9 mg) was purified to give 4.3 mg of H-Taeg-[Caeg]2-[Taeg]2-[Caeg]3-[Taeg]2-Lys-$NH_2$. For (M+H)+ the calculated m/z value was 2732.15; the m/z value was not measured.

(c) Synthetic Protocol 10 (General Protocol)

Same protocol as "Synthetic Protocol 9", except that DCC has been replaced with DIC.

EXAMPLE 107

Synthesis of the Backbone Moiety for Scale up by Reductive Amination (a) Preparation of (bocamino)acetaldehyde 3-Amino-1,2-propanediol(80.0 g; 0.88 mol) was dissolved in water (1500 ml) and the solution was cooled to 4° C., whereafter Boc anhydride (230 g; 1.05 mol) was added at once. The solution was gently heated to room temperature with a water bath. The pH was kept at 10.5 by the dropwise addition of sodium hydroxide. Over the course of the reaction a total of 70.2 g NaOH, dissolved in 480 ml water, was added. After stirring overnight, ethyl acetate (1000 ml) was added and the mixture was cooled to 0° C. and the pH was adjusted to 2.5 by the addition of 4 M hydrochloric acid. The ethyl acetate layer was removed and the acidic aqueous solution was extracted with more ethyl acetate (8×500 ml). The combined ethyl acetate solution was reduced to a volume of 1500 ml using a rotary evaporator. The resulting solution was washed with half saturated potassium hydrogen sulphate (1500 ml) and then with saturated sodium chloride. It then was dried over magnesium sulphate and evaporated to dryness, in vacuo. Yield. 145.3 g (86%)

3-Bocamino-1,2-propanediol (144.7 g; 0.757 mol) was suspended in water (750 ml) and potassium periodate (191.5 g; 0.833 mol) was added. The mixture was stirred under nitrogen for 2.5 h and the precipitated potassium iodate was removed by filtration and washed once with water (100 ml). The aqueous phase was extracted with chloroform (6×400 ml). The chloroform extracts were dried and evaporated to dryness, in vacuo. Yield 102 g (93%) of an oil. The (bocamino)acetaldehyde was purified by kugelrohr distillation at 84° C. and 0.3 mmHg in two portions. The yield 79 g (77%) of a colorless oil.

(b) Preparation of (N'-bocaminoethyl)glycine Methyl Ester

Palladium on carbon (10%; 2.00 g) was added to a solution of (bocamino)acetaldehyde (10.0 g; 68.9 mmol) in methanol (150 ml) at 0° C. Sodium acetate (11.3 g; 138 mmol) in methanol (150 ml), and glycine methyl ester hydrochloride (8.65 g; 68.9 mmol) in methanol (75 ml) then were added. The mixture was hydrogenated at atmospheric pressure for 2.5 h, then filtered through celite and evaporated to dryness, in vacuo. The material was redissolved in water (150 ml) and the pH was adjusted to 8.0 with 0.5 N NaOH. The aqueous solution was extracted with methylene chloride (5×150 ml). The combined extracts were dried over sodium sulphate and evaporated to dryness, in vacuo. This resulted in 14.1 g (88%) of (N'-bocaminoethyl)glycine methyl ester. The crude material was purified by kugelrohr destination at 120° C. and 0.5 mmHg to give 11.3 g (70%) of a colorless oil. The product had a purity that was higher than the material produced in example 26 according to tlc-analysis (10% methanol in methylene chloride).

Alternatively, sodium cyanoborohydride can be used as reducing agent instead of hydrogen (with Pd(C) as catalyst), although the yield (42%) was lower.

(c) Preparation of (N'-bocaminoethyl)glycine Ethyl Ester

The title compound was prepared by the above procedure with glycine ethyl ester hydrochloride substituted for glycine methyl ester hydrochloride. Also, the solvent used was ethanol. The yield was 78%.

EXAMPLE 108

Solid-Phase Synthesis of H-Tyr-[Taeg]$_{10}$-Lys-NH$_2$ (a) Stepwise Assembly of Boc-Tyr(BrZ)-[Taeg]$_{10}$-Lys(ClZ)-MBHA Resin About 0.2 g of wet Boc-[Taeg]$_{10}$-Lys(ClZ)-MBHA resin was placed in a 5 ml SPPS reaction vessel. Boc-Tyr(BrZ)-[Taeg]$_{10}$-Lys(ClZ)-MBHA resin was assembled by standard in situ DCC coupling utilizing 0.32 M of BocCTyr(BrZ)-OH together with 0.32 M DCC in 3.0 ml neat CH$_2$Cl$_2$ overnight. The ninhydrin reaction showed about 97% incorporation of BocTyr(BrZ).

(b) Cleavage, Purification, and Identification of H-Tyr-[Taeg]$_{10}$-Lys-NH$_2$ The protected Boc-Tyr(BrZ)-[Taeg]$_{10}$-Lys(ClZ)-MBHA resin was treated as described in Example 27c to yield about 5.5 mg of crude material upon HF cleavage of 20.7 mg dry H-Tyr(BrZ)-[Taeg]$_{10}$-Lys(ClZ)-MBHA resin. The crude product was purified to give 2.5 mg of H-Tyr-[Taeg]$_{10}$-Lys-NH$_2$.

EXAMPLE 109

Solid-Phase Synthesis of Dansyl-[Taeg]$_{10}$-Lys-NH$_2$ (a) Stepwise Assembly of Dansyl-[Taeg]$_{10}$-Lys(ClZ)-MBHA Resin About 0.3 g of wet Boc-[Taeg]$_{10}$-Lys(ClZ)-MBHA resin was placed in a 5 ml SPPS reaction vessel. Dansyl-[Taeg]$_{10}$-Lys(ClZ)-MBHA resin was assembled by coupling of 0.5 M dansyl-Cl in 2.0 ml neat pyridine overnight. The ninhydrin reaction showed about 95% incorporation of dansyl.

(b) Cleavage, Purification, and Identification of Dansyl-[Taeg]$_{10}$-Lys-NH$_2$ The protected dansyl-[Taeg]$_{10}$-Lys(ClZ)-MBHA resin was treated as described in Example 27c to yield about 12 mg of crude material upon HF cleavage of 71.3 mg dry dansyl-[Taeg]$_{10}$-Lys(ClZ)-MBHA resin. The crude product was purified to give 5.4 mg of dansyl-[Taeg]$_{10}$-Lys-NH$_2$.

EXAMPLE 110

Solid-Phase Synthesis of Gly-Gly-His-[Taeg]$_{10}$-Lys-NH$_2$ (a) Stepwise Assembly of Boc-Gly-Gly-His(Tos)-[Taeg]$_{10}$-Lys(ClZ)-MBHA Resin About 0.05 g of Boc-[Taeg]$_{10}$-Lys(ClZ)-MBHA resin was placed in a 5 ml SPPS reaction vessel. Boc-Gly-Gly-His(Tos)-[Taeg]$_{10}$-Lys(ClZ)-MBHA resin was assembled by standard double in situ DCC coupling of Boc-protected amino acid (0.1 M) in 2.5 ml 25% DMF/CH$_2$Cl$_2$, except for the first coupling of BocHis (Tos), which was done by using a preformed symmetrical anhydride (0.1M) in 25% DMF/CH$_2$Cl$_2$. All couplings were performed overnight and ninhydrin reactions were not carried out.

(b) Cleavage, Purification, and Identification of Gly-Gly-His-[Taeg]$_{10}$-Lys-NH$_2$ The protected Boc-Gly-Gly-His(Tos)-[Taeg]$_{10}$-Lys(ClZ)-MBHA resin was treated as described in Example 27c to yield about 10.3 mg of crude material (about 40% purity) upon HF cleavage of 34.5 mg dry Boc-Gly-Gly-His(Tos)-[Taeg]$_{10}$-Lys(ClZ)-MBHA resin. A small portion of the crude product (taken out before lyophilization) was purified to give 0.1 mg of Gly-Gly-His-[Taeg]$_{10}$-Lys-NH$_2$.

EXAMPLE 111

Solid-Phase Synthesis of H-[Taeg]$_5$-[Caeg]$_2$-NH$_2$ (a) Stepwise Assembly of Boc-[Taeg]$_5$-[C(Z)aeg]$_2$-MBHA Resin About 0.2 g of MBHA resin was placed in a 3 ml SPPS reaction vessel and neutralized. The loading was determined to be about 0.64 mmol/g. BocC(Z)aeg-OPfp was coupled onto the resin using a concentration of 0.13 M in 2.5 ml 25% phenol//CH$_2$Cl$_2$. The ninhydrin analysis showed a coupling yield of about 40%. The remaining free amino groups were acetylated as usual. Boc-[Taeg]$_5$-[C(Z)aeg]$_2$-MBHA resin was assembled by single in situ DCC coupling of the next residue utilizing 0.11 M of BocC(Z)aeg-OH together with 0.11 M DCC in 2.5 ml 50% DMF/CH$_2$Cl$_2$ and by coupling with 0.13 M BocTaeg-OPfp in neat CH$_2$Cl$_2$ for the remaining residues ("Synthetic Protocol 8"). Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_5$-[Caeg]$_2$-NH$_2$ The protected Boc-[Taeg]$_5$-[C(Z)aeg]$_2$-MBHA resin was treated as described in Example 27c to yield about 21.7 mg of crude material (>80% purity) upon HF cleavage of 94.8 mg dry H-[Taeg]$_5$-[C(Z)aeg]$_2$-MBHA resin. Crude product (7.4 mg) was purified to give 2.0 mg of H-[Taeg]$_5$-[Caeg]$_2$-NH$_2$ (>99% purity).

EXAMPLE 112

Solid-Phase Synthesis of H-[Taeg]$_3$-Caeg-[Taeg]$_4$-NH$_2$ (a) Stepwise Assembly of Boc-[Taeg]$_3$-C (Z) aeg-[Taeg]$_4$-MBHA Resin About 0.2 g of the above-mentioned MBHA resin was placed in a 5 ml SPPS reaction vessel and neutralized. Boc-[Taeg]$_3$-C(Z)aeg-[Taeg]$_4$-MBHA resin was assembled by single in situ DCC coupling of the C(Z)aeg residue utilizing 0.13 M of BocC[Z]aeg-OH together with 0.13 M DCC in 2.5 ml 50% DMF/CH$_2$Cl$_2$ and by coupling the Taeg residues with 0.13 M BocTaeg-OPfp in 2.5 ml neat CH$_2$Cl$_2$. Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_3$-Caeg-[Taeg]$_4$-NH$_2$ The protected Boc-[Taeg]$_3$-C(Z)aeg-[Taeg]$_4$-MBHA resin was treated as described in Example 27c to yield about 44.4 mg of crude material upon HF cleavage of about 123 mg dry H-[Taeg]$_3$-C(z)aeg-[Taeg]$_4$-MBHA resin. Crude product (11.0 mg) was purified to give 3.6 mg of H-[Taeg]$_3$-Caeg-[Taeg]$_4$-NH$_2$.

EXAMPLE 113

Solid-Phase Synthesis of H-Taeg-Caeg-[Taeg]$_8$-LysNH$_2$ (a) Stepwise Assembly of Boc-Taeg-C(Z)aeg-[Taeg]$_8$-Lys(ClZ)-MBHA Resin About 0.3 g of wet Boc-[Taeg]$_8$-Lys(ClZ)-MBHA resin was placed in a 3 ml SPPS reaction vessel. Boc-Taeg-C(Z)aeg-[Taeg]$_8$-Lys(ClZ)-MBHA resin was assembled by single in situ DCC coupling overnight of the C(Z)aeg residue ("Synthetic Protocol" 9) utilizing 0.2 M of BocC[Z]aeg-OH together with 0.2 M DCC in 2.5 ml 50% DMF/CH$_2$Cl$_2$ (incorporation was about 80% as judged by ninhydrin analysis; remaining free amino groups were acetylated) and by overnight coupling the Taeg residue with 0.15 M BocTaeg-OPfp in 2.5 ml neat CH$_2$Cl$_2$ (nearly quantitatively).

(b) Cleavage, Purification, and Identification of H-Taeg-Caeg-[Taeg]$_8$-LysNH$_2$ The protected Boc-Taeg-C(Z)aeg-[Taeg]$_8$-Lys(ClZ)-MBHA resin was treated as described in Example 27c to yield about 22.3 mg of crude material upon HF cleavage of about 76.5 mg dry H-Taeg-C(Z)aeg-[Taeg]$_8$-Lys(ClZ)-MBHA resin. Crude product (6.7 mg) was purified to give 2.6 mg of H-Taeg-Caeg-[Taeg]$_8$-LysNH$_2$. For (M+H)$^+$ the calculated m/z value was 2792.15 and the measured m/z value was 2792.21.

EXAMPLE 114

Solid-Phase Synthesis of H-Caeg-[Taeg]$_5$-Lys-NH$_2$ and H-[Taeg]$_2$-Caeg-[Taeg]$_5$-Lys-NH$_2$ (a) Stepwise Assembly of Boc-[Taeg]$_2$-C(Z)aeg-[Taeg]$_5$-Lys(ClZ)-MBHA Resin About 0.5 g of wet Boc-[Taeg]$_5$-Lys(ClZ)-MBHA resin was placed in a 5 ml SPPS reaction vessel. Boc-[Taeg]$_2$-C(Z)aeg-[Taeg]$_5$-Lys(ClZ)-MBHA resin was assembled by single in situ DCC coupling of all residues utilizing: (1) 0.12 M of BocC[Z]aeg-OH together with 0.12 M DCC in 3.0 ml 50% DMF/CH$_2$Cl$_2$ or (2) 0.12 M BocTaeg-OH together with 0.12 M DCC in 3.0 ml 50% DMF/CH$_2$Cl$_2$ ("Synthetic Protocol 9"). Each coupling reaction was allowed to proceed overnight with shaking. The synthesis was monitored by the ninhydrin reaction, which showed close to quantitative incorporation of all the residues. During the synthesis, a small portion of H—C(Z)aeg-[Taeg]$_5$-Lys(ClZ)-MBHA resin was taken out for HF cleavage.

(b) Cleavage, Purification, and Identification of H-Caeg-[Taeg]$_5$-Lys-NH$_2$

The protected Boc-C[Z]aeg-[Taeg]$_5$-Lys(ClZ)-MBHA resin was treated as described in Example 27c to yield about 3.0 mg of crude material upon HF cleavage of 37.5 mg dry H—C[Z]aeg-[Taeg]$_5$-Lys(ClZ)-MBHA resin. About 0.7 mg of the crude product was purified to give about 0.5 mg of H-Caeg-[Taeg]$_5$-Lys-NH$_2$.

(c) Cleavage, Purification, and Identification of H-[Taeg]$_2$-Caeg-[Taeg]$_5$-Lys-NH$_2$ The protected Boc-[Taeg]$_2$-C[Z]aeg-[Taeg]$_5$-Lys(ClZ)-MBHA resin was treated as described in Example 27c to yield about 37.7 mg of crude material upon HF cleavage of 118.6 mg dry H-[Taeg]$_2$-C[Z]aeg-[Taeg]$_5$-Lys(ClZ)-MBHA resin.

EXAMPLE 115

Solid-Phase Synthesis of H-[Caeg]$_5$-Lys-NH$_2$, H-[Caeg]$_6$-Lys-NH$_2$, H-[Caeg]$_8$-Lys-NH$_2$, and H-[Caeg]$_{10}$-Lys-NH$_2$ (a) Stepwise Assembly of Boc-[C(Z)aeg]$_{10}$-Lys(ClZ)-MBHA Resin and Shorter Fragments.

About 5 g of wet Boc-Lys(ClZ)-MBHA resin (substitution=0.3 mmol Lys/g) was placed in a 30 ml SPPS reaction vessel. Boc-[C(Z)aeg]$_{10}$-Lys(ClZ)-MBHA resin was assembled by single in situ DCC coupling of the first three residues with 0.1 M of BocC(Z)aeg-OH together with 0.1 M DCC in 10 ml 50% DMF/CH$_2$Cl$_2$ ("Synthetic Protocol 9") and by single in situ DIC coupling of the remaining seven residues with 0.1 M of BocC(Z)aeg-OH together with 0.1 M DIC in 10 ml 50% DMF/CH$_2$Cl$_2$ ("Synthetic Protocol 10"). All the coupling reactions were allowed to proceed overnight. The synthesis was monitored by the ninhydrin reaction, which showed close to quantitative incorporation of all residues. During the synthesis, portions of the shorter fragments H-[C(Z)aeg]$_5$-Lys(ClZ)-MBHA resin, H-[C(Z)aeg]$_6$-Lys(ClZ)-MBHA resin, H-[C(Z)aeg]$_7$-Lys(ClZ)-MBHA resin, H-[C(Z)aeg]$_8$-Lys(ClZ)-MBHA resin, and H-[C(Z)aeg]$_9$-Lys(ClZ)-MBHA resin were taken out for HF cleavage.

(b) Cleavage, Purification, and Identification of H-[Caeg]$_5$-Lys-NH$_2$

The protected Boc-[C(Z)aeg]$_5$-Lys(ClZ)-MBHA resin was treated as described in Example 27c to yield about 10.8 mg of crude material upon HF cleavage of 60.1 mg dry H-[C(Z)aeg]$_5$-Lys(ClZ)-MBHA resin.

(c) Cleavage, Purification, and Identification of H-[Caeg]$_6$-Lys-NH$_2$

The protected Boc-[C(Z)aeg]$_6$-Lys(ClZ)-MBHA resin was treated as described in Example 27c to yield about 13.4 mg of crude material upon HF cleavage of 56.2 mg dry H-[C(Z)aeg]$_6$-Lys(ClZ)-MBHA resin.

(d) Cleavage, Purification, and Identification of H-[Caeg]$_8$-Lys-NH$_2$

The protected Boc-[C(Z)aeg]$_8$-Lys(ClZ)-MBHA resin was treated as described in Example 27c to yield about 16.8 mg of crude material upon HF cleavage of 65.6 mg dry H-[C(Z)aeg]$_8$-Lys(ClZ)-MBHA resin.

(e) Cleavage, Purification, and Identification of H-[Caeg]$_{10}$-Lys-NH$_2$

The protected Boc-[C(Z)aeg]$_{10}$-Lys(ClZ)-MBHA resin was treated as described in Example 27c to yield about 142.4 mg of crude material upon HF cleavage of 441 mg dry H-[C(Z)aeg]$_{10}$-Lys(ClZ)-MBHA resin.

EXAMPLE 116

Solid-Phase Synthesis of H-[Taeg]$_2$-Caeg-[Taeg]$_2$-Caeg-[Taeg]$_4$-Lys-NH$_2$ (a) Stepwise Assembly of Boc-[Taeg]$_2$-C(Z)aeg-[Taeg]$_2$-C(Z)aeg-[Taeg]$_4$-Lys(ClZ)-MBHA Resin About 0.3 g of wet H-[Taeg]$_2$-C(Z)aeg-[Taeg]$_4$-Lys(ClZ)-MBHA resin from the earlier synthesis of Boc-[Taeg]$_5$-C(Z)aeg-[Taeg]$_4$-Lys(ClZ)-MBHA resin was placed in a 5 ml SPPS reaction vessel. After coupling of the next residue five times, a total incorporation of BocC(Z)aeg of 87% was obtained. The five repeated couplings were carried out with 0.18 M BocC(Z)aeg-OPfp in 2 ml of TFE/CH$_2$Cl$_2$ (1:2, v/v), 2 ml of TFE/CH$_2$Cl$_2$ (1:2, v/v), 2 ml of TFE/CH$_2$Cl$_2$ (1:2, v/v) with two drops of dioxane and two drops of DIEA (this condition gave only a few per cent coupling yield), 2 ml of TFE/CH$_2$Cl$_2$ (1:2, v/v) plus 0.5 g phenol, and 1 ml of CH$_2$Cl$_2$ plus 0.4 g of phenol, respectively. The two final Taeg residues were incorporated close to quantitatively by double couplings with 0.25 M BocTaeg-OPfp in 25% phenol/CH$_2$Cl$_2$. All couplings were allowed to proceed overnight.

(b) Cleavage, Purification, and Identification of H-[Taeg]$_2$-Caeg-[Taeg]$_2$-Caeg-[Taeg]$_4$-Lys-NH$_2$ The protected Boc-[Taeg]$_2$-C(Z) aeg-[Taeg]$_2$-C(Z)aeg-[Taeg]$_4$-Lys(ClZ)-MBHA resin was treated as described in Example 27c to yield about 7 mg of crude material upon HF cleavage of 80.7 mg dry H-[Taeg]$_2$-C(Z)aeg-[Taeg]$_2$-C(Z)aeg-[Taeg]$_4$-Lys(ClZ)-MBHA resin. The crude product was purified to give 1.2 mg of H-[Taeg]$_2$-Caeg-[Taeg]$_2$-Caeg-[Taeg]$_4$-Lys-NH$_2$ (>99.9% purity).

EXAMPLE 117

Synthesis of a PNA with Two Anti Parallel Strands Tied Together

Synthesis of H-[Taeg]-[Taeg]-[Taeg]-[Gaeg]-[Taeg]-[Taeg]-[Taeg]-[6-AHA]-[aeg]-[6-AHA]-[Taeg]-[Taeg]-[Taeg]-[Aaeg]-[Taeg]-[Taeg]-[Taeg]-LYS-NH$_2$ (6-AHA=6-aminohexanoic acid) (FIG. 17)

The protected PNA was assembled onto a Boc-Lys(ClZ) modified MBHA resin with a substitution of approximately 0.30 mmol/g. Capping of uncoupled amino groups was only carried out before the incorporation of the BocGaeg-OH monomer. Synthesis was initiated on 1.00 g (dry weight) of preswollen (overnight in DCM) and neutralized Boc-Lys (ClZ)-MBHA resin. The incorporation of the monomers followed the protocol of Example 42 and Example 81. The coupling reaction was monitored by qualitative ninhydrin reaction (kaiser test). In case of a positive Kaiser test, the coupling reaction was repeated until the test showed no coloration of the beads. Final deprotection, cleavage from support, and purification were performed according to standard procedures.

EXAMPLE 118

Alternative Protecting Group Strategy for PNA-synthesis (FIG. 18)

(a) Synthesis of Test Compounds 2-amino-6-O-benzyl purine. To a solution of 2.5 g (0.109 mol) of sodium in 100 ml of benzyl alcohol was added 10.75 g (0.063 mol) of 2-amino-6-chloropurine. The mixture was stirred for 12 h at 120 0° C. The solution was cooled to room temperature and neutralized with acetic acid and extracted with 10 portions of 50 ml of 0.2 N sodium hydroxide. The collected sodium hydroxide phases were washed with 100 ml of diethyl ether and neutralized with acetic acid, whereby precipitation starts. The solution was cooled to 0° C. and the yellow precipitate was collected by filtration. Recrystallization from ethanol gave 14.2 g 92% of pure white crystals of the target compound. 1H-NMR (250 MHz--DMSO-d6) d ppm: 8-H, 7.92; benzyl aromatic, 7.60–7.40; 2NH2, 6.36; benzyl CH2, 5.57.

(2-amino-6-O-benzyl purinyl)methylethanoate. A mixture of 5 g (0.0207 mol) of 2-amino-6-O-benzyl-purine, 30 ml of DMF and 2.9 g (0.021 mol) of potassium carbonate was stirred at room temperature. Methyl bromoacetate (3.2 g; 1.9 ml; 0.0209 mol) was added dropwise. The solution was filtrated after 4 h and the solvent was removed under reduced pressure (4 mmHg, 40° C.). The residue was recrystallized two times from ethyl acetate to give 3.7 g (57%) of the target compound. 1H-NMR (250 MHz, DMSO-d6) d ppm: 8-H, 7.93; benzyl aromatic 7.4–7.6; 2-NH$_2$, 6.61; benzyl CH2, 5.03; CH2, 5.59; OCH3, 3.78.

(2N-p-Toluene sulfonamido-6-O-benzyl purinyl) methyl ethanoate. To a solution of 0.5 g (1.6 mmol) of (2-amino-6-O-benzyl purinyl) methyl ethanoate in 25 ml methylene chloride was added 0.53 g (1.62 mmol) of p-toluenesulfonic anhydride and 0.22 g (1.62 mmol) of potassium carbonate. The mixture was stirred at room temperature. The mixture was filtered and the solvent was removed at reduced pressure (15 mmHg, 40° C.). Diethyl ether was added to the oily residue. The resulting solution was stirred overnight, whereby the target compound (0.415 mg; 55%) precipitated and was collected by filtration. 1H-NMR (250 MHz, DMSO-d6) d ppm: 8-H, 8.97; aromatic 7.2–7.8; benzyl CH2, 5, 01; CH2, 4.24; OCH3, 3.73; CH3, 2.43.

(b) Stability of the Tosyl Protected Base-residue in TFA and HF

The material was subjected to the standard deprotection conditions (TFA-deprotection) and the final cleavage conditions with HF. The products were then subjected to HPLC-analysis using a 4$\mu$ RCM 8×10 Nova pack column and solvents A (0.1% TFA in water) and B (0.1% TFA in acetonitrile) according to the following time gradient with a flow of 2 ml/min.

| Time | % A | % B |
| --- | --- | --- |
| 0 | 100 | 0 |
| 5 | 100 | 0 |
| 35 | 0 | 100 |
| 37 | 0 | 100 |
| 39 | 100 | 0 |

The following retention times were found: (a) Compound 1: 30.77 min; (b) compound 2: 24.22 min; and (c) compound 3: 11.75 min. The analysis showed that the O6-benzyl group was removed both by TFA and HF, whereas there was no cleavage of the tosyl group in TFA, but quantitative removal in HF under the standard cleavage conditions.

EXAMPLE 119

5-Bromouracil-N$^1$-methyl Acetate

5-Bromouracil (5.00 g; 26.2 mmol) and potassium carbonate (7.23 g; 52.3 mmol) were suspended in DMF (75 ml). Methyl bromoacetate (2.48 ml; 26.1 mmol) was added over a period of 5 min. The suspension was stirred for 2 h at room temperature, and then filtered. The solid residue was washed twice with DMF, and the combined filtrates were evaporated to dryness, in vacuo. The residue was an oil containing the title compound, DMF and some unidentified impurities. It is not necessary to purify the title compound before hydrolysis. $^1$H-NMR (DMSO-d$_6$, 250 MHz); 8.55 (impurity); 8.27 (CBr=CHN); 8.02 (impurity); 4.76 (impurity); 4.70 (impurity); 4.62 (NCH$_2$COOCH$_3$); 3.78 (COOCH$_3$); 2.96 (DMF); 2.80 (DMF). $^{13}$C-NMR (DMSO-d$_6$, 250 MHz); 168.8 (COOCH$_3$); 172.5 (CH=CBrCON); 161.6 (DMF); 151.9 (NCON); 145.0 (CO—CBr=CHN); 95.6 (CO CBr=CHN); 52.6 (impurity); 52.5 (OCH$_3$); 49.7 (impurity); 48.8 (NCH$_2$COOMe); 43.0 (impurity); 36.0 (DMF). UV (Methanol; $_{max}$nm); ; 226; 278. IR (KBr; cm$^{-1}$_; 3158s (_NH); 1743vs (_C=O, COOMe) ; 1701vs (_C=O, CONH); 1438vs (δ CH, CH$_3$O) ; 1223vs (_C—O, COOMe); 864 m (δ CH, Br=C—H). FAB-MS m/z (assignment): 265/263 (M+H).

EXAMPLE 120

(5-Bromouracil)acetic Acid

Water (30 ml) was added to the oil of the crude product from Example 119 and the mixture was dissolved by adding sodium hydroxide (2M, 60 ml). After stirring at 0° C. for 10 min, hydrochloric acid (4M, 45 ml) was added to pH=2 and the title compound precipitated. After 50 min, the solid residue was isolated by filtration, washed once with cold water, and then dried in vacuo over sicapent. Yield: 2.46 g (38%). Mp, 250°–251° C. Anal. for C$_6$H$_5$BrN$_2$O$_4$. Found (calc.): C: 28.78 (28.94); H: 2.00 (2.02); Br: 32.18 (32.09); N: 11.29 (11.25). $^1$H-NMR (DMSO-d$_6$, 250 MHz): 12.55 (1H.s, COOH); 11.97 (1H, s, NH); 8.30 (1H, s, C=C—H); 4.49 (2H, s, NCH$_2$COOH). $^{13}$C-NMR (DMSO-d$_6$, 250 MHz); 169.4 (COOH); 159.8 (NHCOCBr=CH); 150.04 (N CON); 145.8 (COCBr=CHN); 94.6 (COCBr=CHN); 48.8 (NCH$_2$COOH). UV (Methanol; $_{max}$nm); 226; 278. IR (KBr; cm$^{-1}$); 3187s (_NH); 1708vs (_C=O, COOH); 1687vs; 1654VS (_C=O, CONH); 1192s (_C—O, COOH); 842 m (δ CH, Br—C=C—H). FAB-MS m/z (assignment, relative intensity); 251/249 (M+H, 5).

EXAMPLE 121

N-(Boc-aminoethyl)-N-(5-bromouracil) methylenecarbonoylglycine Ethyl Ester

Boc-aminoethylglycine ethyl ester (1.80 g; 7.30 mmol) was dissolved in DMF (10 ml). Dhbt-OH (1.31 g; 8.03 mmol) was added, whereby a precipitate was formed. DMF (2×10 ml) was added until the precipitate was dissolved. The product of Example 120 (2.00 g; 8.03 mmol) was added slowly to avoid precipitation. Methylene chloride (30 ml) was added, and the mixture was cooled to 0° C. and then filtered. The precipitate, DCU, was washed twice with methylene chloride. To the combined filtrate was added methylene chloride (100 ml). The mixture was washed with half saturated NaHCO$_3$-solution (3×100 ml, H$_2$O:saturated NaHCO$_3$-solution 1:1 v/v), then with dilute KHSO$_4$-solution (2×100 ml, H$_2$O:saturated KHSO$_4$-solution 4:1 v/v), and finally with saturated NaCl-solution (1×100 ml). The organic phase was dried over magnesium sulphate, filtered, and evaporated to dryness in vacuo (about 15 mmHg and then about 1 mmHg). The residue was suspended in methylene chloride (35 ml), stirred for 45 min at room temperature, and filtered (the precipitate was DCU). Petroleum ether (2 volumes) was added dropwise to the filtrate at 0° C., whereby an oil precipitated. The liquor was decanted and the remaining oil dissolved in methylene chloride (20–50 ml). Precipitated was effected by the addition of petroleum ether (2 volumes). This procedure was repeated 5 times until an impurity was removed. The impurity can be seen at TLC with 10% MeOH/CH$_2$Cl$_2$ as the developing solvent. The resulting oil was dissolved in methylene chloride (25 ml) and evaporated to dryness in vacuo, which caused solidification of the title compound. Yield: 2.03 g ((58%). Mp. 87°–90° C. Anal. for C$_{17}$H$_{25}$BrN$_4$O$_7$. Found (calc.): C: 42.33 (42.78); H: 5.15 (5.28); Br: 17.20 (16.74); N: 1.69 (11.74). $^1$H-NMR (DMSO-d$_6$, 250 MHz, J in Hz): 1.93 & 11.92 (1H, s, C=ONHC=O); 8.09 & 8.07 (1H, s, C=C—H); 7.00 & 6.80 (1H, t, b, BocNH); 4.80 & 4.62 (2H, s, NCH$_2$CON); 4.35 & 4.24 (2H, s, NCH$_2$COOEt); 4.27–4.15 (2H, m's, COOCH$_2$CH$_3$O); 3.47–3.43 (2H, m's, BocNHCH$_2$CH$_2$N); 3.28–3.25 & 3.12–3.09 (2H, m's, Boc-NHCH$_2$CH—$_2$N) : 1.46 & 1.45 (9H, s, $^t$Bu); 1.26 & 1.32 (3H, t, J=7.1, COOCH$_2$CH$_3$). $^{13}$C—NMR (DMSO-d$_6$, 250 MHz); 169.3 & 169.0 ($^t$BuOC=O); 167.4 & 167.1 ( COOEt); 159.8 (C=C—CON); 155.9 (NCH$_2$CON); 150.4 (NCON); 145.9 (COCBr—CHN); 94.5 (COCBr=CHN); 78.2 (Me$_3$C); 61.3 & 60.7 (COCH$_2$CH$_3$); 49.1 & 48.0 (N CH$_2$COOH); 48.0 & 47.0 (NCH$_2$CON); 38.6 (BocNHCH$_2$ CH$_2$N); 38.2 (BocNHCH$_2$CH$_2$N); 26.3 (C(CH$_3$)$_3$); 14.1 (COCH$_2$CH$_3$). UV (Methanol; $_{max}$NM) : 226; 280. IR (KBr, CM$^{-1}$): 3200ms, broad (_NH); 168vs, vbroad (_C=O, COOH, CONH); 1250s (_C—O, COOEt); 1170s (_C—O, COO$^t$Bu); 859m (δ CH, Br—C=C—H). FAB-MS m/z (assignment, relative intensity): 479/477 (M+H, 5); 423/421 (M+2H-$^t$Bu, 8); 379/377 (M+2H-Boc, 100); 233/231 (M-backbone, 20).

EXAMPLE 122

N-(Boc-aminoethyl)-N-(5-bromouracyl-N$^1$-methylenecarbonoyl)glycine

The product of Example 121 (1.96 g; 4.11 mmol) was dissolved in methanol (30 ml) by heating, and then cooled to 0° C. Sodium hydroxide (2M, 30 ml) was added, and the mixture stirred for 30 min. HCl (1M, 70 ml) was added to pH=2.0. The water phase was extracted with ethyl acetate (3×65 ml+7×40 ml). The combined ethyl acetate extractions were washed with saturated NaCl-solution (500 ml). The ethyl acetate phase was dried over magnesium sulphate, filtered and evaporated to dryness in vacuo. Yield: 1.77 g (96%). Mp. 92°–97° C. Anal. for C$_{15}$H$_{21}$BrN$_4$O$_7$. Found (calc.): C: 40.79 (40.10); H: 5.15 (4.71); Br: 14.64 (17.70); N: 11.35 (12.47). $^1$H-NMR (DMSO-d$_6$, 250 MHz, J in Hz): 12.83 (1H, s, COOH); 11.93 & 11.91 (1H, s, C=ON HC=O) ; 8.10 & 8.07 (1H, s, C=C—H); 7.00 & 6.81 (1H, t, b, BocNH); 4.79 & 4.61 (2H, s, NCH$_2$CON); 4.37 & 4.25 (2H, s, NCH$_2$COOH); 3.46–3.39 (2H, m's, BocNHCH$_2$C H$_2$N); 3.26–3.23 & 3.12–3.09 (2H, m's, BocNHCH$_2$CH$_2$N); 1.46 (9H, s, $^t$Bu). $^{13}$C-NMR 9DMSO-d$_6$, 250 MHz); 170.4 ($^t$BuOC=O); 166.9 (COOH); 159.7 (C=C—CON); 155.8 (NCH$_2$CON); 150.4 (NCON); 145.9 (COCBr=CHN); 94.4 (COCBr=CHN); 78.1 (Me$_3$C); 49.1 & 48.0 (NCH$_2$COOH); 47.7 & 47.8 (NCH$_2$CON); 38.6 (BocNHC$_2$CH$_2$N); 38.1 (Boc NHCH$_2$CH$_2$N); 28.2 (C(CH$_3$)$_3$). UV (Methanol;

$_{max}$nm) ; 226; 278. IR (KBr, cm$^{-1}$): 3194ms, broad (_NH); 1686vs, vbroad (_C=O COOH, CONH); 1250s (_C—O, COOH); 1170s (_C—O, COO$^t$Bu); 863m (δ CH, Br—C=C—H). FAB-MS m/z (assignment, relative intensity): 449/451 (M+H, 70); 349/351 (M+2H-Boc, 100); 231/233 (M-backbone, 20).

EXAMPLE 123

Uracil-N$^1$-methyl Acetate

Uracil (10.0 g; 89.2 mmol) and potassium carbonate (24.7 g; 178 mmol) were suspended in DMF (250 ml). Methyl bromoacetate (8.45 ml; 89.2 mmol) was added over a period of 5 min. The suspension was stirred overnight under nitrogen at room temperature, and then filtered. TLC (10% methanol in ethylene chloride) indicated incomplete conversion of uracil. The solid residue was washed twice with DMF, and the combined filtrates were evaporated to dryness in vacuo. The precipitate was suspended in water (60 ml) and HCl (2.5 ml, 4M) was added to pH=2. The suspension was stirred for 30 min at 0° C., and then filtered. The precipitated title compound was washed with water and dried, in vacuo, over sicapent. Yield: 9.91 g (60%). Mp. 182°–183° C. Anal. for C$_6$H$_8$N$_2$O$_4$. Found (calc.): C: 45.38 (45.66); H: 4.29 (4.38); N: 15.00 (15.21). $^1$H-NMR (DMSO-d$_6$, 250 MHz, J in Hz): 1.47 (1H, s, NH); 7.68 (1H, d, J$_{H-C=C-H}$=7.9), CH=CHN); 5.69 (1H, d, J$_{H-C=C-H}$=7.9), CH=CHN); 4.59 (2H, s, NCH$_2$COOMe); 3.76 (3H, s, COOCH$_3$). $^{13}$C-NMR (DMSO-d$_6$, 250 MHz); 168.8 (COOMe); 164.0 (C=C—CON); 151.1 (NCON); 146.1 (COCH=CHN); 101.3 (COCH=CHN); 52.5 (COOCH$_3$); 48.7 (NCH$_2$COOMe). UV (Methanol; $_{max}$nm): 226; 261. IR (KBr; cm$^{-1}$); 3164s (_NH); 1748vs (_C=O, COOMe); 1733vs (_C=O, CONH); 1450vs (δ CH, CH$_3$O); 1243VS (_C—O, COOMe); 701m (δ CH, H—C=C—H). FAB-MS m/z (assignment); 185 (M+H).

EXAMPLE 124

Uracilacetic Acid

Water (90 ml) was added to the product of Example 123 (8.76 g; 47.5 mmol), followed by sodium hydroxide (2M, 40 ml). The mixture was heated for 40 min, until all the methyl ester has reacted. After stirring at 0° C. for 15 min, hydrochloric acid (4M, 25 ml) was added to pH=2. The title compound precipitated and the mixture was filtered after 2–3 h. The precipitate was washed once with the mother liquor and twice with cold water and dried in vacuo over sicapent. Yield: 6, 0.66 g (82%). Mp. 288°–289° C. Anal. for C$_6$H$_6$N$_2$O$_4$. Found (calc.): C: 42.10 (42.36), H: 3.43 (3.55); N: 16.25 (16.47)/$^1$H-NMR (DMSO-d$_6$), 250 MHz, J in Hz): 13.19 (1H, s, COOH); 11.41 (1H, s, NH); 7.69 (1H, d, J$_{H-C=C-H}$=7.8, J$_{H-C=C-N-H}$=2.0, coch=chn) ; 4.49 (2H, s, NCH$_2$COOH) . $^{13}$C-NMR (DMSO-d6, 2509 MHz); 169.9 (COOH); 163.9 (CH=CHCON); 151.1 (NCON); 146.1 (COCH=CHN); 100.9 (COCH=CHN); 48.7 NCH$_2$COOH. UV (Methanol; $_{max}$nm): 246; 263. IR (KBr; cm$^{-1}$): 3122s (_NH); 1703vs (_C=O, COOH); 1698vs, 1692vs (_C=O, CONH); 1205s (_C—O, COOH); 676 (δ CH, H—C=C—H). FAB-MS m/z (assignment): 171 (M+H).

EXAMPLE 125

N-(Bocaminoethyl)-N-(uracil-N$^1$-methylenecarbonoyl)glycine Ethyl Ester (Bocaminoethyl)glycine ethyl ester (2.00 g; 8.12 mmol) was dissolved in DMF (10 ml). Dhbt-OH (1.46 g; 8.93 mmol) was added and a precipitate was formed. DMF (2×10 ml) was added until all was dissolved. The product of Example 124 (1.52 g; 8.93 mmol) was added slowly to avoid precipitation. Methylene chloride (30 ml) was added, and the mixture was cooled to 0° C., whereafter DDC (2.01 g; 9.74 mmol) was added. The mixture was stirred for 1 h at 0° C., at 2 h at room temperature, and then filtered. The precipitated DCU was washed twice with methylene chloride. To combined filtrate was added methylene chloride (100 ml), and the solution washed with half-saturated NaHCO3-solution (3×100 ml, H$_2$O: saturated NaHCO$_3$-solution 1:1 v/v), then with dilute KHSO$_4$-solution (2×100 ml, H$_2$O: saturated KHSO$_4$-solution 4:1 v/v) and finally with saturated NaCl-solution (1×100 ml). The organic phase was dried over magnesium sulphate, filtered and evaporated to dryness in vacuo (about 15 mmHg and then about 1 mmHg). The residue was suspended in methylene chloride (32 ml), and stirred for 35 min at room temperature, and 30 min at 0° C., and then filtered. The precipitate (DCU) was washed with methylene chloride. Petroleum ether (2 volumes) was added dropwise to the combined filtrate at 0° C., which caused separation of an oil. The mixture was decanted, the remaining oil was then dissolved in methylene chloride (20 ml), and then again precipitated by addition of petroleum ether (2 volumes). This procedure was repeated 5 times until an impurity was removed. The impurity can be seen by TLC with 10% MeOH/CH$_2$Cl$_2$ as the developing solvent. The resulting oil was dissolved in methylene chloride (20 ml) and evaporated to dryness in vacuo, which caused solidification of the title compound. Yield: 1.71 g (53%). Mp. 68.5°–75.7° C. Anal for C$_{17}$H$_{26}$N$_4$O$_7$. Found (calc.): C: 50.61 (51.25); H: 6.48 (6.58); N: 13.33 (14.06). $^1$H-NMR (DMSO-d$_6$, 250 MHz, J in Hz): 11.36 (1H, s, C=ON HC=O); 7.51 & 7.47 (1H, d, J$_{H-C=C-H}$+ 6.1; COCH=X—H); 7.00 & 6.80 (1H, t, b, BocNH); 5.83 & 5.66 (1H , d, J$_{H-C=C-H}$=5.7, COCH=CH); 4.78 & 4.60 (2H, s, NCH$_2$CON) ; 4.37 & 4.12 (2H, s, NCh$_2$COOEt); 4.30–4.15 (2H, m's, COOCH$_2$CH$_3$); 3.49–3.46 (2H, m's, BocNHCH$_2$CH$_2$n); 3.27 3.23 & 3.11–3.09 (2H, m's, Boc-NHCH$_2$CH$_2$N; 1.46 (9H, s, $^t$Bu); 1.39–1.23 (3H, m's, COOCH$_2$CH$_3$). $^{13}$C-NMR (DMSO-d$_6$, 250 MHz): 169.4 & 169.0 ($^t$BuOC=O); 167.6 & 167.3 (COOEt); 163.8 (CH=CHCON); 155.8 (NCH$_2$CON); 151.0 (NCON); 146.3 (COCH=CHN); 100.8 (COCH=CHN); 78.1 (Me$_3$C); 61.2 & 60.6 (COOCH$_2$CH$_3$); 49.1 (NCH$_2$COOEt); 47.8 & 47.0 (NCH$_2$CON); 38.6 (BocNHCH$_2$CH$_2$N); 38.1 & 37.7 (BocNHCH$_2$N); 28.2 (C(CH$_3$)$_3$); 14.1 (CO—OCH$_2$CH$_3$. UV (Methanol; $_{max}$nm); 226; 264. IR (KBr; cm$^{-1}$): 3053m (_NH); 1685vs, vbroad (_C=O, COOH, CONH); 1253s (_C—O, COOEt); 1172s (_C—O, COO$^t$Bu); 718w (δ CH, C—C—C—H), FAB-MS m/z (assignment, relative intensity); 399 (M+H, 35); 343 (M+2H-$^t$Bu, 100); 299 (M+2H-Boc, 100); 153 (M-backbone, 30).

EXAMPLE 126

N-(Bocaminoethyl)-N-(uracilmethylenecarbonoyl) glycine

The product of Example 125 (1.56 g; 3.91 mmol) was dissolved in methanol (20 ml) and then cooled to 0° C. Sodium hydroxide (2M, 20 ml) was added, and the mixture was stirred for 75 min at 0° C. Hydrochloric acid (1M, 46 ml) was added to pH=2.0. The water phase was extracted was ethyl acetate (3×50 ml+7×30 ml). The combined ethyl acetate extractions were washed with saturated NaCl solution (360 ml). The ethyl acetate phase was dried over magnesium sulphate, filtered, and evaporated to dryness, in vacuo. The residue was dissolved in methanol and evaporated to dryness, in vacuo. Yield: 0.55 g (38%). Mp 164°–170° C. Anal. for $C_{15}H_{22}N_4O_7$. Found (calc.): C: 46.68 (48.65); H: 6.03 (5.99); N: 1461 (15.13). $^1$H-NMR (DMSO-$d_6$, 250 MHz, J in Hz); 12.83 (1H, s, COO$\underline{H}$); 11.36 (1H, s, C=ON$\underline{H}$C=O); 7.52–7.45 (1H, m's, COCH=C$\underline{H}$N); 7.00 & 6.82 (1H, t, b, BocN$\underline{H}$); 5.67–5.62 (1H, M's, COC$\underline{H}$=CHN); 4.76 & 4.58 (2H, s, NC$H_2$CON); 4.26 & 4.05 (2H, s, NC$\underline{H}_2$COOH); 3.46–3.39 (2H, m's, BocNHCH$_2$C$\underline{H}_2$N); 3.25–3.23 & 3.15–3.09 (2H, m's, BocNHC$\underline{H}_2$CH$_2$N); 1.46 (9H, s, $^t$Bu). $^{13}$C-NMR (DMSO-$d_6$, 250 MHz); 170.5 ($^t$BuO$\underline{C}$=O); 167.2 (COOH); 163.9 (C=C—$\underline{C}$ON); 155.8 (N$\underline{C}$H$_2$CON); 151.1 (N$\underline{C}$ON); 146.4 (CO$\underline{C}$H=CHN) ; 100.8 (CO$\underline{C}$H=CHN) ; 78.1 (Me$_3$$\underline{C}$) ; 49.1 & 47.8 (N$\underline{C}$H$_2$ COOH); 47.6 & 46.9 (N$\underline{C}$H$_2$CON); 38.6 (BocNHCH$_2$$\underline{C}$H$_2$N); 38.1 & 37.6 (BocNH$\underline{C}$H$_2$CH$_2$N); 28.2 (C($\underline{C}$H$_3$)$_3$). UV (Methanol; $_{max}$nm); 226; 264. IR (KBr; cm$^{-1}$); 3190 (_NH); 1685vs, vbroad (_C=O, COOH, CONH) ; 1253s (_C—O, COOH); 1171s (_C—O, COO$^t$BU); 682w (δ CH, H—C=C—H). FAB-MS m/z (assignment, relative intensity): 371 (M+H, 25); 271 (M+H -Boc, 100).

EXAMPLE 127

H-U10-LysNH$_2$

Synthesis of the title compound was accomplished by using "Synthetic Protocol 10". The synthesis was initiated on approximately 100 mg Lys(ClZ)-MHBA-resin. The crude product (12 mg) was pure enough for hybridization studies. The hybrid between 5'-(dA)10 and H-U10 had Tm of 67.5° C.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A composition comprising a first polymeric strand and a second polymeric strand, wherein:
   a plurality of ligands on said first strand hydrogen bond with ligands on said second strand; and
   each of said strands has the formula:

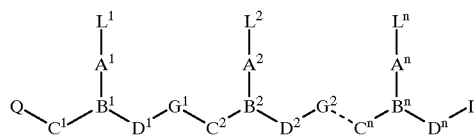

wherein:
   n is at least 2,
   each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands;
   each of $C^1$–$C^n$ is identical and has the formula $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;
   each of $D^1$–$D^n$ is identical and has the formula $(CR^6R^7)_z$ where $R^6$ and $R^7$ are as defined above;

each of y and z is zero or an integer from 1 to 10, the sum y+z being greater than 2 but not more than 10;

each of $G^1$–$G^{n-1}$ is identical and has the formula —$NR^3CO$—, —$NR^3CS$—, —$NR^3SO$— or —$NR^3SO_2$—, in either orientation, where $R^3$ is as defined above;

each of $A^1$–$A^n$ and $B^1$–$B^n$ are selected such that $A^1$–$A^n$ are identical and $B^1$–$B^n$ are identical and:
   (a) A is a group of formula (IIa), (IIb) or (IIc), and B is N or $R^3N^+$; or
   (b) A is a group of formula (IId) and B is CH;

(IIa)

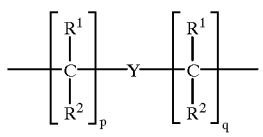

(IIb)

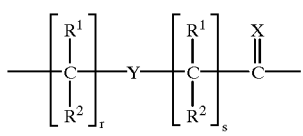

(IIc)

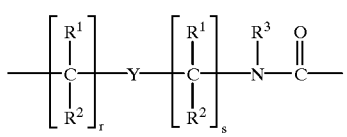

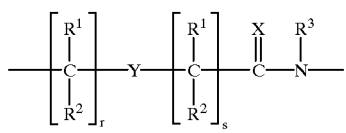

where:

X is O, S, Se, NR³, CH₂ or C(CH₃)₂;

Y is a single bond, O, S or NR⁴;

each of p and q is zero or an integer from 1 to 5;

each of r and s is zero or an integer from 1 to 5;

each R¹ and R² is independently selected from the group consisting of hydrogen, (C₁–C₄)alkyl which may be hydroxy- or alkoxy- or alkylthio-substituted, hydroxy, alkoxy, alkylthio, amino and halogen; and each R³ and R⁴ is independently selected from the group consisting of hydrogen, (C₁–C₄)alkyl, hydroxy- or alkoxy- or alkylthio-substituted (C₁–C₄)alkyl, hydroxy, alkoxy, alkylthio and amino;

Q is —CO₂H, —CONR'R", —SO₃H or —SO₂NR'R" or an activated derivative of —CO₂H or —SO₃H; and I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

2. The composition of claim 1 wherein said first and second strands are covalently bound.

3. The composition of claim 1 wherein said first and second strands are not covalently bound.

4. The composition of claim 1 wherein at least one of said purine and pyrimidine nucleobases is adenine, guanine, thymine, uridine or cytosine.

5. The composition of claim 1 wherein each of said first and second polymeric strands comprises a moiety of the formula:

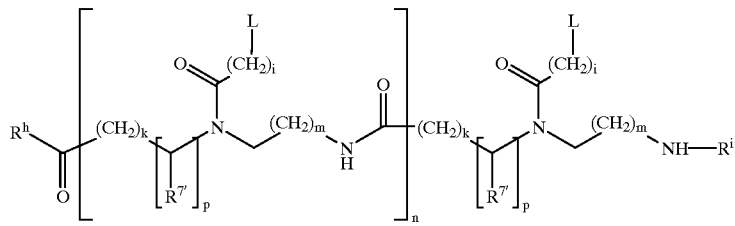

or the formula:

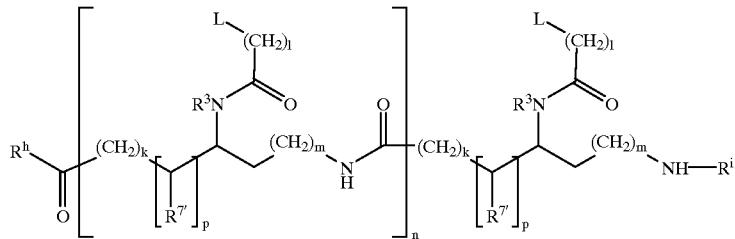

or the formula:

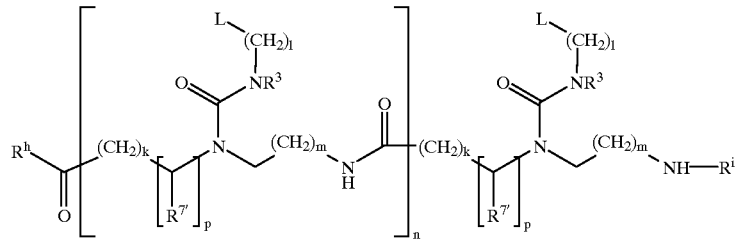

wherein:
   each L is independently selected from the group consisting of hydrogen, phenyl, heterocyclic moieties, naturally occurring nucleobases, and non-naturally occurring nucleobases;
   each $R^{7'}$ is independently selected from the group consisting of hydrogen and the side chains of naturally occurring alpha amino acids;
   n is an integer greater than 1,
   k is an integer from 1 to 5;
   l is an integer from 1 to 5;
   m is an integer from 1 to 5;
   each p is zero or 1;
   $R^h$ is OH, $NH_2$ or —$NHLysNH_2$; and
   $R^i$ is H or $COCH_3$.

6. The composition of claim 5 wherein k is 2.
7. The composition of claim 5 wherein l is 1.
8. A composition comprising a first polymeric strand and a second polymeric strand, wherein each of said first and second polymeric strands comprises a moiety of the formula:

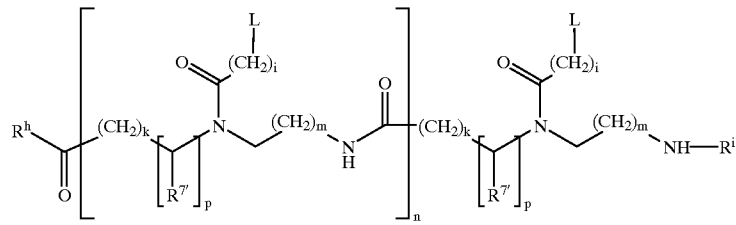

or the formula

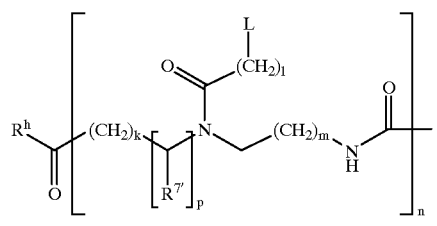

or the formula

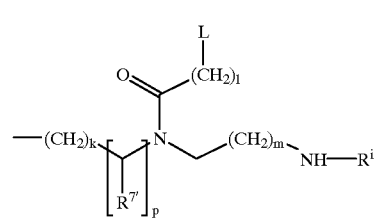

or the formula

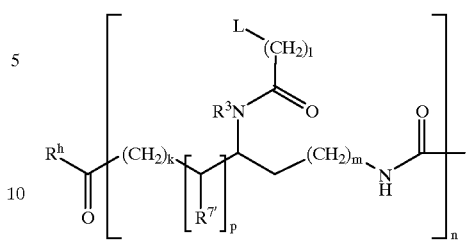

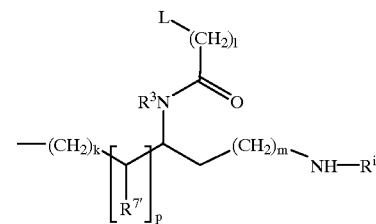

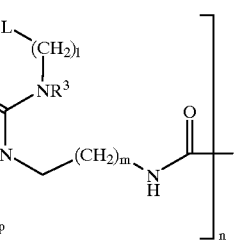

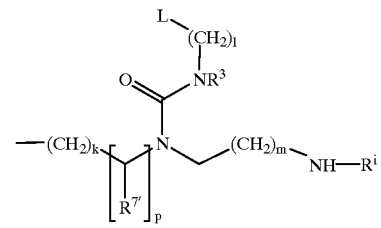

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, $NH_2$ or —$NHLysNH_2$; and $R^i$ is H or $COCH_3$.

9. A process for preparing a double-stranded structure, comprising the steps of providing a first strand and a second strand, and disposing said strands in space relative to one another to form hydrogen bonds therebetween, wherein each of said first and second polymeric strands comprises a moiety of the formula:

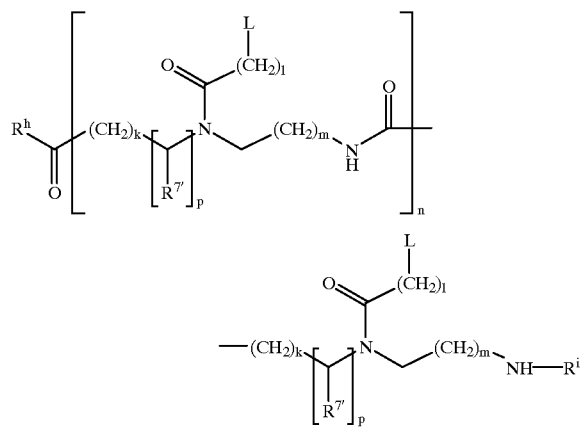

or the formula

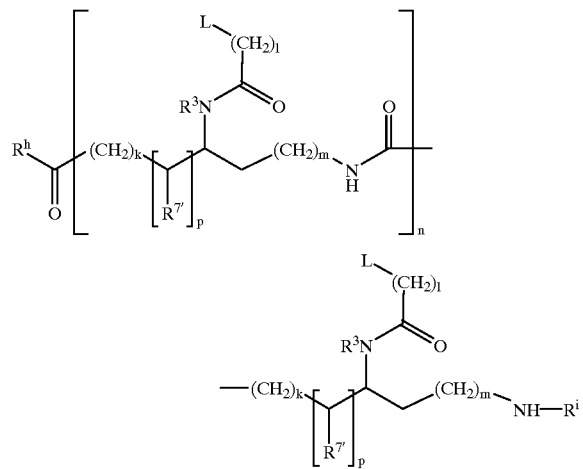

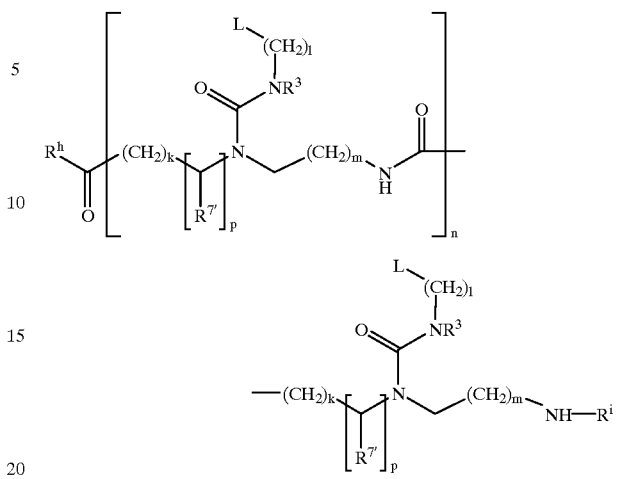

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, $NH_2$ or —$NHLysNH_2$; and $R^i$ is H or $COCH_3$.

10. A process for preparing a double-stranded structure, comprising the steps of providing a first strand and a second strand, and disposing said strands in space relative to one another to form hydrogen bonds therebetween, wherein each of said first and second polymeric strands comprises a moiety of the formula:

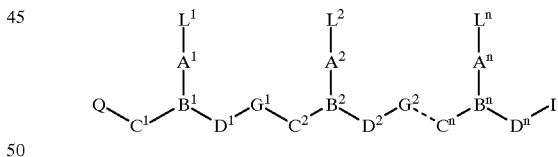

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands;

each of $C^1$—$C^n$ is identical and has the formula $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

each of $D^1-D^n$ is identical and has the formula $(CR^{67})_2$ where $R^6$ and $R^7$ are as defined above;

each of y and z is zero or an integer from 1 to 10, the sum y+z being greater than 2 but not more than 10;

each of $G^1-G^{n-1}$ is identical and has the formula $-NR^3CO-$, $-NR^3CS-$, $-NR^3SO-$ or $-NR^3SO_2-$, in either orientation, where $R^3$ is as defined above;

each of $A^1-A^n$ and $B^1-B^n$ are selected such that $A^1-A^n$ are identical and $B^1-B^n$ are identical and:
(a) A is a group of formula (IIa), (IIb) or (IIc), and B is N or $R^3N^+$; or
(b) A is a group of formula (IId) and B is CH;

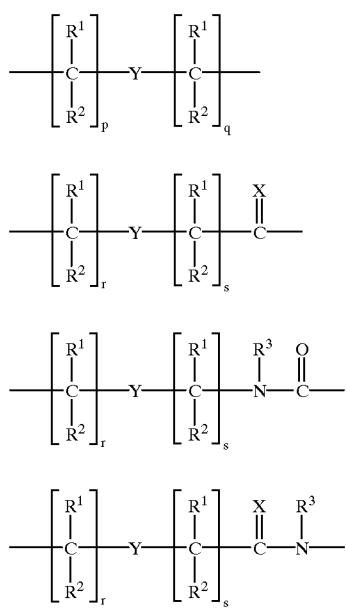

wherein:

X is O, S, Se, $NR^3$, $CH_2$ or $C(CH_3)_2$;

Y is a single bond, O, S or $NR^4$;

each of p and q is zero or an integer from 1 to 5;

each of r and s is zero or an integer from 1 to 5;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

Q is $-CO_2H$, $-CONR'R''$, $-SO_3H$ or $-SO_2NR'R''$ or an activated derivative of $-CO_2H$ or $-SO_3H$; and I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

11. The process of claim 10 wherein at least a portion of said ligands are selected from naturally occurring nucleobases and non-naturally occurring nucleobases.

12. The process of claim 11 wherein said naturally occurring nucleobases are selected to be complementary to nucleobases in a predetermined DNA double strand.

13. The process of claim 10 wherein said first strand and said second strand are covalently bound.

14. The process of claim 10 wherein said first strand and said second strand are not covalently bound.

* * * * *

SEQUENCE LISTING

```
<160> NUMBER OF SEQ ID NOS:  42

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (2)
<223> OTHER INFORMATION: /note= " Heterocyclic base is attached to
      N-acetyl(2-aminoethyl)glycine through the N-acetyl
      group at position 9 of the base."
<221> NAME/KEY: UNSURE
<222> LOCATION: (3)
<223> OTHER INFORMATION: /note= "Heterocyclic base is attached to
      N-acetyl(2-aminoethyl)glycine through the N-acetyl
      group at position 1 of the base."
<221> NAME/KEY: UNSURE
<222> LOCATION: (4)..(6)
<223> OTHER INFORMATION: /note= " Heterocyclic base is attached to
      N-acetyl (2-aminoethyl)glycine throug the N-acetyl group at
      position 9 of the base."
<221> NAME/KEY: UNSURE
<222> LOCATION: (7)..(8)
<223> OTHER INFORMATION: /note = " Heterocyclic base is attached to
      N-acetyl (2-aminoethyl)glycine through the
      N-acetyl group at position 1 of the base."
<221> NAME/KEY: UNSURE
<222> LOCATION: (9)
<223> OTHER INFORMATION: /note = " Heterocyclic base is attached to
      N-acetyl (2-aminoethyl)glycine through the
      N-acetyl group at position 9 of the base."
<221> NAME/KEY: UNSURE
<222> LOCATION: (10)..(11)
<223> OTHER INFORMATION: /note= " Heterocyclic base is attached to
      N-acetyl (2-aminoethyl)glycine through the N-acetyl group
      at position 1 of the base."

<400> SEQUENCE: 1

Gly Xaa Xaa Xaa Xaa Xaa Xaa Xaa Xaa Xaa Xaa Lys
  1               5                  10

<210> SEQ ID NO 2
<211> LENGTH: 12
<212> TYPE: PRT
<213> ORGANISM: Artificial Sequence
```

```
<220> FEATURE:
<223> OTHER INFORMATION: Description of Artificial Sequence: Novel
      Sequence
<221> NAME/KEY: UNSURE
<222> LOCATION: (2)..(3)
<223> OTHER INFORMATION: /note = " Heterocyclic base is attached to
      N-acetyl(2-aminoethyl)glycine through the N-acetyl
      group at position 9 of the base."
<221> NAME/KEY: UNSURE
<222> LOCATION: (4)
<223> OTHER INFORMATION: /note = " Heterocyclic base is attached to
      N-acetyl(2-aminoethyl)glycince through the
      N-acetyl group at position 1 of the base."
<221> NAME/KEY: UNSURE
<222> LOCATION: (5)..(6)
<223> OTHER INFORMATION: /note = "Heterocyclic base is attached to
      N-acetyl(2-aminoethyl)glycine through the N-acetyl
      group at position 9 of the base."
<221> NAME/KEY: UNSURE
<222> LOCATION: (7)..(9)
<223> OTHER INFORMATION: /note = "Heterocyclic base is attached to
      N-acetyl(2-aminoethyl)glycine through the N-acetyl
      group at position 1 of the base."
<221> NAME/KEY: UNSURE
<222> LOCATION: (10)
<223> OTHER INFORMATION: /note = "Heterocyclic base is attached to
      N-acetyl(2-aminoethyl)glycine through the N-acetyl
      group at position 9 of the base."
<221> NAME/KEY: UNSURE
<222> LOCATION: (11)
<223> OTHER INFORMATION: /note = "Heterocyclic base is attached to
      N-acetyl(2-aminoethyl)glycine through the N-acetyl
      group at position 1 of the base."

<400> SEQUENCE: 2

Lys Xaa Xaa Xaa Xaa Xaa Xaa Xaa Xaa Xaa Xaa Gly
 1               5                  10

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (2)
<223> OTHER INFORMATION: /note = " Heterocyclic base is attached to
      N-acetyl (2-aminoethyl)glycine through the
      N-acetyl group at position 9 of the base."
<221> NAME/KEY: UNSURE
<222> LOCATION: (3)
<223> OTHER INFORMATION: /note = "Heterocyclic base is attached to
      N-acetyl (2-aminoethyl)glycine through the N-acetyl group
      at position 1 of the base."
<221> NAME/KEY: UNSURE
<222> LOCATION: (4)..(6)
<223> OTHER INFORMATION: /note="Heterocyclic base is attached to
      N-acetyl (2-aminoethyl)glycine through the N-acetyl group
      at position 9 of the base."
<221> NAME/KEY: UNSURE
<222> LOCATION: (7)..(8)
<223> OTHER INFORMATION: /note= "Heterocyclic base is attached to
      N-acetyl (2-aminoethyl)glycine through the N-acetyl group
      at position 1 of the base."
<221> NAME/KEY: UNSURE
<222> LOCATION: (9)
<223> OTHER INFORMATION: /note= "Heterocyclic base is attached to
      N-acetyl (2-aminoethyl)glycine through the N-acetyl group
      at position 9 of the base."
<221> NAME/KEY: UNSURE
<222> LOCATION: (10)..(16)
<223> OTHER INFORMATION: /note = "Heterocyclic base is attached to
      N-acetyl (2-aminoethyl)glycine through the N-acetyl group
      at position 1 of the base."
<221> NAME/KEY: UNSURE
<222> LOCATION: (17)..(18)
```

```
<223> OTHER INFORMATION: /note= "Heterocyclic base is attached to
      N-acetyl (2-aminoethyl)glycine through the N-acetyl group
      at position 9 of the base."
<221> NAME/KEY: UNSURE
<222> LOCATION: (19)
<223> OTHER INFORMATION: /note = "Heterocyclic base is attached to
      N-acetyl (2-aminoethyl)glycine through the N-acetyl group
      at position 1 of the base."
<221> NAME/KEY: UNSURE
<222> LOCATION: (20)..(21)
<223> OTHER INFORMATION: /note = "Heterocyclic base is attached to
      N-acetyl (2-aminoethyl)glycine through the N-acetyl group
      at position 9 of the base."
<221> NAME/KEY: UNSURE
<222> LOCATION: (22)..(24)
<223> OTHER INFORMATION: /note= " Heterocyclic base is attached to
      N-acetyl (2-aminoethyl)glycine through the N-acetyl group
      at position 1 of the base."
<221> NAME/KEY: UNSURE
<222> LOCATION: (25)
<223> OTHER INFORMATION: /note = " Heterocyclic base is attached to
      N-acetyl (2-aminoethyl)glycine through the
      N-acetyl group at position 9 of the base."
<221> NAME/KEY: UNSURE
<222> LOCATION: (26)
<223> OTHER INFORMATION: /note = " Heterocyclic base is attached to
      N-acetyl (2-aminoethyl) glycine through the
      N-acetyl group at position 1 of the base."

<400> SEQUENCE: 3

Gly Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Lys
             20                  25

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (2)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (3)
<223> OTHER INFORMATION: /note= " Heterocyclic base is attached to
      N-acetyl (2-aminoethyl)glycine through the N-acetyl group
      at position 1 of the base."
<221> NAME/KEY: UNSURE
<222> LOCATION: (4)..(6)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (7)..(8)
<223> OTHER INFORMATION: /note= "Heterocyclic base is attached to the
      N-acetyl (2-aminoethyl)glycine through the
      N-acetyl group at position 1 of the base."
<221> NAME/KEY: UNSURE
<222> LOCATION: (9)
<223> OTHER INFORMATION: /note = " Heterocyclic base is attached to
      N-acetyl (aminoethyl)glycine through the N-acetyl
      group at position 9 of the base."
<221> NAME/KEY: UNSURE
<222> LOCATION: (10)..(11)
<223> OTHER INFORMATION: /note= " Heterocyclic base is attached to
      N-acetyl (2-aminoethyl)glycine through the N-acetyl group
      at position 1 of the base.
<221> NAME/KEY: UNSURE
<222> LOCATION: (12)..(13)
<223> OTHER INFORMATION: /note = " Heterocyclic base is attached to
      N-acetyl (2-aminoethyl)glycine throught the
```

```
        N-acetyl group at position 9 of the base."
<221> NAME/KEY: UNSURE
<222> LOCATION: (14)
<223> OTHER INFORMATION: /note = " Heterocyclic base is attached to
      N-acetyl (2-aminoethyl)glycine through the
      N-acetyl group at position 1 of the base."
<221> NAME/KEY: UNSURE
<222> LOCATION: (15)..(16)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (17)..(19)
<223> OTHER INFORMATION: /note= " Heterocyclic base is attached to
      N-acetyl (2-aminoethyl)glycine through the N-acetyl group
      at position 1 of the base."
<221> NAME/KEY: UNSURE
<222> LOCATION: (20)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (21)
<223> OTHER INFORMATION: /note= "Heterocyclic base is attached to
      N-acetyl (2-aminoethyl)glycine through the N-acetyl group
      at position 1 of the base."

<400> SEQUENCE: 4

Gly Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Lys
            20

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (2)
<223> OTHER INFORMATION: /note = " Heterocyclic base is attached to
      N-acetyl (2-aminoethyl)glycine through the
      N-acetyl group at position 9 of the base."
<221> NAME/KEY: UNSURE
<222> LOCATION: (3)
<223> OTHER INFORMATION: /note = " Heterocyclic base is attached to
      N-acetyl (2-aminoethyl)glycine through the
      N-acetyl group at positin 1 of the base."
<221> NAME/KEY: UNSURE
<222> LOCATION: (4)..(6)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (7)..(8)
<223> OTHER INFORMATION: /note= " Heterocyclic base is attached to
      N-acetyl (2-aminoethyl)glycine through the N-acetyl group
      at position 1 of the base."
<221> NAME/KEY: UNSURE
<222> LOCATION: (9)
<223> OTHER INFORMATION: /note= " Heterocyclic base is attached to
      N-acetyl (2-aminoethyl) glycine through the N-acetyl group
      at position 9 of the base."
<221> NAME/KEY: UNSURE
<222> LOCATION: (10)..(11)
<223> OTHER INFORMATION: /note = " Heterocyclic base is attached to
      N-acetyl (2-aminoethyl)glycine through the
      N-acetyl group at position 1 of the base."
<221> NAME/KEY: UNSURE
<222> LOCATION: (12)
<223> OTHER INFORMATION: /note= " Heterocyclic base is attached to
      N-acetyl (2-aminoethyl)glycine through the Nacetyl group at
      position 9 of the base."
<221> NAME/KEY: UNSURE
```

```
<222> LOCATION: (13)..(19)
<223> OTHER INFORMATION: /note = " Heterocyclic base is attached to
      N-acetyl (2-aminoethyl) glycine through the
      N-acetyl group at position 1 of the base."
<221> NAME/KEY: UNSURE
<222> LOCATION: (20)..(21)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (22)
<223> OTHER INFORMATION: /note= "Heterocyclic base is attached to
      N-acetyl (2-aminoethyl)glycine through the N-acetyl group
      at position 1 of the base."
<221> NAME/KEY: UNSURE
<222> LOCATION: (23)..(24)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (25)..(27)
<223> OTHER INFORMATION: /note= " Heterocyclic base is attached to
      N-acetyl (2-aminoethyl)glycine through the N-acetyl group
      at position 1 of the base."
<221> NAME/KEY: UNSURE
<222> LOCATION: (28)
<223> OTHER INFORMATION: /note= " Heterocyclic base is attached to
      N-acetyl (2-aminoethyl)glycine through the N-acetyl group
      at position 9 of the base."
<221> NAME/KEY: UNSURE
<222> LOCATION: (29)
<223> OTHER INFORMATION: /note= " Heterocyclic base is attached to
      N-acetyl (2-aminoethyl)glycine through the N-acetyl group
      at position 1 of the base."

<400> SEQUENCE: 5

Gly Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Lys
                20                  25                  30

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (25)
<223> OTHER INFORMATION: /note= "biotin labeled"

<400> SEQUENCE: 6
gatcccccca ccacgtggtg cctga                                        25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (25)
<223> OTHER INFORMATION: /note= "biotin labeled"

<400> SEQUENCE: 7
gatctcaggc accacgtggt ggggg                                        25

<210> SEQ ID NO 8
<211> LENGTH: 21
<212> TYPE: DNA
```

```
<213> ORGANISM: Artificial Sequence
<220> FEATURE:
<223> OTHER INFORMATION: Description of Artificial Sequence: Novel
      Sequence

<400> SEQUENCE: 8
cgcttggtga ctcagccgga a                                              21

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
gatccaaaaa aaaaag                                                    16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
gatccttttt tttttg                                                    16

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(11)
<223> OTHER INFORMATION: /note= " Heterocyclic base is attached to
      N-acetyl (2-aminoethyl)glycine through the N-acetyl group
      at position 1 of the base."

<400> SEQUENCE: 11

Xaa Xaa Xaa Xaa Xaa Xaa Xaa Xaa Xaa Xaa Lys
 1               5                  10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
aaaaggagag                                                           10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 13
gagaggaaaa                                                           10
```

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 14
aaaagtagag                                                              10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 15
aaaaggtgag                                                              10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 16
gagatgaaaa                                                              10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
gagtggaaaa                                                              10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(5)
<223> OTHER INFORMATION: /note= " Heterocyclic base is attached to
      N-acetyl (2-aminoethyl)glycine gthough the N-acetyl group
      at position 1 of the base."
<221> NAME/KEY: UNSURE
<222> LOCATION: (6)
<223> OTHER INFORMATION: /note=  " Heterocyclic base is attached to
      N-acetyl (2-aminoethyl)glycine through the
      N-acetyl group at position 9 of the base."
<221> NAME/KEY: UNSURE
<222> LOCATION: (7)..(10)
<223> OTHER INFORMATION: /note= " Heterocyclic base is attached to
      N-acetyl (2-aminoethyl)glycine through the N-acetyl group
      at position 1 of the base."

<400> SEQUENCE: 18

```
Xaa Xaa Xaa Xaa Xaa Xaa Xaa Xaa Xaa Xaa Lys
 1               5                   10
```

```
<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19
aaaaaaaaaa                                                            10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20
aaaaagaaaa                                                            10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 21
aaaaataaaa                                                            10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22
aaaagaaaaa                                                            10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23
aaaacaaaaa                                                            10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 24
``` aaaataaaaa				10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(7)
<223> OTHER INFORMATION: /note= " Heterocyclic base is attached to
      N-acetyl (2-aminoethyl)glycine through the N-acetyl group
      at position 1 of the base."

<400> SEQUENCE: 25

Xaa Xaa Xaa Xaa Xaa Xaa Xaa Lys
 1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(9)
<223> OTHER INFORMATION: /note= " Heterocyclic base is attached to
      N-acetyl (2-aminoethyl)glycine through the N-acetyl group
      at position 1 of the base."

<400> SEQUENCE: 26

Xaa Xaa Xaa Xaa Xaa Xaa Xaa Xaa Xaa Lys
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(10)
<223> OTHER INFORMATION: /note= " Heterocyclic base is attached to
      N-acetyl (2-aminoethyl)glycine through the N-acetyl group
      at position 1 of the base."

<400> SEQUENCE: 27

Xaa Xaa Xaa Xaa Xaa Xaa Xaa Xaa Xaa Lys
 1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(8)
<223> OTHER INFORMATION: /note= " Heterocyclic base is attached to
      N-acetyl (2-aminoethyl)glycine through the N-acetyl group
      at position 1 of the base."

<400> SEQUENCE: 28

Xaa Xaa Xaa Xaa Xaa Xaa Xaa Xaa Lys
 1               5

```
<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(8)
<223> OTHER INFORMATION: /note= " Heterocyclic base is attached to
      N-acetyl (2-aminoethyl)glycine through the N-acetyl group
      at position 1 of the base."

<400> SEQUENCE: 29

Xaa Xaa Xaa Xaa Xaa Xaa Xaa Xaa Lys
  1               5

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 30
aaaaacaaaa                                                              10

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 31 tcgactttc tttttg                                                        16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 32
tcgacaaaaa gaaaag                                                       16

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 33
gaagaagaaa atgca                                                        15

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
```

-continued

```
<400> SEQUENCE: 34
gttttcttct tctgca                                                         16

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Novel
      Sequence
<221> NAME/KEY: UNSURE
<222> LOCATION: (1)..(6)
<223> OTHER INFORMATION: /note= " Heterocyclic base is attached to
      N-acetyl (2-aminoethyl)glycine through the N-acetyl group
      at position 1 of the base."

<400> SEQUENCE: 35

Xaa Xaa Xaa Xaa Xaa Xaa Lys
  1               5

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 36
gaagaagaaa agtgac                                                         16

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 37
aatagtagtg                                                                10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 38
attagtagtg                                                                10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 39
gtgatgataa                                                                10

<210> SEQ ID NO 40
<211> LENGTH: 10
<212> TYPE: DNA
```

```
<213> ORGANISM: Artificial Sequence
<220> FEATURE:
<223> OTHER INFORMATION: Description of Artificial Sequence: Novel
      Sequence

<400> SEQUENCE: 40
aaaaccacac                                                            10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 41
cacaccaaaa                                                            10

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 42
cgcttggtga ctcagccgga a                                               21
```